United States Patent
Ting et al.

(10) Patent No.: US 11,466,085 B2
(45) Date of Patent: Oct. 11, 2022

(54) ANTI-PD-L1 NANOBODY, CODING SEQUENCE AND USE THEREOF

(71) Applicant: NANOMAB TECHNOLOGY LIMITED, Central (HK)

(72) Inventors: Hong Hoi Ting, Shanghai (CN); Chung Lim Wong, Shanghai (CN)

(73) Assignee: NANOMAB TECHNOLOGY LIMITED, Central (HK)

( * ) Notice: Subject to any disclaimer, the term of this patent is extended or adjusted under 35 U.S.C. 154(b) by 401 days.

(21) Appl. No.: 16/723,037

(22) Filed: Dec. 20, 2019

(65) Prior Publication Data

US 2020/0148772 A1 May 14, 2020

Related U.S. Application Data

(63) Continuation of application No. 16/085,899, filed as application No. PCT/CN2017/077122 on Mar. 17, 2017, now Pat. No. 10,556,954.

(30) Foreign Application Priority Data

Mar. 18, 2016 (CN) .......................... 201610158493.0

(51) Int. Cl.
| | |
|---|---|
| *A61P 35/00* | (2006.01) |
| *C07K 16/28* | (2006.01) |
| *A61K 39/395* | (2006.01) |
| *C12N 15/63* | (2006.01) |
| *C07K 16/06* | (2006.01) |
| *C12N 15/62* | (2006.01) |
| *C12N 15/85* | (2006.01) |

(52) U.S. Cl.
CPC ........ *C07K 16/2827* (2013.01); *A61K 39/395* (2013.01); *A61P 35/00* (2018.01); *C07K 16/065* (2013.01); *C07K 16/28* (2013.01); *C12N 15/62* (2013.01); *C12N 15/63* (2013.01); *C12N 15/85* (2013.01); *C07K 2317/569* (2013.01); *C12N 2015/8518* (2013.01)

(58) Field of Classification Search
None
See application file for complete search history.

(56) References Cited

U.S. PATENT DOCUMENTS 8,907,065 B2 * 12/2014 Hermans ............ C07K 16/2818
424/130.1
10,556,954 B2 2/2020 Ting et al.

FOREIGN PATENT DOCUMENTS

| | | |
|---|---|---|
| CN | 103421115 A | 12/2013 |
| CN | 103987405 A | 8/2014 |
| CN | 104736168 A | 6/2015 |
| EP | 3330290 A1 | 6/2018 |
| EP | 3348571 A1 | 7/2018 |
| WO | 2008/071447 A2 | 6/2008 |

OTHER PUBLICATIONS

GenBank Accession No. KF179380.1, Comparison of Camelus bactrianus VHH sequences from conventional and heavy chain antibodies. Sep. 21, 2013.
LECOCQ, Nanobody-mediated imaging and inhibition of the immune checkpoint ligand PD-L1. Thesis, Vrije Universiteit Brussel. 53 pages, (2015-2016).
Zhang et al., Structural basis of a novel PD-L1 nanobody for immune checkpoint blockade. Cell Discov. Mar. 7, 2017;3:17004, 12 pages.

* cited by examiner

*Primary Examiner* — Meera Natarajan
(74) *Attorney, Agent, or Firm* — McCarter & English, LLP; Marcie B. Clarke

(57) ABSTRACT

Provided in the present invention are a type of anti-human PD-L1 specific nanobodies and VHH chains thereof, coding sequences of the foregoing nanobodies or VHH chains thereof, corresponding expression vectors and host cells, and a method for producing antibodies.

8 Claims, 1 Drawing Sheet

Specification includes a Sequence Listing.

ANTI-PD-L1 NANOBODY, CODING SEQUENCE AND USE THEREOF

CROSS-REFERENCE TO RELATED APPLICATIONS

This application is a continuation of U.S. application Ser. No. 16/085,899, filed on Sep. 17, 2018, which is a 35 U.S.C. § 371 national stage application of International Application No. PCT/CN2017/077122, filed on Mar. 17, 2017, which in turn claims the benefit of priority to Chinese Patent Application No. 201610158493.0, filed on Mar. 18, 2016. The entire contents of each of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Dec. 20, 2019, is named 130535-00103_SL.txt and is 266,406 bytes in size.

TECHNICAL FIELD

The invention relates to the field of biomedical or biopharmaceutical technology, and more particularly to PD-L1 single domain antibodies and its coding sequence and application.

BACKGROUND TECHNIQUE

Programmed death 1 ligand 1, also known as CD274, is a member of the B7 family and is a ligand for PD-1. PD-L1 is a type I transmembrane protein with a total of 290 amino acids, including an IgV-like region, an IgC-like region, a transmembrane hydrophobic region, and an intracellular region consisting of 30 amino acids.

Unlike other B7 family molecules, PD-L1 has a negative regulatory effect on immune responses. The study found that PD-L1 is mainly expressed in activated T cells, B cells, macrophages and dendritic cells. In addition to lymphocytes, PD-L1 is also expressed in other tissues endothelial cells such as thymus, heart, placenta, etc., as well as various non-lymphoids such as melanoma, liver cancer, gastric cancer, renal cell carcinoma, ovarian cancer, colon cancer, breast cancer, esophageal cancer, head and neck cancer, etc. PD-L1 is versatile in regulating autoreactive T, B cells and immune tolerance, and plays a role in peripheral T and B cell responses. The high expression of PD-L1 on tumor cells is associated with poor prognosis in cancer patients.

Programmed death-1 (PD-1), also known as CD279, is a member of the CD28 family. It has two tyrosine residues in the cytoplasmic region. One located near the N-terminus is in the immunoreceptor tyrosine-based inhibitory motif (ITIM) and another one near the C-terminus is located in the immunoreceptor tyrosine-based switch motif (ITSM). PD-1 is mainly expressed on the surface of activated T lymphocytes, B lymphocytes and macrophages. Under normal conditions, PD-1 can inhibit the function of T lymphocytes and promote the function of Treg, thereby inhibiting autoimmune responses and preventing autoimmune diseases. However, in the occurrence of tumors, PD-L1 expressed by tumor cells combined with PD-1 can promote tumor immune escape by inhibiting lymphocytes. The combination of PD-L1 and PD-1 can lead to a variety of biological changes, leading to immune regulation, such as inhibition of lymphocyte proliferation and activation, inhibition of CD4+ T cell differentiation into Th1 and Th17 cells, inhibition of inflammatory cytokine release, etc.

The successful application of monoclonal antibodies in the detection and bio-targeted treatment of cancer has caused a revolution in cancer treatment. However, the traditional monoclonal antibody (150 kD) molecular mass is too large. It is difficult for monoclonal antibody to penetrate the tissue, resulting in a low effective concentration of the tumor area, and the therapeutic effect is insufficient; the traditional antibody has high immunogenicity, and the modified antibody is difficult to reach the original affinity. In addition, the long-term development of fully humanized traditional antibodies, high production costs, insufficient stability and many other factors limit its application and popularity in the clinic.

Nanobodies are currently the smallest antibody molecules with a molecular weight of $1/10$ of a normal antibody. In addition to the antigenic reactivity of monoclonal antibodies, nano-antibodies possess some unique functional properties, such as small molecular mass, strong stability, good solubility, easy expression, weak immunogenicity, strong penetrability, strong targeting, simple in humanization, low in preparation cost, etc. It almost completely overcomes the shortcomings of traditional antibody long-term development cycle, low stability and harsh storage conditions.

However, there is currently no satisfactory nanobody for PD-L1 in the field. Therefore, there is an urgent need in the field to develop new and specific nanobodies that are effective against PD-L1.

SUMMARY OF THE INVENTION

The object of the present invention is to provide a class of specific nanobodies that are effective against PD-L1.

In the first aspect of the present invention, it provides a VHH chain of an anti-PD-L1 nanobody, the amino acid sequence of which is shown in any one of SEQ ID NOs.: 1-150.

In another preferred embodiment, the PD-L1 is human PD-L1.

Furthermore, a VHH chain of an anti-PD-L1 nanobody is provided, the VHH comprises a frame region FR and a complementary determining region CDR, wherein the CDR comprises the corresponding CDR1, CDR2 and CDR3 of any one of SEQ ID NOs.: 1-150, as well as FR1, FR2, FR3 and FR4 separated by said CDR1-3.

Furthermore, a heavy chain variable region of an anti-human PD-L1 antibody is provided, the heavy chain variable region comprises three complementary determining regions CDR1, CDR2, and CDR3, and the three CDRs comprise the corresponding CDR1, CDR2 and CDR3 of any one of SEQ ID NO.: 1-150.

In another preferred embodiment, the three CDRs comprise CDR1, CDR2 and CDR3 as shown in Table 2.

In the second aspect of the present invention, an anti-PD-L1 nanobody is provided, which is an nanobody against PD-L1 epitope, and has a VHH chain as shown in the amino acid sequence of any one of SEQ ID NOs.: 1-150.

In another preferred embodiment, the anti-PD-L1 nanobody has a high affinity for PD-L1.

In another preferred embodiment, the anti-PD-L1 nanobody has a very high specificity or selectivity for PD-L1 (relative to PD-L2) and has a selectivity ratio (such as a ratio of OD value)(PD-L1/PD-L2) as high as ≥20, preferably 20-40, or 21-35.

The third aspect of the present invention provides a polynucleotide, and the polynucleotide encodes a protein selected from the group consisting of the VHH chain of the anti-PD-L1 nanobody according to the first aspect, or the anti-PD-L1 nanobody according to the second aspect.

In another preferred embodiment, the polynucleotide comprises DNA or RNA.

In another preferred embodiment, the polynucleotide has a nucleotide sequence as shown in any one of SEQ ID NOs.: 151-300.

The fourth aspect of present invention provides an expression vector, the expression vector comprises the polynucleotide according to the third aspect.

The fifth aspect of the present invention provides a host cell, the host cell comprises the expression vector according to the fourth aspect, or the polynucleotide according to the third aspect is integrated within the genome of the host cell.

In another preferred embodiment, the host cell includes a prokaryocyte or an eukaryocyte.

In another preferred embodiment, the host cell is selected from the group consisting of E. coli, and yeast cell.

The sixth aspect of the present invention provides a method for producing an anti-PD-L1 nanobody comprising the steps of:
(a) culturing said host cell according to the fifth aspect under a condition suitable for producing a nanobody, thereby obtaining a culture containing said anti-PD-L1 nanobody; and
(b) isolating or recovering said anti-PD-L1 nanobody from said culture.

In another preferred embodiment, the anti-PD-L1 nanobody has the amino acid sequence as shown in any one of SEQ ID NOs.: 1-150.

The seventh aspect of the present invention provides an immunoconjugate, and the immunoconjugate comprises:
(a) the VHH chain of the anti-PD-L1 nanobody according to the first aspect, or the anti-PD-L1 nanobody according to the second aspect; and
(b) a conjugating part selected from the group consisting of a detectable marker, drug, toxin, cytokine, radionuclide, and enzyme.

In another preferred embodiment, the conjugating part is a drug or toxin.

In another preferred embodiment, the conjugating part is a detectable marker.

In another preferred embodiment, the conjugate is selected from the group consisting of fluorescent or luminescent markers, radiomarkers, MR1 (magnetic resonance imaging) or CT (computed tomography) contrast agents, or enzymes, radionuclides, biotoxins, cytokines (eg, IL-2, etc.), antibodies, antibody Fc fragments, antibody scFv fragments, gold nanoparticics/nanorods, viral particles, liposomes, nanomagnetic particles, prodrug activating enzymes (eg, DT-diaphorase (DTD) or biphenyl hydrolase-like protein (BPHL), chemotherapeutic agents (eg, cisplatin) or any form of nanoparticles, etc. that can produce detectable products.

In another preferred embodiment, the immunoconjugatc contains multivalent (such as bivalent) VHH chains of the anti-PD-L1 nanobody according to the first aspect of the present invention, or the anti-PD-L1 nanobody according to the second aspect of the present invention. Said multivalent refers that the amino acid sequence of the immunoconjugate contains several repeated VHH chains of the anti-PD-L1 nanobody according to the first aspect of the present invention, or the anti-PD-L1 nanobody according to the second aspect of the present invention.

The eighth aspect of the invention provides a use of the anti-PD-L1 nanobody according to the present invention for preparing (a) a reagent for detecting PD-L1 molecule; or (b) a medicament for treating cancers.

In another preferred embodiment, the detecting comprises detection conducted by flow cytometry or cell immunofluorescence.

The ninth aspect of the present invention provides a pharmaceutical composition comprising:
(i) the VHH according to the first aspect of the present invention, the anti-PD-L1 nanobody according to the second aspect of the present invention, or the immunoconjugatc according to seventh aspect of the present invention; and
(ii) a pharmaceutically acceptable carrier.

In another preferred embodiment, said pharmaceutical composition is in a form of injection.

In another preferred embodiment, said pharmaceutical composition is used for preparing a medicament for treating cancers, and said cancer is selected from the group consisting of gastric cancer, liver cancer, leukemia, renal tumor, lung cancer, small intestinal cancer, bone cancer, prostate cancer, colorectal cancer, breast cancer, colon cancer, prostate cancer, cervical cancer, lymphoma, adrenal tumor and bladder tumor.

The tenth aspect of the present invention provides one or more uses of the anti-PD-L1 nanobody according to the present invention:
(i) for detecting human PD-L1 molecule;
(ii) for flow cytometry assay;
(iii) for cell immunofluorescence detection;
(iv) for treating cancer;
(v) for diagnosing cancer.

In another preferred embodiment, the use is non-diagnostic and non-therapeutic.

The eleventh aspect of the present invention provides an antibody comprising: the heavy chain variable region VHH according to the first aspect of the present invention.

In another preferred embodiment, the antibody is an antibody specific for the PD-L1 protein.

In another preferred embodiment, the antibody is a nanobody.

The twelfth aspect of the present invention provides a recombinant protein, and the recombinant protein has:
(i) the sequence of variable region of heavy chain VHH according to the first aspect of the present invention or the sequence of nanobody according to the second aspect of the present invention; and
(ii) an optional tag sequence assisting expression and/or purification.

In another preferred embodiment, the tag sequence includes 6His tag or HA tag.

In another preferred embodiment, the recombinant protein specifically binds to the PD-L1 protein.

The thirteenth aspect of the present invention provides a use of the heavy chain variable region VHH according to the first aspect of the present disclosure, the nanobody according to the second aspect of the present invention, or the immunoconjugate according to seventh aspect of the present invention for preparing a medicament, agent, detecting plate or kit;

wherein, said agent, detecting plate or kit is used for detecting PD-L1 protein in the sample;

wherein, said medicament is used for treating or preventing cancers expressing PD-L1 (i.e. PD-L1 positive).

In another preferred embodiment, said cancer comprises gastric cancer, lymphoma, liver cancer, leukemia, renal tumor, lung cancer, small intestinal cancer, bone cancer, prostate cancer, colorectal cancer, breast cancer, colon cancer, prostate cancer, or adrenal tumors.

The fourteenth aspect of the present invention provides a method for detecting PD-L1 protein in a sample, and said method comprises the steps of:

(1) contacting the sample with the nanobody according to the second aspect of the present invention;

(2) detecting the antigen—antibody complex, wherein the detected complex indicated the presence of PD-L1 protein.

The fifteenth aspect of the present invention provides a method for treating a disease, comprising administering the nanobody or the immunoconjugate according to the present invention to a subject in need.

In another preferred embodiment, said subject includes mammals, such as human.

DRAWINGS DESCRIPTION

DETAILED DESCRIPTION

Figure 1:
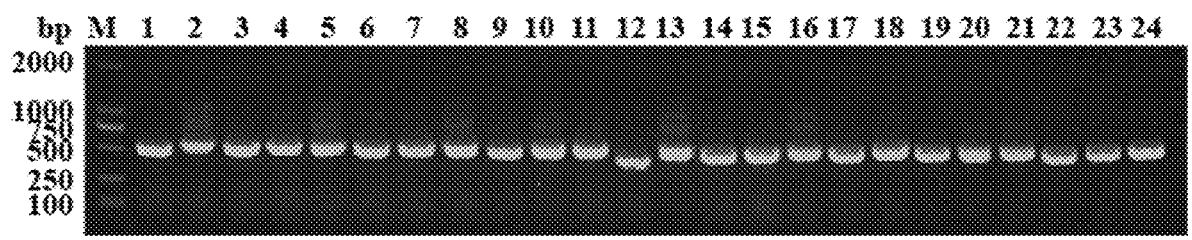
FIG. 1 shows the insertion rate detection plot for the constructed library. The lanes are as follows: Lane M is the DNA molecular marker, and Lanes 1-24 are the PCR products for the detection of the insert, and the PCR product band is approximately 500 bp.

Upon extensive and intensive studies, the inventors have successfully obtained a class of anti-PD-L1 nanobodies after numerous screening. The experimental results show that the nanobodies are not only high specificity, and can efficiently bind to the PD-L1 molecules on cell lines (including the T cells or natural killer cells NK) expressing PD-L1 molecules significantly. It is possible to deliver functional molecules (toxins or small RNAs) by modifying this type of antibody to kill PD-L1 positive cells or perform other functional studies. Based on this discovery, the invention is completed.

In particular, the human PD-L1 protein as antigen was used to immunize a camel, thereby obtaining a gene library of nanobodies with high quality. The PD-L1 protein molecules were conjugated onto an ESLIA board and exhibited correct spatial structure of PD-L1 protein. The antigens in such configuration were used to screen the gene library of nanobodies by phage exhibition technology (phage exhibition of a gene library of camel heavy chain antibody) thereby obtaining genes of nanobodies with PD-L1 specificity. Then the genes were transferred into *E. coli* thereby obtaining the stains which can be effectively expressed in *E. coli* with high specificity.

As used herein, the terms "nanobodies of the invention", "anti-PD-L1 nanobodies of the invention", and "PD-L1 nanobodies of the present invention" are exchangeable and refer to nanobodies that specifically recognize and bind to PD-L1 (including human PD-L1). The more preferable nanobody is one comprising a VHH chain of amino acid sequence as set forth by any one of SEQ ID NO.:1-150.

As used herein, the term "antibody" or "immunoglobulin" is a heterotetrameric glycosaminoglycan protein of about 150,000 Dalton with the same structural features, consisting of two identical light (L) chains and two identical heavy (H) chains. Each light chain is linked to the heavy chain through a covalent disulfide bond, and the number of disulfide bonds between the heavy chains of different immunoglobulin isoforms is different. Each heavy and light chain also has intra-chain disulfide bonds which are regular spaced. Each heavy chain has a variable region (VH) at one end followed by a plurality of constant regions. Each light chain has a variable region (VL) at one end and a constant region at the other end; the constant region of the light chain is opposite to the first constant region of the heavy chain, and the variable region of the light chain is opposite to the variable region of the heavy chain. Special amino acid residues form an interface between the variable regions of the light and heavy chains.

As used herein, the terms "single domain antibody (VHH)" and "nanobodies" have the same meaning referring to a variable region of a heavy chain of an antibody, and construct a single domain antibody (VHH) consisting of only one heavy chain variable region. It is the smallest antigen-binding fragment with complete function. Generally, the antibodies with a natural deficiency of the light chain and the heavy chain constant region 1 (CH1) are first obtained, the variable regions of the heavy chain of the antibody are therefore cloned to construct a single domain antibody (VHH) consisting of only one heavy chain variable region.

As used herein, the term "variable" refers that certain portions of the variable region in the nanobodies vary in sequences, which forms the binding and specificity of various specific antibodies to their particular antigen. However, variability is not uniformly distributed throughout the nanobody variable region. It is concentrated in three segments called complementarity-determining regions (CDRs) or hypervariable regions in the variable regions of the light and heavy chain. The more conserved part of the variable region is called the framework region (FR). The variable regions of the natural heavy and light chains each contain four FR regions, which are substantially in a β-folded configuration, joined by three CDRs which form a linking loop, and in some cases can form a partially β-folded structure. The CDRs in each chain are closely adjacent to the others by the FR regions and form an antigen-binding site of the nanobody with the CDRs of the other chain (see Kabat et al., NIH Publ. No. 91-3242, Volume I, pages 647-669. (1991)). The constant regions are not directly involved in the binding of the nanobody to the antigen, but they exhibit different effects or functions, for example, involve in antibody-dependent cytotoxicity of the antibodies.

As known by those skilled in the art, immunoconjugates and fusion expression products include: conjugates formed by binding drugs, toxins, cytokines, radionuclides, enzymes, and other diagnostic or therapeutic molecules to the nanobodies or fragments thereof of the present invention. The invention also includes a cell surface marker or an antigen that binds to said anti-PD-L1 protein nanobody or the fragment thereof.

As used herein, the term "heavy chain variable region" and "$V_H$" can be used interchangeably.

As used herein, the terms "variable region" and "complementary determining region (CDR)" can be used interchangeably.

In another preferred embodiment, the heavy chain variable region of said nanobody comprises 3 complementary determining regions: CDR1, CDR2, and CDR3.

In another preferred embodiment, the heavy chain of said nanobody comprises the above said heavy chain variable region and a heavy chain constant region.

According to the present invention, the terms "nanobody of the invention", "protein of the invention", and "polypeptide of the invention" are used interchangeably and all refer to a polypeptide, such as a protein or polypeptide having a heavy chain variable region, that specifically binds to PD-L1 protein. They may or may not contain a starting methionine.

The invention also provides other proteins or fusion expression products having the nanobodies of the invention. Specifically, the present invention includes any protein or protein conjugate and fusion expression product (i.e. immunoconjugate and fusion expression product) having a heavy chain containing a variable region, as long as the variable region are identical or at least 90% identical, preferably at least 95% identical to the heavy chain of the nanobody of the present invention.

In general, the antigen-binding properties of a nanobody can be described by three specific regions located in the variable region of the heavy chain, referred as variable regions (CDRs), and the segment is divided into four frame regions (FRs). The amino acid sequences of four FRs are relatively conservative and do not directly participate in binding reactions. These CDRs form a loop structure in which the β-sheets formed by the FRs therebetween are spatially close to each other, and the CDRs on the heavy chain and the CDRs on the corresponding light chain constitute the antigen-binding site of the nanobody. The amino acid sequences of the same type of nanobodies can be compared to determine which amino acids constitute the FR or CDR regions.

The variable regions of the heavy chains of the nanobodies of the invention become a particular interest because at least a part of them is involved in binding antigens. Thus, the present invention includes those molecules having a nanobody heavy chain variable region with a CDR, provided that their CDRs are 90% or more (preferably 95% or more, the most preferably 98% or more) identical to the CDRs identified herein.

The present invention includes not only intact nanobodies but also fragment(s) of immunologically active nanobody or fusion protein(s) formed from nanobodies with other sequences. Therefore, the present invention also includes fragments, derivatives and analogs of the nanobodies.

As used herein, the terms "fragment," "derivative," and "analog" refer to a polypeptide that substantially retains the same biological function or activity of a nanobody of the invention. Polypeptide fragments, derivatives or analogs of the invention may be (i) polypeptides having one or more conservative or non-conservative amino acid residues (preferably non-conservative amino acid residues) substituted. Such substituted amino acid residues may or may not be encoded by the genetic code; or (ii) a polypeptide having a substituent group in one or more amino acid residues; or (iii) a polypeptide formed by fusing a mature polypeptide and another compound (such as a compound that increases the half-life of the polypeptide, for example, polyethylene glycol); or (iv) a polypeptide formed by fusing an additional amino acid sequence to the polypeptide sequence (e.g., a leader or secretory sequence or a sequence used to purify this polypeptide or a proprotein sequence, or a fusion protein formed with a 6 His tag). According to the teachings herein, these fragments, derivatives, and analogs are within the scope of one of ordinary skill in the art.

The nanobody of the present invention refers to a polypeptide including the above CDR regions having PD-L1 protein binding activity. The term also encompasses variant forms of polypeptides comprising the above CDR regions that have the same function as the nanobodies of the invention. These variations include, but are not limited to, deletion insertions and/or substitutions of one or several (usually 1-50, preferably 1-30, more preferably 1-20, optimally 1-10) amino acids, and addition of one or several (generally less than 20, preferably less than 10, and more preferably less than 5) amino acids at C-terminus and/or N-terminus. For example, in the art, the substitution of amino acids with analogical or similar properties usually does not alter the function of the protein. For another example, addition of one or several amino acids at the C-terminus and/or N-terminus usually does not change the function of the protein. The term also includes active fragments and active derivatives of the nanobodies of the invention.

The variant forms of the polypeptide include: homologous sequences, conservative variants, allelic variants, natural mutants, induced mutants, proteins encoded by DNAs capable of hybridizing with DNA encoding the nanobody of the present invention under high or low stringent conditions, and polypeptides or proteins obtained using antiserum against the nanobodies of the invention.

The invention also provides other polypeptides, such as a fusion protein comprising nanobodies or fragments thereof. In addition to almost full-length polypeptides, the present invention also includes fragments of the nanobodies of the invention. Typically, the fragment has at least about 50 contiguous amino acids of the nanobody of the invention, preferably at least about 50 contiguous amino acids, more preferably at least about 80 contiguous amino acids, and most preferably at least about 100 contiguous amino acids.

In the present invention, "a conservative variant of a nanobody of the present invention" refers to the polypeptides in which there are up to 10, preferably up to 8, more preferably up to 5, and most preferably up to 3 amino acids substituted by amino acids having analogical or similar properties, compared to the amino acid sequence of the nanobody of the present invention. These conservative variant polypeptides are preferably produced according to the amino acid substitutions in Table 1.

TABLE 1

| Original residue | Representative substitution | Preferable substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | lie |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above nanobody or fragment or fusion protein thereof. Polynucleotides of the invention may be in the form of DNA or RNA. DNA forms include cDNA, genomic DNA, or synthetic DNA. DNA can be single-stranded or double-stranded. DNA can be a coding strand or a non-coding strand.

Polynucleotides encoding the mature polypeptides of the invention include: coding sequences only encoding mature polypeptide; coding sequences for the mature polypeptide and various additional coding sequences; coding sequences (and optional additional coding sequences) and non-coding sequences for the mature polypeptide.

The term "polynucleotide encoding a polypeptide" may include a polynucleotide that encodes the polypeptide, and may also include a polynucleotide that includes additional coding and/or non-coding sequences.

The invention also relates to polynucleotides that hybridize to the sequences described above and that have at least 50%, preferably at least 70%, and more preferably at least 80% identity between the two sequences. The present invention specifically relates to polynucleotides that can be hybridized to the polynucleotides of the present invention under stringent conditions. In the present invention, "stringent conditions" refers to: (1) hybridization and elution at lower ionic strength and higher temperature, such as 0.2× SSC, 0.1% SDS, 60° C.; or (2) additional denaturants during hybridization, such as 50% (v/v) formamide, 0.1% fetal bovine serum/0.1% Ficoll, 42° C., etc.; or (3) hybridization occurs only under the identity between the two sequences at least over 90%, preferably over 95%. Also, polypeptides encoded by hybridizable polynucleotides have the same biological functions and activities as mature polypeptides.

The full-length nucleotide sequence of the nanobody of the present invention or a fragment thereof can generally be obtained by a PCR amplification method, a recombination method, or an artificial synthesis method. One possible method is to synthesize related sequences using synthetic methods, especially when the fragment length is short. In general, a long sequence of fragments can be obtained by first synthesizing a plurality of small fragments and then connecting them. In addition, the coding sequence of the heavy chain and the expression tag (eg, 6His) can be fused together to form a fusion protein.

Once the concerned sequences have been obtained, the concerned sequences can be obtained in large scale using recombinant methods. Usually, sequences can be obtained by cloning it into a vector, transferring it into cells, and then isolating the sequences from the proliferated host cells by conventional methods. Bio-molecules (nucleic acids, proteins, etc.) to which the present invention relates include bio-molecules that exist in isolated form.

At present, DNA sequences encoding the protein of the present invention (or a fragment thereof, or a derivative thereof) can be obtained completely by chemical synthesis. The DNA sequence then can be introduced into various existing DNA molecules (or e.g. vectors) and cells known in the art. In addition, mutations can also be introduced into the protein sequences of the invention by chemical synthesis.

The invention also relates to vectors comprising the above-mentioned suitable DNA sequences and suitable promoters or control sequences. These vectors can be used to transform an appropriate host cell so that it can express the protein.

The host cell can be a prokaryotic cell, such as a bacterial cell; or a lower eukaryotic cell, such as a yeast cell; or a higher eukaryotic cell, such as a mammalian cell. Representative examples are: *Escherichia coli, Streptomyces*, bacterial cells such as *Salmonella typhimurium*, fungal cells such as yeast, insect cells of *Drosophila* S2 or Sf9, animal cells of CHO, COST, 293 cells, and the like.

The transformation of the host cell with the recombinant DNA can be performed using conventional techniques well known to those skilled in the art. When the host is a prokaryotic organism such as *E. coli*, competent cells capable of absorbing DNA can be harvested after the exponential growth phase and treated with the $CaCl_2$ method. The procedures used are well known in the art. Another method is to use $MgCl_2$. If necessary, conversion can also be performed by electroporation. When the host is eukaryotic, the following DNA transfection methods can be used: calcium phosphate coprecipitation, conventional mechanical methods such as microinjection, electroporation, liposome packaging, and the like.

The obtained transformants can be cultured in a conventional manner to express the polypeptide encoded by the gene of the present invention. Depending on the host cells used, the medium used in the culture may be selected from various conventional media. The culture is performed under conditions suitable for the host cells growth. After the host cells are grown to an appropriate cell density, the selected promoter is induced by a suitable method (such as temperature shift or chemical induction) and the cells are incubated for a further period of time.

The recombinant polypeptide in the above method may be expressed intracellularly, or on the cell membrane, or secreted extracellularly. If necessary, the recombinant protein can be isolated and purified by various separation methods by utilizing its physical, chemical and other characteristics. These methods are well-known to those skilled in the art. Examples of these methods include, but are not limited to: conventional renaturation treatment, treatment with a protein precipitation agent (salting out method), centrifugation, osmotic disruption, super treatment, ultracentrifugation, molecular sieve chromatography (gel filtration), adsorption layer analysis, ion exchange chromatography, high performance liquid chromatography (HPLC), and various other liquid chromatography techniques and the combinations thereof.

The nanobodies of the invention may be used alone or in combination or conjugated with a detectable marker (for diagnostic purposes), a therapeutic agent, a PK (protein kinase) modification moiety, or a combination thereof.

Detectable markers for diagnostic purposes include, but are not limited to: fluorescent or luminescent markers, radioactive markers, MRI (magnetic resonance imaging) or CT (computed tomography) contrast agents, or enzymes capable of producing detectable products.

Therapeutic agents that can be binded or conjugated to the nanobodies of the present invention include, but are not limited to: 1. Radionuclides; 2. Biological poisons; 3. Cytokines such as IL-2, etc.; 4. Gold nanoparticles/nanorods; 5. Viruses Particles; 6. Liposome; 7. Nano magnetic particles; 8. Prodrug activating enzymes (for example, DT-diaphorase (DTD) or biphenyl hydrolase-like protein (BPHL)); 10. Chemotherapeutic agents (for example, cisplatin) or any form of nanoparticles, etc.

Pharmaceutical Composition

The invention also provides a composition. Preferably, said composition is a pharmaceutical composition comprising the above nanobody or active fragment or fusion protein thereof, and a pharmaceutically acceptable carrier. In general, these materials can be formulated in non-toxic, inert, and pharmaceutically acceptable aqueous carrier media wherein the pH is generally about 5-8, preferably about 6-8, although the pH can be varied with the nature of the formulation material and the condition to be treated. The formulated pharmaceutical compositions can be administered by conventional routes including, but not limited to, intratumoral, intraperitoneal, intravenous, or topical administration.

The pharmaceutical composition of the present invention can be directly used to bind PD-L1 protein molecules and thus can be used to treat tumors. In addition, other therapeutic agents can also be used at the same time.

The pharmaceutical composition of the present invention contains a safe and effective amount (for example, 0.001-99 wt %, preferably 0.01-90 wt %, and more preferably 0.1-80 wt %) of the above-mentioned nanobodies of the present invention (or their conjugates) and pharmaceutically acceptable carriers or excipients. Such carriers include, but are not limited to: saline, buffer, dextrose, water, glycerol, ethanol, and the combinations thereof. The drug formulation should be suitable for the mode of administration. The pharmaceutical composition of the present invention may be prepared in the form of an injection, for example, by a conventional method using physiological saline or an aqueous solution containing glucose and other adjuvant. Pharmaceutical compositions such as injections and solutions are preferably made under aseptic conditions. The amount of active ingredient administered is a therapeutically effective amount, for example, about 10 micrograms/kilogram body weight to about 50 milligrams/kilogram body weight per day. In addition, the polypeptides of the invention can also be used with other therapeutic agents.

When a pharmaceutical composition is used, a safe and effective amount of the immune-conjugate is administered to the mammal, wherein the safe and effective amount is usually at least about 10 micrograms/kilogram body weight, and in most cases, no more than about 50 mg/kilogram body weight, preferably the dose is about 10 micrograms/kilogram body weight to about 10 milligrams/kilogram body weight. Of course, factors such as the route of administration and the patient's health status should be considered to define the specific doses, all of which are within the skills of skilled physicians.

Nanobodies with Markers

In a preferred embodiment of the invention, the nanobodies carry detectable markers. More preferably, the marker is selected from the group consisting of isotopes, colloidal gold markers, colored markers, and fluorescent markers.

Colloidal gold markers can be performed using methods known to those skilled in the art. In a preferred embodiment of the invention, the anti-PD-L1 nanobodies are marked with colloidal gold to obtain colloidal gold-markered nanobodies.

The anti-PD-L1 nanobodies of the present invention have very good specificity and high potency.

Detection Method

The invention also relates to a method of detecting PD-L1 protein. The method steps are basically as follows: obtaining a sample of cells and/or tissue; dissolving the sample in a medium; and detecting the level of PD-L1 protein in the dissolved sample.

According to the detection method of the present invention, the sample used is not particularly limited, and a representative example is a sample containing cells which is present in a cell preservation solution.

Kits

The present invention also provides a kit containing a nanobody (or a fragment thereof) or a detection board of the present invention. In a preferred embodiment of the present invention, the kit further includes a container, an instruction, a buffer, and the like.

The present invention also provides a detection kit for detecting the level of PD-L1, and said kit comprises nanobodies that recognize PD-L1 protein, a lysis medium for dissolving a sample, a general reagent and a buffer needed for the detection, such as various buffer, detection markers, detection substrates, etc. The test kit can be an in vitro diagnostic device.

Application

As described above, the nanobodies of the present invention have extensive biological application value and clinical application value. Said applications involve various fields such as diagnosis and treatment of diseases related to PD-L1, basic medical research, and biological research. One preferred application is for clinical diagnosis and targeted treatment of PD-L1.

The main advantages of the present invention include:
(a) the nanobodies of the invention is highly specific to the human PD-L1 protein with correct spatial structure;
(b) the nanobodies of the invention have a strong affinity; and
(c) the nanobodies of the invention are simple to produce.

The invention is further illustrated below in conjunction with specific embodiments. It is to be understood that the examples are merely illustrative of the invention and are not intended to limit the scope of the invention. The experimental methods in which the specific conditions are not indicated in the following examples are usually carried out according to the conditions described in the conventional conditions, for example, Sambrook et al., Molecular Cloning: Laboratory Manual (New York: Cold Spring Harbor Laboratory Press, 1989) manufacturing conditions or according to the conditions recommended by the manufacturer. Unless otherwise stated, percentages and parts are by weight and parts by weight.

Example 1: Construction of a PD-L1 Nanobody Library (1) 1 mg of PD-L1 antigen and Freund's adjuvant are mixed in equal volume, and a Xinjiang Bactrian camel is immunized once a week for 7 times to stimulate B cells to express antigen-specific nano-antibodies;
(2) After 7 immunizations, extract 100 mL of camel peripheral blood lymphocytes and extract total RNA;
(3) Synthesizing cDNA and amplifying VHH by nested PCR;
(4) 20 ug pMECS phage display vector (purchased from Biovector) and 10 ug VHH were digested with restriction endonucleases PstI and NotI, and two fragments were ligated to obtain a ligation product;
(5) The ligation product was transformed into a electrotransformed conventional competent cell TG1, and the PD-L1 nanobody library was constructed and the storage capacity was determined. The storage capacity was $1.5 \times 10^9$.

At the same time, 24 clones were randomly picked for colony PCR detection. The results are shown in FIG. 1. FIG. 1 shows the results of the insertion rate assay of the constructed single domain antibody library. The test results showed that the insertion rate of the library reached about 100%.

Example 2: Nanobody Screening Process for PD-L1

(1) 20 ug of PD-L1 antigen dissolved in 100 mM $NaHCO_3$ with pH 8.2 was coupled to a NUNC plate and placed at 4° C. overnight;
(2) Add 100 uL of 0.1% casein on the next day and block at room temperature for 2 h;

(3) After 2 h, add 100 uL of phage (5×10[11] CFU immunized camelid nano-antibody phage display gene library) for 1 h at room temperature;
(4) Washing 5 times with 0.05% PBS+Tween-20 to wash away non-specific phage;
(5) Dissociate the phage specifically binding to PD-L1 with 100 mM TEA (triethylamine), and infect *E. coli* TG1 cells growing in log phase, incubate at 37° C. for 1 h, and produce and purify the phage for next round of screening. After the same screening process was repeated for 3-4 rounds and gradually enriched.

Example 3: Screening for Specific Single Positive Clones by Using Phage Enzyme-Linked Immunosorbent Assay (ELISA)

(1) From the cell culture dishes containing phage after 3-4 rounds of screening in Example 2, 1000 individual colonies were selected and inoculated into TB medium containing 100 µg/ml of ampicillin (1 liter of TB medium contains 2.3 g of potassium dihydrogen phosphate, 12.52 g of dipotassium hydrogen phosphate, 12 g of peptone, 24 g of yeast extract, 4 ml of glycerol), after growth to log phase, add a final concentration of 1 mmol of IPTG, culture at 28° C. overnight.
(2) The crude antibody was obtained by the infiltration method, and the antibody was transferred to an antigen-coated ELISA plate and placed at room temperature for 1 hour.
(3) Unbound antibody was washed away with PBST, and a mouse anti-HA tag antibody (anti-mouse anti-HA antibody, purchased from Beijing Kangwei Century Biotechnology Co., Ltd.) was added and placed at room temperature for 1 hour.
(4) Unbound antibody was washed away with PBST, and anti-mouse alkaline phosphatase conjugate (goat anti-mouse alkaline phosphatase-labeled antibody, purchased from Amytech Co., Ltd.) was added and placed at room temperature for 1 hour.
(5) Wash the unbound antibody with PBST, add alkaline phosphatase coloring solution, and read the absorbance at 405 nm on an ELISA apparatus.

(6) When the OD value of the sample well is more than 3 times the OD value of the control well (Ratio+/−>3), it is judged as a positive clone hole.
(7) The bacteria of the positive clone well were shaken in a LB liquid containing 100 µg per ml to extract a plasmid and perform sequencing.

Based on the sequence alignment software Vector NTI, the gene sequences of each clone were determined, and a total of 150 different antibodies were identified. The nucleotide sequence of the antibody VHH chain is shown in SEQ ID NO.: 1-150, respectively. Among them, VHH numbered n (n=a positive integer of 1-150), the amino acid sequence of which is SEQ ID NO.: n, and the corresponding coding sequence is SEQ ID NO.: 150+n.

TABLE 2

| Number | Amino acid sequences SEQ ID NO.: | Nucleotide sequences, SEQ ID NO.: | 3 CDR locations (based on amino acid sequences) | | |
|---|---|---|---|---|---|
| | | | CDR1 | CDR2 | CDR3 |
| 1 | 1 | 151 | 26-35 | 51-58 | 97-116 |
| 2 | 2 | 152 | 26-38 | 54-61 | 100-118 |
| 3 | 3 | 153 | 26-35 | 51-58 | 97-116 |
| 4 | 4 | 154 | 26-35 | 51-58 | 97-116 |
| 5 | 5 | 155 | 26-35 | 51-58 | 97-116 |
| 6 | 6 | 156 | 26-35 | 51-57 | 96-115 |
| 7 | 7 | 157 | 26-35 | 52-58 | 97-116 |
| 8 | 8 | 158 | 26-35 | 51-57 | 101-114 |
| 9 | 9 | 159 | 26-35 | 51-58 | 97-113 |
| 10 | 10 | 160 | 26-35 | 51-57 | 96-114 |
| 11 | 11 | 161 | 26-35 | 51-57 | 96-115 |
| 12 | 12 | 162 | 26-35 | 51-58 | 97-116 |
| ... | ... | ... | | | |
| n | n | 150 + n | | | |

The sequences of 150 strains of nanobodies are as follows, wherein the three CDR regions of the 1-12 strain of nanobodies are underlined, respectively.

SEQ ID NO.1
QVQLQESGGGSVQTGGSLRLSCTASTSIYSNNYMAWFSQSPGKGREGVAAVYMDGRFYYADSVKGRFTISLDSAKNTMYL

QMNSLKPEDTAMYYCAAAPGPLSRNYWYTSANYDYWGQGTQVTVSS

SEQ ID NO.2
QVQLQESGGGSVQAGGSLRLSCAVSRYSASNNVIKWMGWFRQAPGKEREGVAALYTSGGNTYYADSVKGRFTISRDYSENT

VSLQMNNLKPEDTGMYYCATTVGTVLAGPLSARKYNYWGQGTQVTVSS

SEQ ID NO.3
QVQLQESGGGSVQTGGSLRLSCAASTSLYSYNYMAWFSQAPGKGREGVAAVYVGDGRPYYADSVKGRFTISLDSAKNAVYLQ

MNSLKPEDTAMYYCAAAPGPLSHNYWYTSANYDYWGQGTQVTVSS

SEQ ID NO.4
QVQLQESGGGSVQTGGSLRLSCAASPSIYSANYMAWFSQAPGKGREGVAAVYIGDGRPYYADSVKGRFTISLDSAKNTVYLQ

MNSLKPEDTAMYYCAAAPGPLGHNYWYTSANYDYWGQGTQVTVSS

```
                                                            SEQ ID NO.5
QVQLQESGGGSVQTGGSLRLSCAASTSIYSNNYMAWFSQAPGKGREGVAAVYIDDGRPYYADSVKGRFTISLDSAKNTVYLQ

MNGLKPEDTAMYYCAAAPGPLSRNYWYTSANYDYWGQGTQVTVSS

SEQ ID NO.6
QVQLQESGGGSVQAGETLRLSCTASGDTFDASGVGWFRQVSGNECDLVSSINRDGTTYYAPSVAGRFTMSQNNAKNTVYLQ

MNSLKPDDTAVYYCATDPAVGIVVRSTCRGPFGYWGQGTQVTVSS

SEQ ID NO.7
QVQLQESGGGSVQTGGSLRLSCACSTSIYSTNYMAWFSQAPGKGREGVAAYIGDGRPYYADSVKGRFTISLDSAKNTVYLQ

MNSLKPEDTAMYYCAAAPGPLSRNYWYTSANYDYWGQGTQVTVSS

SEQ ID NO.8
QVQLQESGGDSVQAGGSLRLACKVPGFTSNTCAMAWFRQAPGKEREVSSISTGGTTGYAESAKGRFTLSKDEAKDTVYLQM

NSLKPEDTAMYFCKSYACRTCIGRYCRTAPDAWGQGTQVTVSS

SEQ ID NO.9
QVQLQESGGGSVQAGGSLRLSCAASGYTYSNDGMGWFRQIPGKEREGVAAISPTGRRTEYADSVQGRFTISRDNAKNMLSL

QMNSLKPEDTGMYYCAREGSGSFSLQNSAVRSWGQGTQVTVSS

SEQ ID NO.10
QVQLQESGGGSVQAGGSLRLSCTAPGFTSKTCAMRWYRQAPGKEREFVSAISTVGTTTYADSVKGRFIISKDEAKDTVYLQINS

LKPEDTAMYSCKTFACRHCIGQSCRTEPDYWGQGTQVTVSS
                                                            SEQ ID NO.11
QVQLQESGGGSVQAGETLRLSCTASGDTFDDSGVGWFRQVSGNECDLVSSINRDGTTYYAPSVAGRFTISQNNAKNTVYLQ

MNSLKPDDTAVYYCATVPAVGIVVRITCRGPFGYWGQGTQVTVSS

SEQ ID NO.12
QVQLQESGGGSVQAGGSLRLSCAASGYTRSSHCMVWFRQAPGKEREGVALIYTGSGSTYYADSVKGRFTISQDNAKKTLYLQ

MNSLKPEDTAMYYCAAGTSSSSCPGLLGPPRYYNWGQGTQVTVSS

SEQ ID NO.13
QVQLQESGGGSVQTGGSLRLSCAASTSIYSNNYMAWFSQNPGKGREGVAAVYIGDGRPYYADSVKGRFTISLDSAKNTVYLQ

MNSLKPEDTAMYYCAAAPGPLSRNYWYTSANYDYWGQGTQVTVSS

SEQ ID NO.14
QVQLQESGGGSVQTGGSLRLSCAASTSIYSNNYMAWFSQAPGKGREGVAAVYIDDGRPYYADSVKGRFTISLDSAKNTVYLQ

VNSLKPEDTAMYYCAAAPGPLSRNYWYTSANYDYWGQGTQVTVSS

SEQ ID NO.15
QVQLQESGGGSVQTGGSLRLSCAASTSIYSNNYMAWFSQAPGKGREGVAAVYIDDGRTYYADSVKGRFTISLDSAKNTVYLQ

MNSLKPEDTAMYYCAAAPGPLSYNYWYTSANYDYWGQGTQVTVSS

SEQ ID NO.16
QVQLQESGGGSVQTGGSLRLSCAASPSIYSNNYMAWFSQAPGKGREGVAAVYIGDGRPYYADSVKGRFTISLDSAKNTVYLQ

MNSLKPEDTAMYYCAAAPGPLSRNYWYTSANYDYWGQGTQVTVSS

SEQ ID NO.17
QVQLQESGGGSVQTGGSLRLSCAASTSIYSLNYMAWFSQAPGKGREGVAAVYIDDGRPYYADHVKGRFTISLDTAKNTVYLQ

MNSLKPEDTAMYYCAAAPGPLSRNYWYTSANYDYWGQGTQVTVSS
```

-continued

SEQ ID NO.18
QVQLQESGGGSVQAGGSLRLSCAASGYTYSSDGMGWFRQTPGKEREGVAAISPTGRRTEYADSVKGRFTISRDNNKNMLSL
QMNSLKPEDTGMYYCAREGSWSFSLANSAVRSWGQGTQVTVSS

SEQ ID NO.19
QVQLQESGGGSVQTGGSLRLSCAASTSIYSNNYMAWFSQAPGKGREGVAAVYIGDGRPYYADSVKGRFTISLDSAKNTVYLQ
MNSLKPEDTAMYYCAAAPGPLSRNYWYTSANYDYWGQGTQVTVSS

SEQ ID NO.20
QVQLQESGGGLVQPGGSLRLSCAASGFTGSIYAMSWVRQAPGKGLEWVSTISSSGGRRFYADSVKGRFTISRDNAKNTLYLQL
NSLKTEDTAMYYCARCSDIYCDNGASYRGQGTQVTVSS

SEQ ID NO.21
QVQLQESGGGSVQTGGSLRLSCAASTSIYSLNYMAWFSQAPGKGREGVAAVYIGDGRPYYADSVKGRFTISLDSAKNTVYLQ
MNSLKSEDTAMYYCAAAPGPLSRHYWYTSANYDYWGQGTQVTVSS

SEQ ID NO.22
QVQLQESGGGSVQTGGSLRLSCAASTSIYSNNYMAWFSQAPRKGREGVAAVYIGDGRPYYADSVKGRFTISLDSAKNTVYLQ
MNSLKPEDTAMYYCAAAPGPLSHNYWYTSANYDYWGQGTQVTVSS

SEQ ID NO.23
QVQLQESGGGSVQTGGSLRLSCAASTSLYSYNYMAWFSQAPGKGREGVAAVYVGDGRPYYADSVKGRFTISLDSAKNTVYLQ
MNSLKPEDTAMYYCAAAPGPLSHNYWYTSANYDYWGQGTQVTVSS

SEQ ID NO.24
QVQLQESGGGSVQTGGSLRLSCTASTSIYSNNYMAWFSQSPGKGREGVAAVYMDDGRPYYADSVKGRFTISLDSAKNTMYL
QMNSLKPEDTAMYYCAAAPGPLSRNYWYTSANYDYWGQGTQVTVSS

SEQ ID NO.25
QVQLQESGGGSVQTGGSLRLSCTASTSIYSNNYMAWFSQAPGKGREGVAAVYIGDGRPYYADSVKGRFTISLDSAKNTVYLQ
MNSLKPEDTAMYYCAAAPGPLSHNYWYTSANYDYWGQGTQVTVSS

SEQ ID NO.26
QVQLQESGGGSVQTGGSLRLSCAASTSIYNNNYMAWFSQAPGKEREGVAAVYIGDGRPYYADSVKGRFTISLDSAKNTVYLQ
MNSLKPEDTAMYYCAAAPGPLSRNYWYTSANYDYWGQGTQVTVSS

SEQ ID NO.27
QVQLQESGGGSVQTGGSLRLSCTASTSIYSNNYMAWFSQSPGKGREGVAAVYMDDGRPYYADSVKGRFTISLDSAKNTMYL
QMNSLKPEDTAMYYCAAAPGPLSRNYWYTSANYDYWGQGTQVTVSS

SEQ ID NO.28
QVQLQESGGGSVQTGGSLRLSCAASTSIYSNNYMAWFRQAPGKGREGVAAVYIDDGRPYYADSVKGRFTISLDSAKNTVYLQ
MNSLKPEDTAMYYCAAAPGPLSRHYWYTSANYDYWGPGTQVTVSS

SEQ ID NO.29
QVQLQESGGGSVRTGGSLRLSCAASPSIYSNNYMAWFSQAPGKGREGVAAVYIDDGRPYYADSVKGRFTISLDSAKNTVYLQ
MNSLKPEDTAMYYCAAAPGPLSRNYWYTSANYDYWGQGTQVTVSS

SEQ ID NO.30
QVQLQESGGGSVQTGGSLRLSCTASTSIYSNNYMAWFSQAPGKGREGVAAVYIDDGRPYYADSVKGRFTISLDSAKNTVYLQ
MNSLKPEDTAMYYCAAAPGPLSRNYWYTSANYDYWGQGTQVTVSS

SEQ ID NO.31
QVQLQESGGGSVQTGGSLRLSCAASTSIYSNNYMAWFRQAPGKGREGVAGVYIGDGRPYYADSVKGRFTISLDSAKNTVYLQ
MNSLKPEDTAMYYCAAAPGPLSHHYWYTSANYDYWGPGTQVTVSS

SEQ ID NO.32
QVQLQESGGGSVQTGGSLRLSCAASTSIYSINYMAWFSQAPGKGREGVAAVYIGDGRPYYADSVKGRFTISLDSAKNTVYLQ
MNSLKPEDTAMYYCAAAPGPLSQHYWYTSANYDYWGQGTQVTVSS

SEQ ID NO.33
QVQLQESGGGSVQTGGSLRLSCACSTSIYSNNYMAWFSQAPGKGREGVAAVYIGDGRPYYADSVKGRFTISLDSAKNTMYLQ
MNSLKPEDTAMYYCAAAPGPLSQHYWYTSANYDYWGQGTQVTVSS

```
                                                                 SEQ ID NO.34
QVQLQESGGGSVQAGGSLRLSCAASGYTRSLYCMGWFRQAPGREREGVAHVYTGDGSPYYADSVKGRFTISQDNGESTLYL
QMNNLKPEDTAMYYCAAGTSALSRPYGPISYGYWYWGQGTQVTVSS

SEQ ID NO.35
QVQLQESGGGSVQTGGSLRLSCTASTSIYSNNYMAWFSQAPGKGREGVAAVYIDDGRPYYADSVKGRFTISLDSAKNTVYLQ
MNSLKPEDTAMYYCAAAPGPLSRNYWYTSANYDYWGQGTQVTVSS

SEQ ID NO.36
QVQLQESGGGSVQTGGSLRLSCAASTSLYSYNYMAWFSQAPGKGREGVAAVYVGDRPYYAASVKGRFTISLDSAKNTVYLQ
MNSLKPEDTAMYYCAAAPGPLSHNYWYTSANYDYWGQGTQVTVSS

SEQ ID NO.37
QVQLQESGGGSVQTGGSLRLSCAASTSIYSINYMAWFRQAPGKGREGVAAVYIDDGRPYYADSVKGRFTISLDSAKNTVYLQ
MTSLKSEDTAMYYCAAAPGPLSRSYWYTSANYDYWGQGTQVTVSS

SEQ ID NO.38
QVQLQESGGGSVQTGGSLRLSCAASTSIYSNNYMAWFSQAPGKGREGVAAVYIGDGRPYYADSAKGRFTISLDSAKNTVYLQ
MNSLKPEDTAMYYCAAAPGPLSRNYWYTSANYDYWGQGTQVTVSS

SEQ ID NO.39
QVQLQESGGGSVQTGGSLRLSCAASTSIYSNNYMAWFSQAPGKGREGVAALYIGDGRPYYADSVKGRFTIALDSAKNTVYLQ
MNGLKPEDTAMYYCAAAPGPLKHNYWYTSANYDYWGQGTQVTVSS

SEQ ID NO.40
QVQLQESGGGSVQTGGSLRLSCAASTSIYSNNYMAWFSQAPGKGREGVAALYIGDGRPYYADSVKGRFTIALDSAKNTVYLQ
MNGLKPEDTAMYYCAAAPGPLKHNYWYTSANYDYWGQGTQVTVSS

SEQ ID NO.41
QVQLQESGGGSVQTGGSLRLSCAASTSIYSNNYMAWFRQAPGKGREGVAAVYIGDGRPYYADSAKGRFTISLDSAKNTVYLQ
MNSLKPEDTAMYYCAAAPGPLSRHYWYTSANYDYWGPGTQVTVSS

SEQ ID NO.42
QVQLQESGGGSVQTGGSLTLSCAASTSIYSYNYMAWFRQAPGKGREGVAAVYIGDGRPYYADSVKGRFTISPDSAKNTVYLQ
MNSLKPEDTAMYYCAAAPGPLSRHYWYTSANYDYWGPGTQVTVSS

SEQ ID NO.43
QVQLQESGGGSVQTGGSLRLSCAASSSIASNNYMAWFSQAPGKGREGVAAVYIGDGRPYYADSVKGRFTISLDSAKNTVYLQ
MNSLKPEDTAMYYCAAAPGPLSRNYWYTSANYDYWGQGTQVTVSS

SEQ ID NO.44
QVQLQESGGGSVRTGGSLRLSCAASTSIYSLNYMAWFSQAPGKGREGVAAVYIDDGRPYYADHVKGRFTISLDTAKNTVYLQ
MNSLKPEDTAMYYCAAAPGPLSRNYWYTSANYDYWGQGTQVTVSS

SEQ ID NO.45
QVQLQESGGGLVQPGGSLRLSCAASGFTFSIKAMSWVRQAPGKGLEWVSTIDSGGGRRYYADSVKGRFTISRDNAKNTLYLQ
LSSLKTEDTAMYFCARCSDIYCYNGASYRGQGTQVTVSS

SEQ ID NO.46
QVQLQESGGGSVQTGGSLRLSCAASTSIDSNNYMAWFRQAPGKGREGVAAVYIDDGRPYYADSVKGRFTISLDSAKNTVYLQ
MNSLKPEDTAMYYCAAAPGPLSRHYWYTSANYDYWGPGTQVTVSS

SEQ ID NO.47
QVQLQESGGGSVQTGGSLRLSCTASTSIYNNNYMAWFSQSPGKGREGVAAVYMDDGRPYYADSVKGRFTISLDSAKNTMYL
QMNSLKPEDTAMYYCAAAPGPLSRNYWYTSANYDYWGQGTQVTVSS

SEQ ID NO.48
QVQLQESGGGSVQTGGSLRLSCAASTSIYSNNYMAWFSQAPGKGREGVAAVYIDDGRTYYADSVKGRFTISLDSAKNTVYLQ
MNSLKPEDTAMYYCAAAPGPLSHNYWYASANYDYWGQGTQVTVSS

SEQ ID NO.49
QVQLQESGGGSVQTGGSLRLSCAASTSIYSINYMAWFSQAPGKGREGVAAVYIDDGRPYYADSVKGRFTISLDSAKNTVYLQ
MNSLKPEDTAMYYCAAAPGPLSRNYWYTSANYDYWGQGTQVTVSS
```

SEQ ID NO.50
QVQLQESGGGLVQPGGSLRLSCIASGFTFSIMAMSWVRQAPGKGLEWVSTINSDGGKTYYADSVKGRFTISRDNAKNTLYLQ
LNSLRTEDMAMYYCRRCADIYCSGSGGWTGQGTQVTVSS

SEQ ID NO.51
QVQLQESGGGSVQTGGSLRLSCTASTSIYSNSYMAWFSQAPGKGREGVAAVYIDDGRPYYADSVKGRFTISLDSAKNTVYLQ
MNSLKPEDTAMYYCAAAPGPLSRHYWYTSANYDYWGQGTQVTVSS

SEQ ID NO.52
QVQLQESGGGSVQTGGSLRLSCAASTSIYSNNYMAWFRQAPGKGREGVAAVYVDDGRPYYADSVKGRFTISRDSAKNTVYL
QMNSLKPEDTAMYYCAAAPGPLSRHYWYTSANYDYWGPGTQVTVSS

SEQ ID NO.53
QVQLQESGGGSVQTGGSLRLSCAASTSIYSNNYMAWFSQAPGKGREGVAAVYIDDGRPYYADSVKGRFTISLDSAKNTVYLQ
MNSLKPEDTAMYYCAAAPGPLSRNYWYTSANYDYWGQGTQVTVSS

SEQ ID NO.54
QVQLQESGGGSVQTGGSLRLSCAPSTSIYDNNYMAWFSQAPGKGREGVAAIYIDDGRPYYADSVKGRFTISLDSAKNTVYLQ
MNSLKPEDTAMYYCAAAPGPLSHNYWYTSANYDYWGQGTQVTVSS

SEQ ID NO.55
QVQLQESGGGSVQTGGSLRLSCVASTSIFSNNYMAWFSQAPGKGREGVAAVYIGDGRPYYADSVKGRFTISLDSAKNTVYLQ
MNSLKPEDTAMYYCAAAPGPLSHNYWYTSANYDYWGQGTQVTVSS

SEQ ID NO.56
QVQLQESGGGSVQTGGSLRLSCAASPSIYSANYMAWFSQAPGKGREGVAAVYIGDGRPYYADSVKGRFTISLDSAKSTVYLQ
MNSLKPEDTAMYYCAAAPGPLSHNYWYTSANYDYWGQGTQVTVSS

SEQ ID NO.57
QVQLQESGGGSVQTGGSLRLSCAASTSIYSINYMAWFSQAPGKGREGVAAVYIDDGRPYYADSVKGRFTISLDSAKNTVYLQ
MNSLKSEDTAMYYCAAAPGPLSRNYWYTSANYDYWGQGTQVTVSS

SEQ ID NO.58
QVQLQESGGGLVQPGGSLRLSCALSGFTSTIYAMSWVRQAPGKGLEWVSTINSDGGYRYYADSVKGRFTISRDNAKNTLYLQL
NSPKTEDTAMYYCARCSDIYCYNGPSYRGQGTQVTVSS

SEQ ID NO.59
QVQLQESGGGSVQTGGSLRLSCACSTSIYSNNYMAWFSQAPGKGREGVAAVYIGDGRPYYTDSVKGRFTISLDSAKNTLYLQ
MNSLKPEDTAMYYCAAAPGPLSHNYWYTSANYDYWGQGTQVTVSS

SEQ ID NO.60
QVQLQESGGGSVQTGGSLRLSCAASTSIYSMNYMAWFSQAPGKGREGVAAVYIEDGRPYYADSVKGRFTISPDRAKNTVYLQ
MNSLKPEDTAMYYCAAAPGPLSRNYWYTSANYDYWGQGTQVTVSS

SEQ ID NO.61
QVQLQESGGGLVQPGGSLRLSCAASGFDFSSRAMSWVRQAPGKGLEWVSTINSGGGSRYYADSVKGRFTTSRDNAKNTLAL
QLNSLKTEDTAMYYCARCSDIYCDNGAWYRGQGTQVTVSS

SEQ ID NO.62
QVQLQESGGGSVQAGGSLRLSCAASTSIYSNNYMAWFRQTPGKGREGVAAVYIDDGRPYYADSVKGRFTISLDSAKNTVYLQ
MNSLKPEDTAMYYCAAAPGPLSHDYWYTSANYDYWGPGTQVTVSS

SEQ ID NO.63
QVQLQESGGGSVQTGGSLRLSCAASTSIYSNNYMAWFSQAPGKGREGVAAVYIDDGRPYYADSVKGRFTISLDSAKNTVYLQ
MNRLKPEDTAMYYCAAAPGPLSHNYWYTSANYDYWGQGTQVTVSS

SEQ ID NO.64
QVQLQESGGGSVQTGGSLRLSCAASTSIYSNNYMAWFSQAPGKGREGVAAVYIDDGRPYYADSVKGRFTISLDSAKNTVYLQ
MNSLKPEDTAMYYCAATPGPLSQHYWYTSANYDYWGQGTQVTVSS

SEQ ID NO.65
QVQLQESGGGLVQPGGSLRLSCAASGFTFSILAMSWVRQAPGKGLEWISTINNSGGTTFYADSVKGRFTISRDNAKNTLYLQL
NSLRTEDTAMYYCRRCTDIYCSLSGGWTGQGTQVTVSS

-continued

SEQ ID NO.66
QVQLQESGGGSVQTGGSLRLSCAASTSIYNNNYMAWFSQAPGKGREGVAAVYVGDGRTYYADSVKGRFTISLDSAKNTVYL
QMNSLKPEDTAMYYCAAAPGPLSHNYWYTSANYDYWGQGTQVTVSS

SEQ ID NO.67
QVQLQESGGGSVQTGGSLRLSCTASTSIYSNNYMAWFSQAPGKGREGVAAVYIDDGRPYYADSVKGRFTISLDSAKNTVYLQ
MNSLKPEDTAMYYCAAAPGPLSRNYWYTSANYDYWGQGTQVTVSS

SEQ ID NO.68
QVQLQESGGGSVQTGGSLRLSCTCSTSIYSNNYMAWFSQAPGKGREGVAAVYIGDGRPYYADSVKGRFTISLDSAKNTVYLQ
MNSLKPEDTAMYYCAAAPGPLSHNYWYTSANYDYWGQGTQVTVSS

SEQ ID NO.69
QVQLQESGGGSVQTGGSLRLSCAASTSIYSNNYMAWFSQAPGKGREGVAAVYIGDGRPYYADSVKGRFTISLDSAKNTVYLQ
MNSLKPEDTAMYYCAAAPGPLSHNYWYTSANYDYWGQGTQVTVSS

SEQ ID NO.70
QVQLQESGGGLVQPGGSLRLSCAASGFTFSIRAMSWVRQAPGKGLEWVSTINSGGDSRYYADSVKGRFTISRDNAKNTMYL
QLNSLKTEDTAMYYCVRCSDIYCYNGASYRGQGTQVTVSS

SEQ ID NO.71
QVQLQESGGGLVQPGGSLRLSCAASGFTFSSYDMSWVRQAPGKGIEWVSVINSGGSNTDYADSVKGRFTISRDNAKNTLYLQ
MNSLKTEDTAVYYCATAWMGYSDYLDGIARGQGTQVTVSS

SEQ ID NO.72
QVQLQESGGGLVQPGGSLRLSCEASGLPFSIIAMSWVRQAPGKGLEWVSTINSDGGTTHYADSVKGRFTISRDNAKNTLYLQL
NSLRTEDTAMYYCRRCTDIYCSGSGGWTGQGTQVTVSS

SEQ ID NO.73
QVQLQESGGGLVQPGGSLRLSCEASGLPFSIIAMSWVRQAPGKGLEWVSTINSDGGTTHYADSVKGRFTISRDNAKNTLYLQL
NSLRTEDTAMYYCRRCTDIYCSGFGGWTGQGTQVTVSS

SEQ ID NO.74
QVQLQESGGGSVQAGGSLRLSCAASGFTGSIYAMSWVRQAPGKGLEWVSTISSSGGRRFYADSVKGRFTISRDNAKNTLYLQ
LNSLKTEDTAMYYCARCSDIYCDNGASYRGQGTQVTVSS

SEQ ID NO.75
QVQLQESGGGSVQTGGSLRLSCAASTSIYSNNYMAWFRQAPGKGREGVAAVYIGDGRPYYADSAKGRFTISLDSAKNTVYLH
MNSLKPEDTAMYYCAAAPGPLSRHYWYTSANYDYWGPGTQVTVSS

SEQ ID NO.76
QVQLQESGGGSVQTGGSLRLSCAASTSIYSNNYMAWFRQVPGKGREGVAAVYIDDGRTYYADSVKGRFTISLDSAKNTVYLQ
MNSLKPEDTAMYYCAAAPGPLSRHYWYTSANYDYWGPGTQVTVSS

SEQ ID NO.77
QVQLQESGGGSVQTGGSLRLSCTASTSIYSNNYMAWFSQAPGKGREGVAAVYIDDGRPYYADSVKGRFTISLDSAKNTVYLQ
MNSLKPEDTAMYYCAAAPGPLSRNYWYTSANYDYWGQGTQVTVSS

SEQ ID NO.78
QVQLQESGGGSVQTGGSLRLSCAASTSLYSYNYMAWFSQAPGKGREGVAAVYVGDGRPYYADSVKGRFTISLDSAKNTVYLQ
MNSLKPEDTAMYYCAAAPGPLSHNYWYTSANYDYWGQGTQVTVSS

SEQ ID NO.79
QVQLQESGGGLVQPGGSLRLSCAASGLPFSIIAMSWVRQAPGKGIEWVSTINSGGGTTHYADSVKGRFTISRDNAKNTLYLQL
NSLRTEDTAVYYCRRCADIYCSGSGGWTGLGTQVTVSS

SEQ ID NO.80
QVQLQESGGGSVQTGGSLRLSCVASTSIYSNNYMAWFSQAPGKGREGVAAVYIDDGRPYYADSVKGRFTISLDSAKNTVYLQ
MNSLKPEDTAMYYCAAAPGPLSRSYWYTSANYDYWGQGTQVTVSS

SEQ ID NO.81
QVQLQESGGGSVQTGGSLRLSCAASTSIYSNNYMAWFSQAPGKGREGVAAVYIDDGRTYYADSVKGRFTISLDSAKNTVYLQ
MNSLKPEDTAMYYCAAAPGPLSRNYWYTSANYDYWGQGTQVTVSS

```
                                                                SEQ ID NO.82
QVQLQESGGGSVQTGGSLRLSCTASTSIYSNNYMAWFSQAPGKGREGVAAVYIDDGRPYYADSVKGRFTISLDSAKNTVYLQ

MNSLKPEDTAMYYCAAAPGPLSRNYWYTSANYDYWGQGTQVTVSS

SEQ ID NO.83
QVQLQESGGGLVQTGGSLRLSCAASTSIYSNNYLAWFSQAPGKGREGVAAVYIGDGRPYYADSVKGRFPISLNSAQNKVYLQ

MNSLKPEDTAMYYCAAAPGPLSRNYWYTSANYDYWGQGTQVTVSS

SEQ ID NO.84
QVQLQESGGGSVQTGGSLRLSCAASTSIDSNNYMAWFRQAPGKGREGVAAVYIDDGRPYYADSVKGRFTISLDSAKNTVYLQ

MNSLKPEDTAMYYCAAAPGPLSRHYWYTSANYDYWGPGTQVTVSS

SEQ ID NO.85
QVQLQESGGGSVQTGGSLRLSCAASTSIYSNNYMAWFSQAPGKGREGVAAVYIADDRPYYADSVKGRFTISLDSAKNTVYLQ

MNSLKPEDTAMYYCAAAPGPLSRNYWYTSANYDYWGQGTQVTVSS

SEQ ID NO.86
QVQLQDSGGGSVQTGGSLRLSCAASTSIYSINYMAWFSQAPGKGREGVAAVYTGDGRPYYADSVKGRFTISLDSAKNTVYLQ

MNSLKPEDTAMYYCAAAPGPLSRNYWYTSANYDYWGQGTQVTVSS

SEQ ID NO.87
QVQLQESGGGSVQAGGSLRLSCAASGYTRSSYCMGWFRQAPGKERERVAYIYSGSGSTHYADSVKGRFTISQDNGKNTLYLQ

MNNLKPEDTAMYYCAAGTSGTSCPTGAFMYEYWYWGQGTQVTVSS

SEQ ID NO.88
QVQLQESGGGSVQAGGSLRLSCAASTSIYSNNYMAWFRQAPGKGREGVAAVYVGDGRPYYADSVKGRFTISLDSAKNTVYL

QMNSLKPEDTAMYYCAAAPGPLSHNYWYTSANYDYWGQGTQVTVSS

SEQ ID NO.89
QVQLQESGGGSVQTGGSLRLSCAASTSIYSNNYMAWFSQAPGKGREGVAAVYIGDGRPYYADSVKGRFTISLDSARNTVYLQ

MNSLKPEDTAMYYCAAAPGPLSRHYWYTSANYDYWGQGTQVTVSS

SEQ ID NO.90
QVQLQESGGGSVQAGGSLRLSCAASTSIYSNNYMAWFSQAPGKGREGVAAVYIDDGRPYYADSVKGRFTISLDSAKNTVYLQ

MNSLKPEDTAMYYCAAAPGPLSRNYWYTSANYDYWGQGTQVTVSS

SEQ ID NO.91
QVQLQESGGDLVQPGGSLRLSCAASGLPFSIIAMSWVRQAPGKGLEWVSTINNDGGTTHYADSVKGRFTISRDNAKNTLYLQ

LNSLRTEDTAMYYCRRCTDIYCSGSGGWTGQGTQVTVSS

SEQ ID NO.92
QVQLQESGGGSVQTGGSLRLSCAASTSIYNNNYMAWFRQAPGKGREGVAAVYIDDGRPYYADSVKGRFTISLDSAKNTVYLQ

MNSLKPEDTAMYYCAAAPGPLSRHYWYTSANYDYWGPGTQVTVSS

SEQ ID NO.93
QVQLQESGGGSVQTGGSLRLSCAASTSIYSNNYMAWFRQAPGKGREGVAAVYIGDGRTYYADSAKGRFTISLDSAKNTVYLH

MNSLKPDDTAMYYCAAAPGPLTRHFWYTSANYDYWGPGTQVTVSS

SEQ ID NO.94
QVQLQESGGGSVQTGGSLRLSCAASTSLYSYNYMAWFSQAPGKGRGGVAAVYVGDGRPYYADSVKGRFTISLDSAKNTVYL

QMNSLKPEDTAMYYCAAAPGPLSHNYWYTSANYDYWGQGTQVTVSS

SEQ ID NO.95
QVQLQESGGGSVQAGGSLRLSCAASGYTVSNNYMGWFRQAPGKGEGVAAVYIGDGRPYYADSVKGRFTISLDSAKNTVYL

QMNSLKPEDTAMYYCAAAPGPLSQHYWYTSANYDYWGQGTQVTVSS

SEQ ID NO.96
QVQLQESGGGLVQPGGSLRLSCAAFGFTFGSYWMKWVRQAPGKDLEWVPIIDNGGRSTWYADSVKGRFTISRDNAKNSLYL

QLNSLKIEDTAMYYCADRNGNRGQGTQVTVSS

SEQ ID NO.97
QVQLQESGGGSVQTGGSLRHSCAASTSIYSNNYMAWFSQAPGKGREGVAAVYIDDGRPYYADSVKGRFTISLDSAKNTVYLQ

MNSLKPEDTAMYYCAAAPGPLSHNYWYTSANYDYWGQGTQVTVSS
```

```
                                                              SEQ ID NO.98
QVQLQESGGGSVQTGGSLRHSCAASTSIYSNNYMAWFSQAPGKGREGVAAVYIDDGRPYYADSVKGRFTISLDSAKNTVYLQ
MNSLKPEDTAMYYCAAAPGPLSHNYWYTSANYDYWGQGTQVTVSS

SEQ ID NO.99
QVQLQESGGGSVTTGGSLRLSCAASTSIYSNNYMAWFRQAPGKGREGVAAVYIGDGRPYYADSVKGRFTISLDSAKNTVYLQ
MNSLKPEDTAMYYCAAAPGPLSRHYWYTSANYDYWGPGTQVTVSS

SEQ ID NO.100
QVQLQESGGGLVQPGGSLRLSCAASGFTFSIMAMSWVRQAPGRGLEWVSTINSDGGKTYYADSVKGRFTASRDNAKNTLYL
QLNSLRTEDTAMYYCRRCADIYCSGSGGWTGQGTQVTVSS

SEQ ID NO.101
QVQLQESGGGSVQTGGSLRLSCAVSGFTDTYFALGWFRQAPGKEREGVAAIDSDGSTSYADSVKGRFTISKDNAKNTVYLQM
NSLKPEDTAMYYCAAAPGPLSRNYWYTSANYDYWGQGTQVTVSS

SEQ ID NO.102
QVQLQESGGGSVQTGGSLRLSCAASTSIYSNNYMAWFRQAPAKGREGVAAVYIGDGRPYYADSVKGRFTISLDSAKNTVYLQ
MNSLKPEDTAIYYCAAAPGPLSRHYWYTSANYDYWGPGTQVTVSS

SEQ ID NO.103
QVQLQESGGGSVQTGGSLRLSCAASTSIYNNNYMAWFSQAPGKGREGVAAVYIEDGRPYYADSVKGRFTISLDSAKNTVYLQ
MNSLKPEDTAMYYCAAAPGPLSRNYWYTSANYDYWGQGTQVTVSS

SEQ ID NO.104
QVQLQESGGGSVQTGGSLRLSCAASTSIYSNNYMAWFRQAPGKGREGVAAVYIDDGRTYYADSVKGRFAISLDSAKNTVYLQ
MNSLKPEDTAMYYCAAAPGPLSRHYWYTSANYDYWGPGTQVTVSS

SEQ ID NO.105
QVQLQESGGGLVQPGGSLRLSCAASGFTFSSLAMSWVRQAPGKGLEWVSTINSGGVYTYYADSVKGRFTISRDNAKNTLYLQ
LNNLRTEDTAMYYCRRCTDIYCSGSGGWTGQGTQVTVSS

SEQ ID NO.106
QVQLQESGGGLVQPGGSLRLSCAVSGFTFSIIAMSWVRQAPGKGLEWVSTINSDGGTTYYADSVKGRFTISRDNAKNTLYLQL
NSLRTEDTAMYYCRRCADIYCSGSGGWTGQGTQVTVSS

SEQ ID NO.107
QVQLQESGGGLVQPGGSLRLSCEASGLPFSIIAMSWVRQAPGKGLEWVSTINSDGGTTHYADSVKGRFTISRDNAKNTLYLQL
NSLRSEDTAMYYCRRCTDIYCSGSGGSTKGQGTQVTVSS

SEQ ID NO.108
QVQLQESGGGSVQTGGSLRLSCAASTSIYSNNYMAWFRQAPGKGREGVAAVYIGDGRPYYADSVKGRFTISLDSAKNTVYLQ
MNSLKPEDTAMYYCAAAPGPLSRHYWYTTANYDYWGPGTQVTVSS

SEQ ID NO.109
QVQLQESGGGSVQAGGSLRLSCAASGYTRSSYCMGWFRQAPGKERERVAHIYTGSGTTHYADSMKGRFTISQDNGKNTYL
QMNNLKPEDTAMYYCAAGTSGTSCATGPFVYGYWYWGQGTQVTVSS

SEQ ID NO.110
QVQLQESGGGSVQAGGSLRLSCAYTPRRLCMGMGWFRQGLGKEREGVATIDDAGSTTYADSVKARFTISQDNAKNTLYLQ
MDSLKPEDSAMYYCAARAGVGWYQVSCPEESRTSAFVYWGQGTQVTVSS

SEQ ID NO.111
QVQLQESGGGSVQTGGSLRLSCAASTSIYNNNYMAWFSQAPGKGREGVAAVYIEDGRPYYADSVKGRFTISLDSAKNTVYLQ
MNSLKPEDTAMYYCAAAPGPLSRNYWYTSANYDYWGQGTQVTVSS

SEQ ID NO.112
QVQLQESGGGLVQPGGSLRLSCAASGLTFSIVAMSWVRQAPGKGLEWVSTINSDGGSTYYADSVKGRFTISRDNAKNTLYLQL
NSLRTEDTAMYYCRRCTDIYCSGSGGWTGQGTQVTVSS

SEQ ID NO.113
QVQLQESGGGSVQTGGSLRLSCAASTSIISFNYMAWFRRAPGKGREGVAAVYIDDGRPYYADSVKGRFTISLDSAKNTVYLQM
GSLRPEDTAMYYCAAAPGPLSRNYWHTPANYDYWGQGTQVTVSS
```

SEQ ID NO.114
QVQLQESGGGSVQTGGSLRLSCAASGYAGRLYSMGWFRQVAGKEREGVSSIESDGSTFYTDSVKGRFTTTRDSAKNTLYLQM
NNLKPEDTAMYYCAAFCLRVGHGGRCTEYKYWGRGTQVTVSS

SEQ ID NO.115
QVQLQESGGGSVQAGGSLRLSCAASGYTRSSYCMGWFRQAPGKERERVAHIYTGSGSTHYADSVKGRFTISQDNGKNTLYLQ
MNNLKPEDTAMYYCAAGTSGTSCATGPFVYKYWYWGQGTQVTVSS

SEQ ID NO.116
QLQESGGGLVQPGGSLRLSCAASGFAFSTYAMSWVRQAPGKGLEWVSGINGGGGNTYYADSVKGRFTISRDNAKNTLYLQL
NSLKTEDTAMYYCGQGAYWAYCNGGYCNPPGQGTQVTVSS

SEQ ID NO.117
QVQLQESGGGSVQTGGSLRLSCAASTSIYSNNYMAWFSQAPGKGREGVAAVYIGDGRPYYADSVKGRFTISLDSAKDTVYLQ
MNSLKPEDTAMYYCAAAPGPLSRNYWYTSANYDYWGQGTQVTVSS

SEQ ID NO.118
QVQLQESGGGSVQTGGSLRLSCAASASIYSNNYMAWFSQAPGKGREGVAAVYIGDGRPYYDDSVKGLFTISLDSAKNTVYLQ
MNSLKPEDTAMYYCAAAPGPLIRNYWYTSANYDYWGQGTQVTVSS

SEQ ID NO.119
QVQLQESGGGSVQTGGSLRLSCAASTSLYSYNYMAWFSQAPGKGREGVAAVYVGDGRPYYADSVKGRFTISLDSAKNTVYLQ
MNSLKPEDTAMYYCAAAPGPLSRNYWYTSANYDYWGQGTQVTVSS

SEQ ID NO.120
QVQLQESGGGSVQAGGSLRLSCTAPGFTSNTCAMAWFRQAPGKEREFVSSMSTVGSTRFADSVKGRFTISKDEVKDTVYLQ
MNSLKPEDTAMYFCKTYACRECTGRYCRTAPDAWGQGTQVTVSS

SEQ ID NO.121
QVQLQESGGGSAQAGGSLRLSCTAPGFTSNTCAMAWYRQAPGKEREFVSSRSTVGTTGYADSVKGRFTISKDEAKDTVYLQ
MNSLKPEDTAMYFCKTYACRNCIGRHCRTAPDAWGQGTQVTVSS

SEQ ID NO.122
QVQLQESGGGSVQAGGSLRLSCTAPGFTSNTCAMAWFRQAPGKEREFVSSLSTVGTTGYADSVKGRFTISKDEAKDTVYLLM
NSLKPEDTAMYFCKTFACRDCSGRYCRTAPDAWGQGTQVTVSS

SEQ ID NO.123
QVQLQESGGGSVQAGGSLRLSCTAPGFTSNTCAMAWYRQAPGKEREFVSSRSTVGTTGYADSVKGRFTISKDEAKDTVYLQ
MNSLKPEDTAMYFCKTYACRNCIGRHCRTAPDAWGQGTQVTVSS

SEQ ID NO.124
QVQLQESGGGSVQAGRSLRLSCAVSRYSASNNVIKWMGWFRQAPGKEREGVAALYTSGGNTYYADSVKGRFTISRDYSENT
VSLQMNNLKPEDTGMYYCAATVGTVLAGPLSARKYNYWGQGTQVTVSS

SEQ ID NO.125
QVQLQESGGGLVQPGGSLRLSCAASGFTFSNSDMAWFRQAPGKGLEWVSVIDSGGGYTYYADSVKGRFTISRDNAENTLYL
QLNSLKTEDTAMYYCAKTDLRYSRIYPYGKWGQGTQVTVSS

SEQ ID NO.126
QVQLQESGGGSVQAGRSLRLPCAVSRYSASNNVIKWMGWFRQAPGKEREGVAALYTSGGNTYYADSVKGRFTISRDYSENT
VSLQMNNLKPEDTGMYYCAATVGTVLAGPLSARKYNYWGQGTQVTVSS

SEQ ID NO.127
QVQLQESGGGLVQAGGSLTLSCRGSGFTSNTCAMAWFRQAPGKEREFVSSMSTVGSTRFADSVKGRFTISKDEAKDTVYLQ
MNSLKPEDTAMYFCKTYACRECTGRYCRTAPDAWGQGTQVTVSS

SEQ ID NO.128
QVQLQESGGGSVQAGGSLRLSCTAPGFTSNTCAMAWFRQAPGKEREFVSSMSTGGTTGYGDSVKGRFTSSKDAAKDTVYLQ
MNSLKPEDTAIYFCKTYACRDCIGRYCRTAPDAWGQGTQVTVSS

SEQ ID NO.129
QVQLQESGGGSVQAGGSLRLSCTAPGFTSNTCAMAWYRQAPGKEREFVSSRSTVGTTGYADSVKGRFTLSKDEAKDTVYLQ
MNSLKPEDTAMYFCKTYACRNCIGRHCRTAPDAWGQGTQVTVSS

SEQ ID NO.130
QVQLQESGGGSVQAGETLRLSCTVSGDTFEASGVGWFRQVSGNECDLVSSINRDGTTYYTPSVAGRFTMSQNNAKNTVYLQ
MNSLKPDDTAVYYCATDPAVGIVVRSTCRGPFGYWGQGTQVTVSS

SEQ ID NO.131
QVQLQESGGGSVQAGGSLRLSCTVSGNTDSMNLMGWFRQAPGKEREGVASIYTGSRTITYPDSVKGRFTISQDNAKNTVYLQ
MNSLKPEDTAMYYCAADYRARYGASLRTSAYTYWGQGTQVTVSS

SEQ ID NO.132
QVQLQESGGGSVQAGGSLRLSCTAPGFTSNTCAMAWYRQAPGKEREFVSSRSTVGTTGYADSVKGRFTISKDEAKDTVYLQ
MNSLKPEDTAKYFCKTYACRDCIGRYCRTAPDAWGQGTQVTVSS

SEQ ID NO.133
QVQLQESGGGSVQAGGSLKLSCVVSGYTWCRYDMSWYRQAPGKEREFVSVIDDNGSTNYADSVKGRFTISKDNGNTVTLQ
MTSLKPADTAMYYCQTGRYRSRLGYRCPSGDYWGLGTQVTVSS

SEQ ID NO.134
QVQLQESGGGSVQAGGSLRLSCAVSGYSISNYCMGWFRQPPGKEREGVANIDTWGVTSYTDSVKGRFTISKDNAKNTLYLQ
MNSLKPEDTALYYCARRQFVNCGTLAPVNYVNWGQGTQVTVSS

SEQ ID NO.135
QVQLQESGGGSVQAGGSLRLSCTASGFTFSTLAMSWVRQAPGKGLEWVSTISSTGGATYYADSVKGRFTISRDNAKNTLYLQL
NSLKPEDTAMYYCRRCTDIYCSNSARWTGQGTQVTVSS

SEQ ID NO.136
QVQLQESGGGLVQPGGSLRLSCTASGFTFSTLAMSWVRQAPGKGLEWVSTISSTGGATYYADSVKGRFTISRDNAKNTLYLQL
NSLKPEDTAMYYCRRCTDIYCSNSARWTGQGTQVTVSS

SEQ ID NO.137
QVQLQESGGGLVQPGGSLRLSCVASGFSFSSSGMSWVRQAPGKGLEWVSTISYNGGSTFYTDSVKGRFTISRDNAKNTLYLQL
NSLKTEDTAMYYCAKSGTPVLAPNSVRGQGTQVTVSS

SEQ ID NO.138
QVQLQESGGGSVQAGGSLRLSCVSSGYAYNRYYMAWFSQAPGKGREGVAAVYIGDGRPYYADSVKGRFTISLDSAKNTVYLQ
MNSLKPEDTAMYYCAAAPGPLSRNYWYTSANYDYWGQGTQVTVSS

SEQ ID NO.139
QVQLQESGGGSVQAGGSLRLSCVASGYTNCRYDMSWYRQAPGKEREFVSSIDSEGVARHADSVKGRFGISQDNAKSTLYLQ
MNSLKPEDTAVYYCKTDYITCRFGSWSDSTWGQGTQVTVSS

SEQ ID NO.140
QVQLQESGGGSVQAGGSLRLSCVASGYTNCRYDMSWYRQAPGKEREFVSSIDSEGVARHADSVKGRFGISQDNAKSTLYLQ
MNSLKPEDTAMYYCKMDYIRCRFGSWSESTWGQGTQVTVSS

SEQ ID NO.141
QVQLQESGGGSVQAGGSLRLSCTAPGFTSNTCAMAWFRQAPGKEREFVSSMSTVGSTRFADSVKGRFTISKDEAKDTVYLQ
MNSLKPEDTAMYFCKTYACRECTGRYCRTAPDAWGQGTQVTVSS

SEQ ID NO.142
QVQLQESGGGSVQTGGSLRLSCAVSRYSASNNVIKWMGWFRQAPGKEREGVAALYTSGGNTYYADSVKGRFTISRDYSENT
VSLQMNNLKPEDTGMYYCAATVGTVLAGPLSARKYNYWGQGTQVTVSS

SEQ ID NO.143
QVQLQESGGGSVQAGGSLRLSCTAPGFTSNTCAMAWYRQAPGKEREFVSSISTVRTTAYADSVKGRFTISKDEAKATVYLQM
NSLKPEDTAMYFCKSYACRDCIGRYCRTAPDAWGQGTQVTVSS

SEQ ID NO.144
QVQLQESGGGSVQAGQSLRLSCTASGYTDSRYCMGWFRQAPGKERERVTTIHTGTGITYYADSVKGRFSISQDNAQNTMYL
QMNSLEPEDTAMYYCATTDYVYSASASWCNGYGVFNNWGQGTQVTVSS

SEQ ID NO.145
QVQLQESGGGSVQAGGSLRLSCTAPGFTSNTCAMAWYRQAPGKEREFVSSRSTVGTTGYADSVKGRFTISKDEAKDTVYLQ
MNSLKPEDTAKYFCKTYACRDCIGRYCRTAPDAWGQGTQVTVSS

SEQ ID NO.146
QVQLQESGGGSVQAGGSLRLSCAVSRYSASNNVIKWMGWFRQAPGKEREGVAALYTSGGNTYYADSVKGRFTISRDYSENT

VSLQMNNLKPEDTGMYYCATTVGTVLAGPLSARKYNYWGQGTQVTVSS

SEQ ID NO.147
QVQLQESGGGSVQAGGSLRLSCAASGYTSRPNFMVWFRQAPGKEREAVAGIYTVTGGTLYSDPVKGRFTISQDKAKNTVYLQ

MNSLNPEDTAMYYCAVKWYGGSWSDAATFRTWGRGTQVTVSS

SEQ ID NO.148
QVQLQESGGGSVQAGGSLRLSCAASGYSYNIDYMAWFRQAPGKEREGVAAIYTGSRRTYYSDSVKGRFAISQDNADNTVYLQ

MNALKPEDTAMYFCAALVSRPGRSWDKNEYRYWGQGTQVTVSS

SEQ ID NO.149
QVQLQESGGGLVQAGGSLRLSCTASGFTFDDYSMGWFRQAPGKEREGISCIDWSGGRTNYGDSVKGRFTISRDNAKNTLYLQ

MNSLKPEDTAMYYCAANSAYSSCSLSTTHYKYWGQGTQVTVSS

SEQ ID NO.150
QVQLQESGGGLVQPGGSLRLSCAASGFTFSAYGMSWVRQAPGKGFEWVSTINSGGGTTFYADSVKGRFTISRDNAKNTLYLQ

LNSLRTEDTAMYYCRRCADIYCSLSGGWTGQGTQVTVSS

Combined with PE-LISA results, these VHH chains were classified into four categories according to the OD ratio (experimental group ($A_{405}$ nm)/control group ($A_{405}$ nm)), and the classification results are shown in Table 3.

TABLE 3

Affinity of nanobodies

| OD ratio (experimental group ($A_{405}$ nm)/ control group ($A_{405}$ nm)) | Nanobody |
| --- | --- |
| >20 | SEQ ID NO.: 1-86 |
| 10-20 | SEQ ID NO.: 87-118 |
| 6-10 | SEQ ID NO.: 119-138 |
| 3-6 | SEQ ID NO.: 139-150 |

It is worth noting that for any of the VHHs of SEQ ID NO.: 1-86, the ratio of the corresponding OD values is as high as 20 or more, suggesting that it has a very high affinity for binding to PD-L1.

Even for any of the VHHs of SEQ ID NO.: 139-150, the corresponding OD value ratio is still more than 3 times, suggesting that it has a good affinity for binding to PD-L1.

Example 4: Nanobody Expression and Purification in Host Strain *E. coli*

(1) For Example 3, different clones obtained by sequencing analysis (150 nanobodies in Table 2) were electrotransformed into *E. coli* WK6 and coated on LA+glucose, a culture plate with ampicillin and glucose, and incubate at 37° C. overnight;
(2) Single colonies were selected and inoculated in 5 mL of LB medium containing ampicillin and cultured overnight at 37° C. on a shaker;
(3) Inoculate 1 mL of the overnight strain into 330 mL TB medium, incubate at 37° C. on a shaker. Until the OD value reaches 0.6-1, add IPTG, and incubate at 28° C. overnight on a shaker;
(4) centrifugation, collection of colonies;
(5) obtaining a crude extract of the antibody by an infiltration method;
(6) preparing a purified nanobody by nickel column ion affinity chromatography.

The purification results showed that the prepared nanoantibodies were all more than 95% purity.

Figure 2:
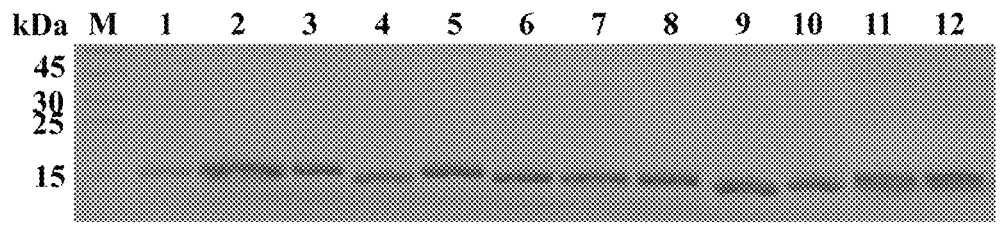
FIG. 2 is a purification map of 12 strains of anti-PD-L1 nanobodies. Lane M is a molecular weight standard, and lanes 1-12 correspond to nanobodies of SEQ ID NO.: 1-12 amino acid sequences, respectively.

Among them, the purification results of the 1-12th anti-PD-L1 nanobody (SEQ ID NO.: 1-12) are shown in FIG. 2. The figure was subjected to electrophoresis on SDS-PAGE of anti-PD-L1 nanobody after purification by nickel column resin gel affinity chromatography. The results showed that the anti-PD-L1 nanobody could achieve a purity of over 95% after the purification process.

Example 5: Enzyme-Linked Immunosorbent Assay (ELISA) was Used to Identify the Specificity of 12 Purified Nanobodies (1) Coated antigenic proteins PD-L1 and PD-L2: 0.5 μg per well (5 μg/mL, 100 μL), packaged NaHCO3 (100 mM, pH8.2) was used as a blank control and overnight at 4° C.
(2) Wash the cells three times with PBST the next day, add 200 μL of 1% BSA to block at room temperature for 2 hours.
(3) Each purified nanobody was diluted to 10 μg/mL, and 100 μL of each of the purified nanobodies was incubated with the coated PD-L1, PD-L2 and the blank control group, and reacted at room temperature for 1 hour.
(4) Unbound antibody was washed away with PBST, and 100 μL of mouse anti-HA tag antibody (1:2000 dilution) was added and placed at room temperature for 1 hour.
(5) Unbound antibody was washed away with PBST, and anti-mouse alkaline phosphatase conjugate (1:2000 dilution) was added and placed at room temperature for 1 hour.
(6) Wash the unbound antibody with PBST, add alkaline phosphatase coloring solution, and read the absorbance at 405 nm on an ELISA apparatus. The specificity of the nanobody was judged based on the absorption value.

The test results are shown in Table 4.

TABLE 4

Specificity of nanobodies

| | Nanobody incubation | Coating antigen | | | |
| --- | --- | --- | --- | --- | --- |
| | | PD-L1 | PD-L2 | Blank control | OD ratio |
| ELISA absorbance ($A_{405\ nm}$) | SEQ ID NO.: 1 | 3.803 | 0.118 | 0.116 | 32.2 |
| | SEQ ID NO.: 2 | 3.626 | 0.114 | 0.118 | 31.8 |
| | SEQ ID NO.: 3 | 2.356 | 0.112 | 0.119 | 21.0 |

TABLE 4-continued

Specificity of nanobodies

| Nanobody incubation | Coating antigen | | | OD ratio |
|---|---|---|---|---|
| | PD-L1 | PD-L2 | Blank control | |
| SEQ ID NO.: 4 | 3.512 | 0.137 | 0.124 | 25.6 |
| SEQ ID NO.: 5 | 3.376 | 0.128 | 0.138 | 26.4 |
| SEQ ID NO.: 6 | 3.437 | 0.115 | 0.129 | 29.9 |
| SEQ ID NO.: 7 | 3.506 | 0.119 | 0.131 | 29.5 |
| SEQ ID NO.: 8 | 3.371 | 0.133 | 0.110 | 25.3 |
| SEQ ID NO.: 9 | 3.558 | 0.131 | 0.119 | 27.2 |
| SEQ ID NO.: 10 | 3.342 | 0.117 | 0.126 | 28.6 |
| SEQ ID NO.: 11 | 2.895 | 0.116 | 0.120 | 25.0 |
| SEQ ID NO.: 12 | 2.987 | 0.125 | 0.117 | 23.9 |

The results in Table 4 show that the nanobodies of the invention have very high specificity, and their selectivity for PD-L1 is very high, and the ratio of OD values (PD-L1/PD-L2) is as high as 21-35.

In addition, the specificity of the PD-L1 nanobody was detected by flow cytometry. The PD-L1 full-length gene and the PD-L2 full-length gene were transiently transfected in a conventional 293F cell, and a nano-antibody (SEQ ID NO.: 1) of PD-L1 was selected for incubation for flow cytometry. Nanobody (SEQ ID NO.: 1) is 55% positive for PD-L1 transient cells, 0.1% for PD-L2 transient cells, and the difference is at least about 550 times, which further suggests the inventive nanobody has a very superior specificity for PD-L1.

All documents mentioned in the present application are hereby incorporated by reference in (heir entireties as if the disclosures in. In addition, it is to be understood that various modifications and changes may be made by those skilled in the field of the invention after reading the contents, in the form of the appended claims. These equivalent forms also apply for the scope defined by the appended claims.

What is claimed is:

1. A VHH chain of an anti-PD-L1 nanobody, wherein the amino acid sequence of the VHH chain comprises any one of SEQ ID NOs.: 2-8, 10-11, 13-17, 19, 21-44, 46-49, 51-62, 64-69, 71-73, 75-150.

2. The VIM chain of an anti-PD-L1 nanobody according to claim 1, wherein the amino acid sequence of the chain comprises SEQ ID NOs.: 2-8, 10 or 11.

3. The VHH chain of an anti-PD-L1 nanobody according to claim 1, wherein the amino acid sequence of the chain comprises any one of SEQ ID NOs.: 3-5, 7, 13-17, 19, 21-23, 25-26, 28-33, 36-39, 41-44, 46-49, 51-57, 59-60, 62, 64, 66, 68-69, 75-76, 78, 80-81, 83, 85-86, 88-90, 92-95, 97-99, 101-104, 108, 113, 117-119, and 123.

4. The chain of an anti-PD-L1 nanobody according to claim 1, wherein the amino acid sequence of the VHH chain comprises any one of SEQ ID NOs.: 58 and 61.

5. The VHH chain of an anti-PD-L1 nanobody according to claim 1, which has a very high specificity or selectivity for PD-L1 (relative to PD-L2) and has a selectivity ratio (such as a ratio of OD value)(PD-L1/PD-L2) as high as ≥20.

6. An immunoconjugate, wherein the immunoconjugate comprises:
   (a) the VIM chain of the anti-PD-L1 nanobody according to claim 1; and
   (b) a conjugating part selected from the group consisting of a detectable marker, drug, toxin, cytokine, radionuclide, and enzyme.

7. A pharmaceutical composition comprising:
   (i) the VHH chain of the anti-PD-L1 nanobody according to claim 1, or an immunoconjugate comprising the chain of the anti-PD-L1 nanobody; and
   (ii) a pharmaceutically acceptable carrier.

8. The pharmaceutical composition according to claim 7, wherein the amino acid sequence of the VHH chain comprises SEQ ID NOs.: 9 or 18.

* * * * *

SEQUENCE LISTING

```
<160> NUMBER OF SEQ ID NOS: 300

<210> SEQ ID NO 1
<211> LENGTH: 127
<212> TYPE: PRT
<213> ORGANISM: Camelus bactrianus

<400> SEQUENCE: 1

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ser Pro Gly Lys Gly Arg Glu Gly Val
        35                  40                  45

Ala Ala Val Tyr Met Asp Asp Gly Arg Pro Tyr Tyr Ala Asp Ser Val
    50                  55                  60

Lys Gly Arg Phe Thr Ile Ser Leu Asp Ser Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 2
<211> LENGTH: 129
<212> TYPE: PRT
<213> ORGANISM: Camelus bactrianus

<400> SEQUENCE: 2

Gln Val Gln Leu Gln Glu Ser Gly Gly Gly Ser Val Gln Ala Gly Gly
1               5                   10                  15

Ser Leu Arg Leu Ser Cys Ala Val Ser Arg Tyr Ser Ala Ser Asn Asn
            20                  25                  30

Val Ile Lys Trp Met Gly Trp Phe Arg Gln Ala Pro Gly Lys Glu Arg
        35                  40                  45

Glu Gly Val Ala Ala Leu Tyr Thr Ser Gly Gly Asn Thr Tyr Tyr Ala
    50                  55                  60
```

```
Asp Ser Val Lys Gly Arg Phe Thr Ile Ser Arg Asp Tyr Ser Glu Asn
 65                  70                  75                  80

Thr Val Ser Leu Gln Met Asn Asn Leu Lys Pro Glu Asp Thr Gly Met
             85                  90                  95

Tyr Tyr Cys Ala Thr Thr Val Gly Thr Val Leu Ala Gly Pro Leu Ser
        100                 105                 110

Ala Arg Lys Tyr Asn Tyr Trp Gly Gln Gly Thr Gln Val Thr Val Ser
        115                 120                 125

Ser

<210> SEQ ID NO 3
<211> LENGTH: 127
<212> TYPE: PRT
<213> ORGANISM: Camelus bactrianus

<400> SEQUENCE: 3

Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Leu Tyr Ser Tyr Asn
             20                  25                  30

Tyr Met Ala Trp Phe Ser Gln Ala Pro Gly Lys Gly Arg Glu Gly Val
         35                  40                  45

Ala Ala Val Tyr Val Gly Asp Gly Arg Pro Tyr Tyr Ala Asp Ser Val
     50                  55                  60

Lys Gly Arg Phe Thr Ile Ser Leu Asp Ser Ala Lys Asn Ala Val Tyr
 65                  70                  75                  80

Leu Gln Met Asn Ser Leu Lys Pro Glu Asp Thr Ala Met Tyr Tyr Cys
             85                  90                  95

Ala Ala Ala Pro Gly Pro Leu Ser His Asn Tyr Trp Tyr Thr Ser Ala
        100                 105                 110

Asn Tyr Asp Tyr Trp Gly Gln Gly Thr Gln Val Thr Val Ser Ser
        115                 120                 125

<210> SEQ ID NO 4
<211> LENGTH: 127
<212> TYPE: PRT
<213> ORGANISM: Camelus bactrianus

<400> SEQUENCE: 4

Gln Val Gln Leu Gln Glu Ser Gly Gly Gly Ser Val Gln Thr Gly Gly
 1               5                  10                  15

Ser Leu Arg Leu Ser Cys Ala Ala Ser Pro Ser Ile Tyr Ser Ala Asn
             20                  25                  30

Tyr Met Ala Trp Phe Ser Gln Ala Pro Gly Lys Gly Arg Glu Gly Val
         35                  40                  45

Ala Ala Val Tyr Ile Gly Asp Gly Arg Pro Tyr Tyr Ala Asp Ser Val
     50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
             85                  90                  95

Ala Ala Ala Pro Gly Pro Leu Gly His Asn Tyr Trp Tyr Thr Ser Ala
        100                 105                 110

Asn Tyr Asp Tyr Trp Gly Gln Gly Thr Gln Val Thr Val Ser Ser
        115                 120                 125
```

<210> SEQ ID NO 5
<211> LENGTH: 127
<212> TYPE: PRT
<213> ORGANISM: Camelus bactrianus

<400> SEQUENCE: 5

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Gly Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 6
<211> LENGTH: 126
<212> TYPE: PRT
<213> ORGANISM: Camelus bactrianus

<400> SEQUENCE: 6

Gln Val Gln Leu Gln Glu Ser Gly Gly Gly Ser Val Gln Ala Gly Glu
1               5                   10                  15

Thr Leu Arg Leu Ser Cys Thr Ala Ser Gly Asp Thr Phe Asp Ala Ser
            20                  25                  30

Gly Val Gly Trp Phe Arg Gln Val Ser Gly Asn Glu Cys Asp Leu Val
        35                  40                  45

Ser Ser Ile Asn Arg Asp Gly Thr Thr Tyr Tyr Ala Pro Ser Val Ala
    50                  55                  60

Gly Arg Phe Thr Met Ser Gln Asn Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

Thr Asp Pro Ala Val Gly Ile Val Val Arg Ser Thr Cys Arg Gly Pro
            100                 105                 110

Phe Gly Tyr Trp Gly Gln Gly Thr Gln Val Thr Val Ser Ser
        115                 120                 125

<210> SEQ ID NO 7
<211> LENGTH: 127
<212> TYPE: PRT
<213> ORGANISM: Camelus bactrianus

<400> SEQUENCE: 7

Gln Val Gln Leu Gln Glu Ser Gly Gly Gly Ser Val Gln Thr Gly Gly
1               5                   10                  15

Ser Leu Arg Leu Ser Cys Ala Cys Ser Thr Ser Ile Tyr Ser Thr Asn
            20                  25                  30

Tyr Met Ala Trp Phe Ser Gln Ala Pro Gly Lys Gly Arg Glu Gly Val 35                  40                  45
Ala Ala Val Tyr Ile Gly Asp Gly Arg Pro Tyr Tyr Ala Asp Ser Val
        50                  55                  60

Lys Gly Arg Phe Thr Ile Ser Leu Asp Ser Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 8
<211> LENGTH: 125
<212> TYPE: PRT
<213> ORGANISM: Camelus bactrianus

<400> SEQUENCE: 8

Gln Val Gln Leu Gln Glu Ser Gly Gly Asp Ser Val Gln Ala Gly Gly
 1               5                  10                  15

Ser Leu Arg Leu Ala Cys Lys Val Pro Gly Phe Thr Ser Asn Thr Cys
            20                  25                  30

Ala Met Ala Trp Phe Arg Gln Ala Pro Gly Lys Glu Arg Glu Phe Val
        35                  40                  45

Ser Ser Ile Ser Thr Gly Gly Thr Gly Tyr Ala Glu Ser Ala Lys
    50                  55                  60

Gly Arg Phe Thr Leu Ser Lys Asp Glu Ala Lys Asp Thr Val Tyr Leu
 65                  70                  75                  80

Gln Met Asn Ser Leu Lys Pro Glu Asp Thr Ala Met Tyr Phe Cys Lys
                85                  90                  95

Ser Tyr Ala Cys Arg Thr Cys Ile Gly Arg Tyr Cys Arg Thr Ala Pro
            100                 105                 110

Asp Ala Trp Gly Gln Gly Thr Gln Val Thr Val Ser Ser
        115                 120                 125

<210> SEQ ID NO 9
<211> LENGTH: 124
<212> TYPE: PRT
<213> ORGANISM: Camelus bactrianus

<400> SEQUENCE: 9

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Tyr Thr Tyr Ser Asn Asp
            20                  25                  30

Gly Met Gly Trp Phe Arg Gln Ile Pro Gly Lys Glu Arg Glu Gly Val
        35                  40                  45

Ala Ala Ile Ser Pro Thr Gly Arg Thr Glu Tyr Ala Asp Ser Val
    50                  55                  60

Gln Gly Arg Phe Thr Ile Ser Arg Asp Asn Ala Lys Asn Met Leu Ser
 65                  70                  75                  80

Leu Gln Met Asn Ser Leu Lys Pro Glu Asp Thr Gly Met Tyr Tyr Cys
                85                  90                  95

Ala Arg Glu Gly Ser Gly Ser Phe Ser Leu Gln Asn Ser Ala Val Arg
            100                 105                 110

Ser Trp Gly Gln Gly Thr Gln Val Thr Val Ser Ser

-continued

```
                115                 120

<210> SEQ ID NO 10
<211> LENGTH: 125
<212> TYPE: PRT
<213> ORGANISM: Camelus bactrianus

<400> SEQUENCE: 10

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Lys Thr Cys
            20                  25                  30

Ala Met Arg Trp Tyr Arg Gln Ala Pro Gly Lys Glu Arg Glu Phe Val
        35                  40                  45

Ser Ala Ile Ser Thr Val Gly Thr Thr Thr Tyr Ala Asp Ser Val Lys
    50                  55                  60

Gly Arg Phe Ile Ile Ser Lys Asp Glu Ala Lys Asp Thr Val Tyr Leu
65                  70                  75                  80

Gln Ile Asn Ser Leu Lys Pro Glu Asp Thr Ala Met Tyr Ser Cys Lys
                85                  90                  95

Thr Phe Ala Cys Arg His Cys Ile Gly Gln Ser Cys Arg Thr Glu Pro
            100                 105                 110

Asp Tyr Trp Gly Gln Gly Thr Gln Val Thr Val Ser Ser
        115                 120                 125

<210> SEQ ID NO 11
<211> LENGTH: 126
<212> TYPE: PRT
<213> ORGANISM: Camelus bactrianus

<400> SEQUENCE: 11

Gln Val Gln Leu Gln Glu Ser Gly Gly Gly Ser Val Gln Ala Gly Glu
1               5                   10                  15

Thr Leu Arg Leu Ser Cys Thr Ala Ser Gly Asp Thr Phe Asp Asp Ser
            20                  25                  30

Gly Val Gly Trp Phe Arg Gln Val Ser Gly Asn Glu Cys Asp Leu Val
        35                  40                  45

Ser Ser Ile Asn Arg Asp Gly Thr Thr Tyr Tyr Ala Pro Ser Val Ala
    50                  55                  60

Gly Arg Phe Thr Ile Ser Gln Asn Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

Thr Val Pro Ala Val Gly Ile Val Val Arg Ile Thr Cys Arg Gly Pro
            100                 105                 110

Phe Gly Tyr Trp Gly Gln Gly Thr Gln Val Thr Val Ser Ser
        115                 120                 125

<210> SEQ ID NO 12
<211> LENGTH: 127
<212> TYPE: PRT
<213> ORGANISM: Camelus bactrianus

<400> SEQUENCE: 12

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Arg Ser Ser His
            20                  25                  30
```

Cys Met Val Trp Phe Arg Gln Ala Pro Gly Lys Glu Arg Glu Gly Val
                35                  40                  45

Ala Leu Ile Tyr Thr Gly Ser Gly Ser Thr Tyr Tyr Ala Asp Ser Val
         50                  55                  60

Lys Gly Arg Phe Thr Ile Ser Gln Asp Asn Ala Lys Lys Thr Leu Tyr
 65                  70                  75                  80

Leu Gln Met Asn Ser Leu Lys Pro Glu Asp Thr Ala Met Tyr Tyr Cys
                 85                  90                  95

Ala Ala Gly Thr Ser Ser Ser Cys Pro Gly Leu Leu Gly Pro Pro
                100                 105                 110

Arg Tyr Tyr Asn Trp Gly Gln Gly Thr Gln Val Thr Val Ser Ser
            115                 120                 125

<210> SEQ ID NO 13
<211> LENGTH: 127
<212> TYPE: PRT
<213> ORGANISM: Camelus bactrianus

<400> SEQUENCE: 13

Gln Val Gln Leu Gln Glu Ser Gly Gly Gly Ser Val Gln Thr Gly Gly
  1               5                  10                  15

Ser Leu Arg Leu Ser Cys Ala Ala Ser Thr Ser Ile Tyr Ser Asn Asn
                 20                  25                  30

Tyr Met Ala Trp Phe Ser Gln Asn Pro Gly Lys Gly Arg Glu Gly Val
                 35                  40                  45

Ala Ala Val Tyr Ile Gly Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
                100                 105                 110

Asn Tyr Asp Tyr Trp Gly Gln Gly Thr Gln Val Thr Val Ser Ser
            115                 120                 125

<210> SEQ ID NO 14
<211> LENGTH: 127
<212> TYPE: PRT
<213> ORGANISM: Camelus bactrianus

<400> SEQUENCE: 14

Gln Val Gln Leu Gln Glu Ser Gly Gly Gly Ser Val Gln Thr Gly Gly
  1               5                  10                  15

Ser Leu Arg Leu Ser Cys Ala Ala Ser Thr Ser Ile Tyr Ser Asn Asn
                 20                  25                  30

Tyr Met Ala Trp Phe Ser Gln Ala Pro Gly Lys Gly Arg Glu Gly Val
                 35                  40                  45

Ala Ala Val Tyr Ile Asp Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Val Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
                100                 105                 110

```
Asn Tyr Asp Tyr Trp Gly Gln Gly Thr Gln Val Thr Val Ser Ser
            115                 120                 125

<210> SEQ ID NO 15
<211> LENGTH: 127
<212> TYPE: PRT
<213> ORGANISM: Camelus bactrianus

<400> SEQUENCE: 15

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Thr Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Tyr Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 16
<211> LENGTH: 127
<212> TYPE: PRT
<213> ORGANISM: Camelus bactrianus

<400> SEQUENCE: 16

Gln Val Gln Leu Gln Glu Ser Gly Gly Gly Ser Val Gln Thr Gly Gly
1               5                   10                  15

Ser Leu Arg Leu Ser Cys Ala Ala Ser Pro Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Gly Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 17
<211> LENGTH: 127
<212> TYPE: PRT
<213> ORGANISM: Camelus bactrianus

<400> SEQUENCE: 17

Gln Val Gln Leu Gln Glu Ser Gly Gly Gly Ser Val Gln Thr Gly Gly
1               5                   10                  15
```

Ser Leu Arg Leu Ser Cys Ala Ala Ser Thr Ser Ile Tyr Ser Leu Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp His Val
 50                  55                  60

Lys Gly Arg Phe Thr Ile Ser Leu Asp Thr Ala Lys Asn Thr Val Tyr
65                   70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 18
<211> LENGTH: 124
<212> TYPE: PRT
<213> ORGANISM: Camelus bactrianus

<400> SEQUENCE: 18

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Asp
            20                  25                  30

Gly Met Gly Trp Phe Arg Gln Thr Pro Gly Lys Glu Arg Glu Gly Val
            35                  40                  45

Ala Ala Ile Ser Pro Thr Gly Arg Arg Thr Glu Tyr Ala Asp Ser Val
 50                  55                  60

Lys Gly Arg Phe Thr Ile Ser Arg Asp Asn Asn Lys Asn Met Leu Ser
65                   70                  75                  80

Leu Gln Met Asn Ser Leu Lys Pro Glu Asp Thr Gly Met Tyr Tyr Cys
            85                  90                  95

Ala Arg Glu Gly Ser Trp Ser Phe Ser Leu Ala Asn Ser Ala Val Arg
            100                 105                 110

Ser Trp Gly Gln Gly Thr Gln Val Thr Val Ser Ser
            115                 120

<210> SEQ ID NO 19
<211> LENGTH: 127
<212> TYPE: PRT
<213> ORGANISM: Camelus bactrianus

<400> SEQUENCE: 19

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Gly Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
65                   70                  75                  80

Leu Gln Met Asn Ser Leu Lys Pro Glu Asp Thr Ala Met Tyr Tyr Cys
            85                  90                  95

```
Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 20
<211> LENGTH: 121
<212> TYPE: PRT
<213> ORGANISM: Camelus bactrianus

<400> SEQUENCE: 20

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Gly Ser Ile Tyr
            20                  25                  30

Ala Met Ser Trp Val Arg Gln Ala Pro Gly Lys Gly Leu Glu Trp Val
        35                  40                  45

Ser Thr Ile Ser Ser Ser Gly Gly Arg Arg Phe Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Lys Thr Glu Asp Thr Ala Met Tyr Tyr Cys
                85                  90                  95

Ala Arg Cys Ser Asp Ile Tyr Cys Asp Asn Gly Ala Ser Tyr Arg Gly
            100                 105                 110

Gln Gly Thr Gln Val Thr Val Ser Ser
        115                 120

<210> SEQ ID NO 21
<211> LENGTH: 127
<212> TYPE: PRT
<213> ORGANISM: Camelus bactrianus

<400> SEQUENCE: 21

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Leu Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Ser Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 22
<211> LENGTH: 127
<212> TYPE: PRT
<213> ORGANISM: Camelus bactrianus

<400> SEQUENCE: 22

Gln Val Gln Leu Gln Glu Ser Gly Gly Gly Ser Val Gln Thr Gly Gly
```

-continued

```
                1               5                   10                  15
            Ser Leu Arg Leu Ser Cys Ala Ala Ser Thr Ser Ile Tyr Ser Asn Asn
                        20                  25                  30

Tyr Met Ala Trp Phe Ser Gln Ala Pro Arg Lys Gly Arg Glu Gly Val
                        35                  40                  45

Ala Ala Val Tyr Ile Gly Asp Gly Arg Pro Tyr Tyr Ala Asp Ser Val
                        50                  55                  60

Lys Gly Arg Phe Thr Ile Ser Leu Asp Ser Ala Lys Asn Thr Val Tyr
            65                  70                  75                  80

Leu Gln Met Asn Ser Leu Lys Pro Glu Asp Thr Ala Met Tyr Tyr Cys
                        85                  90                  95

Ala Ala Ala Pro Gly Pro Leu Ser His Asn Tyr Trp Tyr Thr Ser Ala
                        100                 105                 110

Asn Tyr Asp Tyr Trp Gly Gln Gly Thr Gln Val Thr Val Ser Ser
                        115                 120                 125
```

<210> SEQ ID NO 23
<211> LENGTH: 127
<212> TYPE: PRT
<213> ORGANISM: Camelus bactrianus

<400> SEQUENCE: 23

```
            Gln Val Gln Leu Gln Glu Ser Gly Gly Gly Ser Val Gln Thr Gly Gly
            1                   5                   10                  15

Ser Leu Arg Leu Ser Cys Ala Ala Ser Thr Ser Leu Tyr Ser Tyr Asn
                        20                  25                  30

Tyr Met Ala Trp Phe Ser Gln Ala Pro Gly Lys Gly Arg Glu Gly Val
                        35                  40                  45

Ala Ala Val Tyr Val Gly Asp Gly Arg Pro Tyr Tyr Ala Asp Ser Val
                        50                  55                  60

Lys Gly Arg Phe Thr Ile Ser Leu Asp Ser Ala Lys Asn Thr Val Tyr
            65                  70                  75                  80

Leu Gln Met Asn Ser Leu Lys Pro Glu Asp Thr Ala Met Tyr Tyr Cys
                        85                  90                  95

Ala Ala Ala Pro Gly Pro Leu Ser His Asn Tyr Trp Tyr Thr Ser Ala
                        100                 105                 110

Asn Tyr Asp Tyr Trp Gly Gln Gly Thr Gln Val Thr Val Ser Ser
                        115                 120                 125
```

<210> SEQ ID NO 24
<211> LENGTH: 127
<212> TYPE: PRT
<213> ORGANISM: Camelus bactrianus

<400> SEQUENCE: 24

```
            Gln Val Gln Leu Gln Glu Ser Gly Gly Gly Ser Val Gln Thr Gly Gly
            1                   5                   10                  15

Ser Leu Arg Leu Ser Cys Thr Ala Ser Thr Ser Ile Tyr Ser Asn Asn
                        20                  25                  30

Tyr Met Ala Trp Phe Ser Gln Ser Pro Gly Lys Gly Arg Glu Gly Val
                        35                  40                  45

Ala Ala Val Tyr Met Asp Asp Gly Arg Pro Tyr Tyr Ala Asp Ser Val
                        50                  55                  60

Lys Gly Arg Phe Thr Ile Ser Leu Asp Ser Ala Lys Asn Thr Met Tyr
            65                  70                  75                  80

Leu Gln Met Asn Ser Leu Lys Pro Glu Asp Thr Ala Met Tyr Tyr Cys
```

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 25
<211> LENGTH: 127
<212> TYPE: PRT
<213> ORGANISM: Camelus bactrianus

<400> SEQUENCE: 25

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 26
<211> LENGTH: 127
<212> TYPE: PRT
<213> ORGANISM: Camelus bactrianus

<400> SEQUENCE: 26

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Asn Asn Asn
            20                  25                  30

Tyr Met Ala Trp Phe Ser Gln Ala Pro Gly Lys Glu Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 27
<211> LENGTH: 127
<212> TYPE: PRT
<213> ORGANISM: Camelus bactrianus

<400> SEQUENCE: 27

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ser Pro Gly Lys Gly Arg Glu Gly Val
        35                  40                  45

Ala Ala Val Tyr Met Asp Asp Gly Arg Pro Tyr Tyr Ala Asp Ser Val
    50                  55                  60

Lys Gly Arg Phe Thr Ile Ser Leu Asp Ser Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 28
<211> LENGTH: 127
<212> TYPE: PRT
<213> ORGANISM: Camelus bactrianus

<400> SEQUENCE: 28

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125

<210> SEQ ID NO 29
<211> LENGTH: 127
<212> TYPE: PRT
<213> ORGANISM: Camelus bactrianus

<400> SEQUENCE: 29

Gln Val Gln Leu Gln Glu Ser Gly Gly Gly Ser Val Arg Thr Gly Gly
1               5                   10                  15

Ser Leu Arg Leu Ser Cys Ala Ala Ser Pro Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

```
Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 30
<211> LENGTH: 127
<212> TYPE: PRT
<213> ORGANISM: Camelus bactrianus

<400> SEQUENCE: 30

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 31
<211> LENGTH: 127
<212> TYPE: PRT
<213> ORGANISM: Camelus bactrianus

<400> SEQUENCE: 31

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
            35                  40                  45

Ala Gly Val Tyr Ile Gly Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His His Tyr Trp Tyr Thr Ser Ala
            100                 105                 110

Asn Tyr Asp Tyr Trp Gly Pro Gly Thr Gln Val Thr Val Ser Ser
        115                 120                 125

<210> SEQ ID NO 32
<211> LENGTH: 127
<212> TYPE: PRT
<213> ORGANISM: Camelus bactrianus
```

<400> SEQUENCE: 32

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Ile Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Gln His Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 33
<211> LENGTH: 127
<212> TYPE: PRT
<213> ORGANISM: Camelus bactrianus

<400> SEQUENCE: 33

Gln Val Gln Leu Gln Glu Ser Gly Gly Gly Ser Val Gln Thr Gly Gly
1               5                   10                  15

Ser Leu Arg Leu Ser Cys Ala Cys Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Gln His Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 34
<211> LENGTH: 127
<212> TYPE: PRT
<213> ORGANISM: Camelus bactrianus

<400> SEQUENCE: 34

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Arg Ser Leu Tyr
            20                  25                  30

Cys Met Gly Trp Phe Arg Gln Ala Pro Gly Arg Glu Arg Glu Gly Val
        35                  40                  45

Ala His Val Tyr Thr Gly Asp Gly Ser Pro Tyr Tyr Ala Asp Ser Val
    50                  55                  60

Lys Gly Arg Phe Thr Ile Ser Gln Asp Asn Gly Glu Ser Thr Leu Tyr
65                  70                  75                  80

Leu Gln Met Asn Asn Leu Lys Pro Glu Asp Thr Ala Met Tyr Tyr Cys
                85                  90                  95

Ala Ala Gly Thr Ser Ala Leu Ser Arg Pro Tyr Gly Pro Ile Ser Tyr
            100                 105                 110

Gly Tyr Trp Tyr Trp Gly Gln Gly Thr Gln Val Thr Val Ser Ser
            115                 120                 125

<210> SEQ ID NO 35
<211> LENGTH: 127
<212> TYPE: PRT
<213> ORGANISM: Camelus bactrianus

<400> SEQUENCE: 35

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 36
<211> LENGTH: 127
<212> TYPE: PRT
<213> ORGANISM: Camelus bactrianus

<400> SEQUENCE: 36

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Leu Tyr Ser Tyr Asn
            20                  25                  30

Tyr Met Ala Trp Phe Ser Gln Ala Pro Gly Lys Gly Arg Glu Gly Val
            35                  40                  45

Ala Ala Val Tyr Val Gly Asp Gly Arg Pro Tyr Tyr Ala Ala Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 37
<211> LENGTH: 127

```
<212> TYPE: PRT
<213> ORGANISM: Camelus bactrianus

<400> SEQUENCE: 37

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Ile Asn
            20                  25                  30

Tyr Met Ala Trp Phe Arg Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Thr Ser Leu Lys Ser Glu Asp Thr Ala Met Tyr Tyr Cys
                85                  90                  95

Ala Ala Ala Pro Gly Pro Leu Ser Arg Ser Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 38
<211> LENGTH: 127
<212> TYPE: PRT
<213> ORGANISM: Camelus bactrianus

<400> SEQUENCE: 38

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Ala
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 39
<211> LENGTH: 127
<212> TYPE: PRT
<213> ORGANISM: Camelus bactrianus

<400> SEQUENCE: 39

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Leu Tyr Ile Gly Asp Gly Arg Pro Tyr Tyr Ala Asp Ser Val
```

```
                50                  55                  60
Lys Gly Arg Phe Thr Ile Ala Leu Asp Ser Ala Lys Asn Thr Val Tyr
 65                  70                  75                  80

Leu Gln Met Asn Gly Leu Lys Pro Glu Asp Thr Ala Met Tyr Tyr Cys
                 85                  90                  95

Ala Ala Ala Pro Gly Pro Leu Lys His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 40
<211> LENGTH: 127
<212> TYPE: PRT
<213> ORGANISM: Camelus bactrianus

<400> SEQUENCE: 40

Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Ile Tyr Ser Asn Asn
             20                  25                  30

Tyr Met Ala Trp Phe Ser Gln Ala Pro Gly Lys Gly Arg Glu Gly Val
         35                  40                  45

Ala Ala Leu Tyr Ile Gly Asp Gly Arg Pro Tyr Tyr Ala Asp Ser Val
     50                  55                  60

Lys Gly Arg Phe Thr Ile Ala Leu Asp Ser Ala Lys Asn Thr Val Tyr
 65                  70                  75                  80

Leu Gln Met Asn Gly Leu Lys Pro Glu Asp Thr Ala Met Tyr Tyr Cys
                 85                  90                  95

Ala Ala Ala Pro Gly Pro Leu Lys His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 41
<211> LENGTH: 127
<212> TYPE: PRT
<213> ORGANISM: Camelus bactrianus

<400> SEQUENCE: 41

Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Ile Tyr Ser Asn Asn
             20                  25                  30

Tyr Met Ala Trp Phe Arg Gln Ala Pro Gly Lys Gly Arg Glu Gly Val
         35                  40                  45

Ala Ala Val Tyr Ile Gly Asp Gly Arg Pro Tyr Tyr Ala Asp Ser Ala
     50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125
```

```
<210> SEQ ID NO 42
<211> LENGTH: 127
<212> TYPE: PRT
<213> ORGANISM: Camelus bactrianus

<400> SEQUENCE: 42

Gln Val Gln Leu Gln Glu Ser Gly Gly Gly Ser Val Gln Thr Gly Gly
1               5                   10                  15

Ser Leu Thr Leu Ser Cys Ala Ala Ser Thr Ser Ile Tyr Ser Tyr Asn
            20                  25                  30

Tyr Met Ala Trp Phe Arg Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Pro Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125

<210> SEQ ID NO 43
<211> LENGTH: 127
<212> TYPE: PRT
<213> ORGANISM: Camelus bactrianus

<400> SEQUENCE: 43

Gln Val Gln Leu Gln Glu Ser Gly Gly Gly Ser Val Gln Thr Gly Gly
1               5                   10                  15

Ser Leu Arg Leu Ser Cys Ala Ala Ser Ser Ile Ala Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 44
<211> LENGTH: 127
<212> TYPE: PRT
<213> ORGANISM: Camelus bactrianus

<400> SEQUENCE: 44

Gln Val Gln Leu Gln Glu Ser Gly Gly Gly Ser Val Arg Thr Gly Gly
1               5                   10                  15

Ser Leu Arg Leu Ser Cys Ala Ala Ser Thr Ser Ile Tyr Ser Leu Asn
            20                  25                  30

Tyr Met Ala Trp Phe Ser Gln Ala Pro Gly Lys Gly Arg Glu Gly Val
        35                  40                  45
```

```
Ala Ala Val Tyr Ile Asp Asp Gly Arg Pro Tyr Tyr Ala Asp His Val
         50                  55                  60

Lys Gly Arg Phe Thr Ile Ser Leu Asp Thr Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 45
<211> LENGTH: 121
<212> TYPE: PRT
<213> ORGANISM: Camelus bactrianus

<400> SEQUENCE: 45

Gln Val Gln Leu Gln Glu Ser Gly Gly Gly Leu Val Gln Pro Gly Gly
 1                   5                  10                  15

Ser Leu Arg Leu Ser Cys Ala Ala Ser Gly Phe Thr Phe Ser Ile Lys
                 20                  25                  30

Ala Met Ser Trp Val Arg Gln Ala Pro Gly Lys Gly Leu Glu Trp Val
             35                  40                  45

Ser Thr Ile Asp Ser Gly Gly Gly Arg Arg Tyr Tyr Ala Asp Ser Val
         50                  55                  60

Lys Gly Arg Phe Thr Ile Ser Arg Asp Asn Ala Lys Asn Thr Leu Tyr
 65                  70                  75                  80

Leu Gln Leu Ser Ser Leu Lys Thr Glu Asp Thr Ala Met Tyr Phe Cys
                 85                  90                  95

Ala Arg Cys Ser Asp Ile Tyr Cys Tyr Asn Gly Ala Ser Tyr Arg Gly
            100                 105                 110

Gln Gly Thr Gln Val Thr Val Ser Ser
            115                 120

<210> SEQ ID NO 46
<211> LENGTH: 127
<212> TYPE: PRT
<213> ORGANISM: Camelus bactrianus

<400> SEQUENCE: 46

Gln Val Gln Leu Gln Glu Ser Gly Gly Gly Ser Val Gln Thr Gly Gly
 1                   5                  10                  15

Ser Leu Arg Leu Ser Cys Ala Ala Ser Thr Ser Ile Asp Ser Asn Asn
                 20                  25                  30

Tyr Met Ala Trp Phe Arg Gln Ala Pro Gly Lys Gly Glu Gly Val
             35                  40                  45

Ala Ala Val Tyr Ile Asp Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
            115                 120                 125
```

<210> SEQ ID NO 47
<211> LENGTH: 127
<212> TYPE: PRT
<213> ORGANISM: Camelus bactrianus

<400> SEQUENCE: 47

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Asn Asn Asn
            20                  25                  30

Tyr Met Ala Trp Phe Ser Gln Ser Pro Gly Lys Gly Arg Glu Gly Val
        35                  40                  45

Ala Ala Val Tyr Met Asp Asp Gly Arg Pro Tyr Tyr Ala Asp Ser Val
    50                  55                  60

Lys Gly Arg Phe Thr Ile Ser Leu Asp Ser Ala Lys Asn Thr Met Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg Asn Tyr Trp Tyr Thr Ser Ala
        100                 105                 110

Asn Tyr Asp Tyr Trp Gly Gln Gly Thr Gln Val Thr Val Ser Ser
        115                 120                 125

<210> SEQ ID NO 48
<211> LENGTH: 127
<212> TYPE: PRT
<213> ORGANISM: Camelus bactrianus

<400> SEQUENCE: 48

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Thr Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser His Asn Tyr Trp Tyr Ala Ser Ala
        100                 105                 110

Asn Tyr Asp Tyr Trp Gly Gln Gly Thr Gln Val Thr Val Ser Ser
        115                 120                 125

<210> SEQ ID NO 49
<211> LENGTH: 127
<212> TYPE: PRT
<213> ORGANISM: Camelus bactrianus

<400> SEQUENCE: 49

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Ile Asn
            20                  25                  30

```
Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
 50                      55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125
```

<210> SEQ ID NO 50
<211> LENGTH: 121
<212> TYPE: PRT
<213> ORGANISM: Camelus bactrianus

<400> SEQUENCE: 50

```
Gln Val Gln Leu Gln Glu Ser Gly Gly Gly Leu Val Gln Pro Gly Gly
 1               5                  10                  15

Ser Leu Arg Leu Ser Cys Ile Ala Ser Gly Phe Thr Phe Ser Ile Met
            20                  25                  30

Ala Met Ser Trp Val Arg Gln Ala Pro Gly Lys Gly Leu Glu Trp Val
            35                  40                  45

Ser Thr Ile Asn Ser Asp Gly Gly Lys Thr Tyr Tyr Ala Asp Ser Val
 50                      55                  60

Lys Gly Arg Phe Thr Ile Ser Arg Asp Asn Ala Lys Asn Thr Leu Tyr
 65                  70                  75                  80

Leu Gln Leu Asn Ser Leu Arg Thr Glu Asp Met Ala Met Tyr Tyr Cys
                 85                  90                  95

Arg Arg Cys Ala Asp Ile Tyr Cys Ser Gly Ser Gly Gly Trp Thr Gly
            100                 105                 110

Gln Gly Thr Gln Val Thr Val Ser Ser
        115                 120
```

<210> SEQ ID NO 51
<211> LENGTH: 127
<212> TYPE: PRT
<213> ORGANISM: Camelus bactrianus

<400> SEQUENCE: 51

```
Gln Val Gln Leu Gln Glu Ser Gly Gly Gly Ser Val Gln Thr Gly Gly
 1               5                  10                  15

Ser Leu Arg Leu Ser Cys Thr Ala Ser Thr Ser Ile Tyr Ser Asn Ser
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
 50                      55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg His Tyr Trp Tyr Thr Ser Ala
            100                 105                 110
```

```
Asn Tyr Asp Tyr Trp Gly Gln Gly Thr Gln Val Thr Val Ser Ser
        115                 120                 125
```

<210> SEQ ID NO 52
<211> LENGTH: 127
<212> TYPE: PRT
<213> ORGANISM: Camelus bactrianus

<400> SEQUENCE: 52

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
        35                  40                  45

Ala Ala Val Tyr Val Asp Asp Gly Arg Pro Tyr Tyr Ala Asp Ser Val
    50                  55                  60

Lys Gly Arg Phe Thr Ile Ser Arg Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125
```

<210> SEQ ID NO 53
<211> LENGTH: 127
<212> TYPE: PRT
<213> ORGANISM: Camelus bactrianus

<400> SEQUENCE: 53

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125
```

<210> SEQ ID NO 54
<211> LENGTH: 127
<212> TYPE: PRT
<213> ORGANISM: Camelus bactrianus

<400> SEQUENCE: 54

```
Gln Val Gln Leu Gln Glu Ser Gly Gly Gly Ser Val Gln Thr Gly Gly
1               5                   10                  15

Ser Leu Arg Leu Ser Cys Ala Pro Ser Thr Ser Ile Tyr Asp Asn Asn
```

```
                 20                  25                  30

Tyr Met Ala Trp Phe Ser Gln Ala Pro Gly Lys Gly Arg Glu Gly Val
             35                  40                  45

Ala Ala Ile Tyr Ile Asp Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 55
<211> LENGTH: 127
<212> TYPE: PRT
<213> ORGANISM: Camelus bactrianus

<400> SEQUENCE: 55

Gln Val Gln Leu Gln Glu Ser Gly Gly Gly Ser Val Gln Thr Gly Gly
 1               5                  10                  15

Ser Leu Arg Leu Ser Cys Val Ala Ser Thr Ser Ile Phe Ser Asn Asn
             20                  25                  30

Tyr Met Ala Trp Phe Ser Gln Ala Pro Gly Lys Gly Arg Glu Gly Val
             35                  40                  45

Ala Ala Val Tyr Ile Gly Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 56
<211> LENGTH: 127
<212> TYPE: PRT
<213> ORGANISM: Camelus bactrianus

<400> SEQUENCE: 56

Gln Val Gln Leu Gln Glu Ser Gly Gly Gly Ser Val Gln Thr Gly Gly
 1               5                  10                  15

Ser Leu Arg Leu Ser Cys Ala Ala Ser Pro Ser Ile Tyr Ser Ala Asn
             20                  25                  30

Tyr Met Ala Trp Phe Ser Gln Ala Pro Gly Lys Gly Arg Glu Gly Val
             35                  40                  45

Ala Ala Val Tyr Ile Gly Asp Gly Arg Pro Tyr Tyr Ala Asp Ser Val
         50                  55                  60

Lys Gly Arg Phe Thr Ile Ser Leu Asp Ser Ala Lys Ser Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser His Asn Tyr Trp Tyr Thr Ser Ala
```

Asn Tyr Asp Tyr Trp Gly Gln Gly Thr Gln Val Thr Val Ser Ser
            115                 120                 125

<210> SEQ ID NO 57
<211> LENGTH: 127
<212> TYPE: PRT
<213> ORGANISM: Camelus bactrianus

<400> SEQUENCE: 57

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Ile Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Ser Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 58
<211> LENGTH: 121
<212> TYPE: PRT
<213> ORGANISM: Camelus bactrianus

<400> SEQUENCE: 58

Gln Val Gln Leu Gln Glu Ser Gly Gly Gly Leu Val Gln Pro Gly Gly
1               5                   10                  15

Ser Leu Arg Leu Ser Cys Ala Leu Ser Gly Phe Thr Thr Ile Tyr
            20                  25                  30

Ala Met Ser Trp Val Arg Gln Ala Pro Gly Lys Gly Leu Glu Trp Val
        35                  40                  45

Ser Thr Ile Asn Ser Asp Gly Gly Tyr Arg Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Pro Lys Thr Glu Asp Thr Ala Met Tyr Tyr Cys
                85                  90                  95

Ala Arg Cys Ser Asp Ile Tyr Cys Tyr Asn Gly Pro Ser Tyr Arg Gly
            100                 105                 110

Gln Gly Thr Gln Val Thr Val Ser Ser
            115                 120

<210> SEQ ID NO 59
<211> LENGTH: 127
<212> TYPE: PRT
<213> ORGANISM: Camelus bactrianus

<400> SEQUENCE: 59

Gln Val Gln Leu Gln Glu Ser Gly Gly Gly Ser Val Gln Thr Gly Gly
1               5                   10                  15

Ser Leu Arg Leu Ser Cys Ala Cys Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Gly Asp Gly Arg Pro Tyr Tyr Thr Asp Ser Val
50                  55                  60

Lys Gly Arg Phe Thr Ile Ser Leu Asp Ser Ala Lys Asn Thr Leu Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 60
<211> LENGTH: 127
<212> TYPE: PRT
<213> ORGANISM: Camelus bactrianus

<400> SEQUENCE: 60

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Met Asn
            20                  25                  30

Tyr Met Ala Trp Phe Ser Gln Ala Pro Gly Lys Gly Arg Glu Gly Val
            35                  40                  45

Ala Ala Val Tyr Ile Glu Asp Gly Arg Pro Tyr Tyr Ala Asp Ser Val
50                  55                  60

Lys Gly Arg Phe Thr Ile Ser Pro Asp Arg Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 61
<211> LENGTH: 121
<212> TYPE: PRT
<213> ORGANISM: Camelus bactrianus

<400> SEQUENCE: 61

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asp Phe Ser Ser Arg
            20                  25                  30

Ala Met Ser Trp Val Arg Gln Ala Pro Gly Lys Gly Leu Glu Trp Val
            35                  40                  45

Ser Thr Ile Asn Ser Gly Gly Ser Arg Tyr Tyr Ala Asp Ser Val
50                  55                  60

Lys Gly Arg Phe Thr Thr Ser Arg Asp Asn Ala Lys Asn Thr Leu Ala
65                  70                  75                  80

Leu Gln Leu Asn Ser Leu Lys Thr Glu Asp Thr Ala Met Tyr Tyr Cys
            85                  90                  95

```
Ala Arg Cys Ser Asp Ile Tyr Cys Asp Asn Gly Ala Trp Tyr Arg Gly
            100                 105                 110

Gln Gly Thr Gln Val Thr Val Ser Ser
        115                 120

<210> SEQ ID NO 62
<211> LENGTH: 127
<212> TYPE: PRT
<213> ORGANISM: Camelus bactrianus

<400> SEQUENCE: 62

Gln Val Gln Leu Gln Glu Ser Gly Gly Gly Ser Val Gln Ala Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Thr Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asp Tyr Trp Tyr Thr Ser Ala
            100                 105                 110

Asn Tyr Asp Tyr Trp Gly Pro Gly Thr Gln Val Thr Val Ser Ser
        115                 120                 125

<210> SEQ ID NO 63
<211> LENGTH: 127
<212> TYPE: PRT
<213> ORGANISM: Camelus bactrianus

<400> SEQUENCE: 63

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Arg Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 64
<211> LENGTH: 127
<212> TYPE: PRT
<213> ORGANISM: Camelus bactrianus

<400> SEQUENCE: 64
```

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Thr Pro Gly Pro Leu Ser Gln His Tyr Trp Tyr Thr Ser Ala
        100                 105                 110

Asn Tyr Asp Tyr Trp Gly Gln Gly Thr Gln Val Thr Val Ser Ser
            115                 120                 125
```

<210> SEQ ID NO 65
<211> LENGTH: 121
<212> TYPE: PRT
<213> ORGANISM: Camelus bactrianus

<400> SEQUENCE: 65

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Leu
            20                  25                  30

Ala Met Ser Trp Val Arg Gln Ala Pro Gly Lys Gly Leu Glu Trp Ile
        35                  40                  45

Ser Thr Ile Asn Asn Ser Gly Thr Thr Phe Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
            85                  90                  95

Arg Arg Cys Thr Asp Ile Tyr Cys Ser Leu Ser Gly Gly Trp Thr Gly
        100                 105                 110

Gln Gly Thr Gln Val Thr Val Ser Ser
            115                 120
```

<210> SEQ ID NO 66
<211> LENGTH: 127
<212> TYPE: PRT
<213> ORGANISM: Camelus bactrianus

<400> SEQUENCE: 66

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Asn Asn Asn
            20                  25                  30

Tyr Met Ala Trp Phe Ser Gln Ala Pro Gly Lys Gly Arg Glu Gly Val
        35                  40                  45

Ala Ala Val Tyr Val Gly Asp Gly Arg Thr Tyr Tyr Ala Asp Ser Val
    50                  55                  60

Lys Gly Arg Phe Thr Ile Ser Leu Asp Ser Ala Lys Asn Thr Val Tyr
65                  70                  75                  80
```

Leu Gln Met Asn Ser Leu Lys Pro Glu Asp Thr Ala Met Tyr Tyr Cys
                    85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 67
<211> LENGTH: 127
<212> TYPE: PRT
<213> ORGANISM: Camelus bactrianus

<400> SEQUENCE: 67

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
            50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                    85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 68
<211> LENGTH: 127
<212> TYPE: PRT
<213> ORGANISM: Camelus bactrianus

<400> SEQUENCE: 68

Gln Val Gln Leu Gln Glu Ser Gly Gly Gly Ser Val Gln Thr Gly Gly
1               5                   10                  15

Ser Leu Arg Leu Ser Cys Thr Cys Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Gly Asp Gly Arg Pro Tyr Tyr Ala Asp Ser Val
            50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                    85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 69
<211> LENGTH: 127
<212> TYPE: PRT
<213> ORGANISM: Camelus bactrianus

<400> SEQUENCE: 69

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 70
<211> LENGTH: 121
<212> TYPE: PRT
<213> ORGANISM: Camelus bactrianus

<400> SEQUENCE: 70

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Arg
            20                  25                  30

Ala Met Ser Trp Val Arg Gln Ala Pro Gly Lys Gly Leu Glu Trp Val
        35                  40                  45

Ser Thr Ile Asn Ser Gly Gly Asp Ser Arg Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Leu Asn Ser Leu Lys Thr Glu Asp Thr Ala Met Tyr Tyr Cys
                85                  90                  95

Val Arg Cys Ser Asp Ile Tyr Cys Tyr Asn Gly Ala Ser Tyr Arg Gly
            100                 105                 110

Gln Gly Thr Gln Val Thr Val Ser Ser
        115                 120

<210> SEQ ID NO 71
<211> LENGTH: 122
<212> TYPE: PRT
<213> ORGANISM: Camelus bactrianus

<400> SEQUENCE: 71

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Ile Glu Trp Val
        35                  40                  45

Ser Val Ile Asn Ser Gly Gly Ser Asn Thr Asp Tyr Ala Asp Ser Val
    50                  55                  60

Lys Gly Arg Phe Thr Ile Ser Arg Asp Asn Ala Lys Asn Thr Leu Tyr

```
                65                  70                  75                  80
Leu Gln Met Asn Ser Leu Lys Thr Glu Asp Thr Ala Val Tyr Tyr Cys
                    85                  90                  95

Ala Thr Ala Trp Met Gly Tyr Ser Asp Tyr Leu Asp Gly Ile Ala Arg
                    100                 105                 110

Gly Gln Gly Thr Gln Val Thr Val Ser Ser
                    115                 120

<210> SEQ ID NO 72
<211> LENGTH: 121
<212> TYPE: PRT
<213> ORGANISM: Camelus bactrianus

<400> SEQUENCE: 72

Gln Val Gln Leu Gln Glu Ser Gly Gly Gly Leu Val Gln Pro Gly Gly
1               5                   10                  15

Ser Leu Arg Leu Ser Cys Glu Ala Ser Gly Leu Pro Phe Ser Ile Ile
                20                  25                  30

Ala Met Ser Trp Val Arg Gln Ala Pro Gly Lys Gly Leu Glu Trp Val
                35                  40                  45

Ser Thr Ile Asn Ser Asp Gly Gly Thr Thr His Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                    85                  90                  95

Arg Arg Cys Thr Asp Ile Tyr Cys Ser Gly Ser Gly Trp Thr Gly
                    100                 105                 110

Gln Gly Thr Gln Val Thr Val Ser Ser
                    115                 120

<210> SEQ ID NO 73
<211> LENGTH: 121
<212> TYPE: PRT
<213> ORGANISM: Camelus bactrianus

<400> SEQUENCE: 73

Gln Val Gln Leu Gln Glu Ser Gly Gly Gly Leu Val Gln Pro Gly Gly
1               5                   10                  15

Ser Leu Arg Leu Ser Cys Glu Ala Ser Gly Leu Pro Phe Ser Ile Ile
                20                  25                  30

Ala Met Ser Trp Val Arg Gln Ala Pro Gly Lys Gly Leu Glu Trp Val
                35                  40                  45

Ser Thr Ile Asn Ser Asp Gly Gly Thr Thr His Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                    85                  90                  95

Arg Arg Cys Thr Asp Ile Tyr Cys Ser Gly Phe Gly Gly Trp Thr Gly
                    100                 105                 110

Gln Gly Thr Gln Val Thr Val Ser Ser
                    115                 120

<210> SEQ ID NO 74
<211> LENGTH: 121
<212> TYPE: PRT
```

<213> ORGANISM: Camelus bactrianus

<400> SEQUENCE: 74

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Ser Ile Tyr
            20                  25                  30

Ala Met Ser Trp Val Arg Gln Ala Pro Gly Lys Gly Leu Glu Trp Val
                35                  40                  45

Ser Thr Ile Ser Ser Ser Gly Arg Arg Phe Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Leu Asn Ser Leu Lys Thr Glu Asp Thr Ala Met Tyr Tyr Cys
                85                  90                  95

Ala Arg Cys Ser Asp Ile Tyr Cys Asp Asn Gly Ala Ser Tyr Arg Gly
                100                 105                 110

Gln Gly Thr Gln Val Thr Val Ser Ser
            115                 120

<210> SEQ ID NO 75
<211> LENGTH: 127
<212> TYPE: PRT
<213> ORGANISM: Camelus bactrianus

<400> SEQUENCE: 75

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
                35                  40                  45

Ala Ala Val Tyr Ile Gly Asp Gly Arg Pro Tyr Tyr Ala Asp Ser Ala
            50                  55                  60

Lys Gly Arg Phe Thr Ile Ser Leu Asp Ser Ala Lys Asn Thr Val Tyr
65                  70                  75                  80

Leu His Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
                100                 105                 110

Asn Tyr Asp Tyr Trp Gly Pro Gly Thr Gln Val Thr Val Ser Ser
            115                 120                 125

<210> SEQ ID NO 76
<211> LENGTH: 127
<212> TYPE: PRT
<213> ORGANISM: Camelus bactrianus

<400> SEQUENCE: 76

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Val Pro Gly Lys Gly Arg Glu Gly Val
                35                  40                  45

Ala Ala Val Tyr Ile Asp Asp Gly Arg Thr Tyr Tyr Ala Asp Ser Val
            50                  55                  60

```
Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125
```

<210> SEQ ID NO 77
<211> LENGTH: 127
<212> TYPE: PRT
<213> ORGANISM: Camelus bactrianus

<400> SEQUENCE: 77

```
Gln Val Gln Leu Gln Glu Ser Gly Gly Gly Ser Val Gln Thr Gly Gly
 1               5                  10                  15

Ser Leu Arg Leu Ser Cys Thr Ala Ser Thr Ser Ile Tyr Ser Asn Asn
                20                  25                  30

Tyr Met Ala Trp Phe Ser Gln Ala Pro Gly Lys Gly Arg Glu Gly Val
             35                  40                  45

Ala Ala Val Tyr Ile Asp Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125
```

<210> SEQ ID NO 78
<211> LENGTH: 127
<212> TYPE: PRT
<213> ORGANISM: Camelus bactrianus

<400> SEQUENCE: 78

```
Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Leu Tyr Ser Tyr Asn
                20                  25                  30

Tyr Met Ala Trp Phe Ser Gln Ala Pro Gly Lys Gly Arg Glu Gly Val
             35                  40                  45

Ala Ala Val Tyr Val Gly Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125
```

<210> SEQ ID NO 79

<211> LENGTH: 121
<212> TYPE: PRT
<213> ORGANISM: Camelus bactrianus

<400> SEQUENCE: 79

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Leu Pro Phe Ser Ile Ile
            20                  25                  30

Ala Met Ser Trp Val Arg Gln Ala Pro Gly Lys Gly Ile Glu Trp Val
        35                  40                  45

Ser Thr Ile Asn Ser Gly Gly Gly Thr Thr His Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Val Tyr Tyr Cys
                85                  90                  95

Arg Arg Cys Ala Asp Ile Tyr Cys Ser Gly Ser Gly Trp Thr Gly
            100                 105                 110

Leu Gly Thr Gln Val Thr Val Ser Ser
        115                 120
```

<210> SEQ ID NO 80
<211> LENGTH: 127
<212> TYPE: PRT
<213> ORGANISM: Camelus bactrianus

<400> SEQUENCE: 80

```
Gln Val Gln Leu Gln Glu Ser Gly Gly Gly Ser Val Gln Thr Gly Gly
1               5                   10                  15

Ser Leu Arg Leu Ser Cys Val Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Ser Tyr Trp Tyr Thr Ser Ala
            100                 105                 110

Asn Tyr Asp Tyr Trp Gly Gln Gly Thr Gln Val Thr Val Ser Ser
        115                 120                 125
```

<210> SEQ ID NO 81
<211> LENGTH: 127
<212> TYPE: PRT
<213> ORGANISM: Camelus bactrianus

<400> SEQUENCE: 81

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45
```

Ala Ala Val Tyr Ile Asp Asp Gly Arg Thr Tyr Tyr Ala Asp Ser Val
              50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                  85                  90                  95

Ala Ala Ala Pro Gly Pro Leu Ser Arg Asn Tyr Trp Tyr Thr Ser Ala
             100                 105                 110

Asn Tyr Asp Tyr Trp Gly Gln Gly Thr Gln Val Thr Val Ser Ser
             115                 120                 125

<210> SEQ ID NO 82
<211> LENGTH: 127
<212> TYPE: PRT
<213> ORGANISM: Camelus bactrianus

<400> SEQUENCE: 82

Gln Val Gln Leu Gln Glu Ser Gly Gly Gly Ser Val Gln Thr Gly Gly
 1               5                  10                  15

Ser Leu Arg Leu Ser Cys Thr Ala Ser Thr Ser Ile Tyr Ser Asn Asn
                  20                  25                  30

Tyr Met Ala Trp Phe Ser Gln Ala Pro Gly Lys Gly Arg Glu Gly Val
             35                  40                  45

Ala Ala Val Tyr Ile Asp Asp Gly Arg Pro Tyr Tyr Ala Asp Ser Val
              50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                  85                  90                  95

Ala Ala Ala Pro Gly Pro Leu Ser Arg Asn Tyr Trp Tyr Thr Ser Ala
             100                 105                 110

Asn Tyr Asp Tyr Trp Gly Gln Gly Thr Gln Val Thr Val Ser Ser
             115                 120                 125

<210> SEQ ID NO 83
<211> LENGTH: 127
<212> TYPE: PRT
<213> ORGANISM: Camelus bactrianus

<400> SEQUENCE: 83

Gln Val Gln Leu Gln Glu Ser Gly Gly Gly Leu Val Gln Thr Gly Gly
 1               5                  10                  15

Ser Leu Arg Leu Ser Cys Ala Ala Ser Thr Ser Ile Tyr Ser Asn Asn
                  20                  25                  30

Tyr Leu Ala Trp Phe Ser Gln Ala Pro Gly Lys Gly Arg Glu Gly Val
             35                  40                  45

Ala Ala Val Tyr Ile Gly Asp Gly Arg Pro Tyr Tyr Ala Asp Ser Val
              50                  55                  60

Lys Gly Arg Phe Pro Ile Ser Leu Asn Ser Ala Gln Asn Lys Val Tyr
 65                  70                  75                  80

Leu Gln Met Asn Ser Leu Lys Pro Glu Asp Thr Ala Met Tyr Tyr Cys
                  85                  90                  95

Ala Ala Ala Pro Gly Pro Leu Ser Arg Asn Tyr Trp Tyr Thr Ser Ala
             100                 105                 110

Asn Tyr Asp Tyr Trp Gly Gln Gly Thr Gln Val Thr Val Ser Ser
             115                 120                 125

<210> SEQ ID NO 84
<211> LENGTH: 127
<212> TYPE: PRT
<213> ORGANISM: Camelus bactrianus

<400> SEQUENCE: 84

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Asp Ser Asn Asn
            20                  25                  30

Tyr Met Ala Trp Phe Arg Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg His Tyr Trp Tyr Thr Ser Ala
        100                 105                 110

Asn Tyr Asp Tyr Trp Gly Pro Gly Thr Gln Val Thr Val Ser Ser
    115                 120                 125

<210> SEQ ID NO 85
<211> LENGTH: 127
<212> TYPE: PRT
<213> ORGANISM: Camelus bactrianus

<400> SEQUENCE: 85

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Ala Asp Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg Asn Tyr Trp Tyr Thr Ser Ala
        100                 105                 110

Asn Tyr Asp Tyr Trp Gly Gln Gly Thr Gln Val Thr Val Ser Ser
    115                 120                 125

<210> SEQ ID NO 86
<211> LENGTH: 127
<212> TYPE: PRT
<213> ORGANISM: Camelus bactrianus

<400> SEQUENCE: 86

Gln Val Gln Leu Gln Asp Ser Gly Gly Gly Ser Val Gln Thr Gly Gly
1               5                   10                  15

Ser Leu Arg Leu Ser Cys Ala Ala Ser Thr Ser Ile Tyr Ser Ile Asn
            20                  25                  30

Tyr Met Ala Trp Phe Ser Gln Ala Pro Gly Lys Gly Arg Glu Gly Val

```
            35                  40                  45

Ala Ala Val Tyr Thr Gly Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 87
<211> LENGTH: 127
<212> TYPE: PRT
<213> ORGANISM: Camelus bactrianus

<400> SEQUENCE: 87

Gln Val Gln Leu Gln Glu Ser Gly Gly Gly Ser Val Gln Ala Gly Gly
 1               5                   10                  15

Ser Leu Arg Leu Ser Cys Ala Ala Ser Gly Tyr Thr Arg Ser Ser Tyr
            20                  25                  30

Cys Met Gly Trp Phe Arg Gln Ala Pro Gly Lys Glu Arg Glu Arg Val
        35                  40                  45

Ala Tyr Ile Tyr Ser Gly Ser Gly Ser Thr His Tyr Ala Asp Ser Val
        50                  55                  60

Lys Gly Arg Phe Thr Ile Ser Gln Asp Asn Gly Lys Asn Thr Leu Tyr
 65                  70                  75                  80

Leu Gln Met Asn Asn Leu Lys Pro Glu Asp Thr Ala Met Tyr Tyr Cys
                85                  90                  95

Ala Ala Gly Thr Ser Gly Thr Ser Cys Pro Thr Gly Ala Phe Met Tyr
            100                 105                 110

Glu Tyr Trp Tyr Trp Gly Gln Gly Thr Gln Val Thr Val Ser Ser
            115                 120                 125

<210> SEQ ID NO 88
<211> LENGTH: 127
<212> TYPE: PRT
<213> ORGANISM: Camelus bactrianus

<400> SEQUENCE: 88

Gln Val Gln Leu Gln Glu Ser Gly Gly Gly Ser Val Gln Ala Gly Gly
 1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
        35                  40                  45

Ala Ala Val Tyr Val Gly Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
```

115                 120                 125

<210> SEQ ID NO 89
<211> LENGTH: 127
<212> TYPE: PRT
<213> ORGANISM: Camelus bactrianus

<400> SEQUENCE: 89

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Arg Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 90
<211> LENGTH: 127
<212> TYPE: PRT
<213> ORGANISM: Camelus bactrianus

<400> SEQUENCE: 90

Gln Val Gln Leu Gln Glu Ser Gly Gly Gly Ser Val Gln Ala Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 91
<211> LENGTH: 121
<212> TYPE: PRT
<213> ORGANISM: Camelus bactrianus

<400> SEQUENCE: 91

Gln Val Gln Leu Gln Glu Ser Gly Gly Asp Leu Val Gln Pro Gly Gly
1               5                   10                  15

Ser Leu Arg Leu Ser Cys Ala Ala Ser Gly Leu Pro Phe Ser Ile Ile
            20                  25                  30

Ala Met Ser Trp Val Arg Gln Ala Pro Gly Lys Gly Leu Glu Trp Val
            35                  40                  45

Ser Thr Ile Asn Asn Asp Gly Gly Thr Thr His Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                85                  90                  95

Arg Arg Cys Thr Asp Ile Tyr Cys Ser Gly Ser Gly Gly Trp Thr Gly
                100                 105                 110

Gln Gly Thr Gln Val Thr Val Ser Ser
            115                 120

<210> SEQ ID NO 92
<211> LENGTH: 127
<212> TYPE: PRT
<213> ORGANISM: Camelus bactrianus

<400> SEQUENCE: 92

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Asn Asn Asn
            20                  25                  30

Tyr Met Ala Trp Phe Arg Gln Ala Pro Gly Lys Gly Arg Glu Gly Val
            35                  40                  45

Ala Ala Val Tyr Ile Asp Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
                100                 105                 110

Asn Tyr Asp Tyr Trp Gly Pro Gly Thr Gln Val Thr Val Ser Ser
            115                 120                 125

<210> SEQ ID NO 93
<211> LENGTH: 127
<212> TYPE: PRT
<213> ORGANISM: Camelus bactrianus

<400> SEQUENCE: 93

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
            35                  40                  45

Ala Ala Val Tyr Ile Gly Asp Gly Arg Thr Tyr Tyr Ala Asp Ser Ala
        50                  55                  60

Lys Gly Arg Phe Thr Ile Ser Leu Asp Ser Ala Lys Asn Thr Val Tyr
65                  70                  75                  80

Leu His Met Asn Ser Leu Lys Pro Asp Asp Thr Ala Met Tyr Tyr Cys
                85                  90                  95

Ala Ala Ala Pro Gly Pro Leu Thr Arg His Phe Trp Tyr Thr Ser Ala
                100                 105                 110

Asn Tyr Asp Tyr Trp Gly Pro Gly Thr Gln Val Thr Val Ser Ser
            115                 120                 125

<210> SEQ ID NO 94
<211> LENGTH: 127
<212> TYPE: PRT
<213> ORGANISM: Camelus bactrianus

<400> SEQUENCE: 94

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Leu Tyr Ser Tyr Asn
            20                  25                  30

Tyr Met Ala Trp Phe Ser Gln Ala Pro Gly Lys Gly Arg Gly Gly Val
        35                  40                  45

Ala Ala Val Tyr Val Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 95
<211> LENGTH: 127
<212> TYPE: PRT
<213> ORGANISM: Camelus bactrianus

<400> SEQUENCE: 95

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Val Ser Asn Asn
            20                  25                  30

Tyr Met Gly Trp Phe Arg Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Gln His Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 96
<211> LENGTH: 113
<212> TYPE: PRT
<213> ORGANISM: Camelus bactrianus

<400> SEQUENCE: 96

Gln Val Gln Leu Gln Glu Ser Gly Gly Gly Leu Val Gln Pro Gly Gly
1               5                   10                  15

```
Ser Leu Arg Leu Ser Cys Ala Ala Phe Gly Phe Thr Phe Gly Ser Tyr
            20                  25                  30

Trp Met Lys Trp Val Arg Gln Ala Pro Gly Lys Asp Leu Glu Trp Val
            35                  40                  45

Pro Ile Ile Asp Asn Gly Gly Arg Ser Thr Trp Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Leu Asn Ser Leu Lys Ile Glu Asp Thr Ala Met Tyr Tyr Cys
                85                  90                  95

Ala Asp Arg Asn Gly Asn Arg Gly Gln Gly Thr Gln Val Thr Val Ser
            100                 105                 110

Ser

<210> SEQ ID NO 97
<211> LENGTH: 127
<212> TYPE: PRT
<213> ORGANISM: Camelus bactrianus

<400> SEQUENCE: 97

Gln Val Gln Leu Gln Glu Ser Gly Gly Gly Ser Val Gln Thr Gly Gly
1               5                   10                  15

Ser Leu Arg His Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 98
<211> LENGTH: 127
<212> TYPE: PRT
<213> ORGANISM: Camelus bactrianus

<400> SEQUENCE: 98

Gln Val Gln Leu Gln Glu Ser Gly Gly Gly Ser Val Gln Thr Gly Gly
1               5                   10                  15

Ser Leu Arg His Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
```

Asn Tyr Asp Tyr Trp Gly Gln Gly Thr Gln Val Thr Val Ser Ser
        115                 120                 125

<210> SEQ ID NO 99
<211> LENGTH: 127
<212> TYPE: PRT
<213> ORGANISM: Camelus bactrianus

<400> SEQUENCE: 99

Gln Val Gln Leu Gln Glu Ser Gly Gly Gly Ser Val Thr Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125

<210> SEQ ID NO 100
<211> LENGTH: 121
<212> TYPE: PRT
<213> ORGANISM: Camelus bactrianus

<400> SEQUENCE: 100

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Met
            20                  25                  30

Ala Met Ser Trp Val Arg Gln Ala Pro Gly Arg Gly Leu Glu Trp Val
        35                  40                  45

Ser Thr Ile Asn Ser Asp Gly Gly Lys Thr Tyr Tyr Ala Asp Ser Val
    50                  55                  60

Lys Gly Arg Phe Thr Ala Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                85                  90                  95

Arg Arg Cys Ala Asp Ile Tyr Cys Ser Gly Ser Gly Gly Trp Thr Gly
            100                 105                 110

Gln Gly Thr Gln Val Thr Val Ser Ser
        115                 120

<210> SEQ ID NO 101
<211> LENGTH: 126
<212> TYPE: PRT
<213> ORGANISM: Camelus bactrianus

<400> SEQUENCE: 101

Gln Val Gln Leu Gln Glu Ser Gly Gly Gly Ser Val Gln Thr Gly Gly
1               5                   10                  15

```
Ser Leu Arg Leu Ser Cys Ala Val Ser Gly Phe Thr Asp Thr Tyr Phe
            20                  25                  30

Ala Leu Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ala Lys Asn Thr Val Tyr Leu
65                  70                  75                  80

Gln Met Asn Ser Leu Lys Pro Glu Asp Thr Ala Met Tyr Tyr Cys Ala
                85                  90                  95

Ala Ala Pro Gly Pro Leu Ser Arg Asn Tyr Trp Tyr Thr Ser Ala Asn
            100                 105                 110

Tyr Asp Tyr Trp Gly Gln Gly Thr Gln Val Thr Val Ser Ser
            115                 120                 125
```

<210> SEQ ID NO 102
<211> LENGTH: 127
<212> TYPE: PRT
<213> ORGANISM: Camelus bactrianus

<400> SEQUENCE: 102

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Ala Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
            115                 120                 125
```

<210> SEQ ID NO 103
<211> LENGTH: 127
<212> TYPE: PRT
<213> ORGANISM: Camelus bactrianus

<400> SEQUENCE: 103

```
Gln Val Gln Leu Gln Glu Ser Gly Gly Gly Ser Val Gln Thr Gly Gly
1               5                   10                  15

Ser Leu Arg Leu Ser Cys Ala Ser Thr Ser Ile Tyr Asn Asn Asn
            20                  25                  30

Tyr Met Ala Trp Phe Ser Gln Ala Pro Gly Lys Gly Arg Glu Gly Val
        35                  40                  45

Ala Ala Val Tyr Ile Glu Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95
```

```
Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 104
<211> LENGTH: 127
<212> TYPE: PRT
<213> ORGANISM: Camelus bactrianus

<400> SEQUENCE: 104

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
            35                  40                  45

Ala Ala Val Tyr Ile Asp Asp Gly Arg Thr Tyr Tyr Ala Asp Ser Val
        50                  55                  60

Lys Gly Arg Phe Ala Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
            85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
            115                 120                 125

<210> SEQ ID NO 105
<211> LENGTH: 121
<212> TYPE: PRT
<213> ORGANISM: Camelus bactrianus

<400> SEQUENCE: 105

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Leu
            20                  25                  30

Ala Met Ser Trp Val Arg Gln Ala Pro Gly Lys Gly Leu Glu Trp Val
            35                  40                  45

Ser Thr Ile Asn Ser Gly Gly Val Tyr Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Leu Asn Asn Leu Arg Thr Glu Asp Thr Ala Met Tyr Tyr Cys
            85                  90                  95

Arg Arg Cys Thr Asp Ile Tyr Cys Ser Gly Ser Gly Gly Trp Thr Gly
            100                 105                 110

Gln Gly Thr Gln Val Thr Val Ser Ser
            115                 120

<210> SEQ ID NO 106
<211> LENGTH: 121
<212> TYPE: PRT
<213> ORGANISM: Camelus bactrianus

<400> SEQUENCE: 106
```

-continued

```
Gln Val Gln Leu Gln Glu Ser Gly Gly Gly Leu Val Gln Pro Gly Gly
1               5                   10                  15

Ser Leu Arg Leu Ser Cys Ala Val Ser Gly Phe Thr Phe Ser Ile Ile
            20                  25                  30

Ala Met Ser Trp Val Arg Gln Ala Pro Gly Lys Gly Leu Glu Trp Val
        35                  40                  45

Ser Thr Ile Asn Ser Asp Gly Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                85                  90                  95

Arg Arg Cys Ala Asp Ile Tyr Cys Ser Gly Ser Gly Gly Trp Thr Gly
                100                 105                 110

Gln Gly Thr Gln Val Thr Val Ser Ser
            115                 120
```

<210> SEQ ID NO 107
<211> LENGTH: 122
<212> TYPE: PRT
<213> ORGANISM: Camelus bactrianus

<400> SEQUENCE: 107

```
Gln Val Gln Leu Gln Glu Ser Gly Gly Gly Leu Val Gln Pro Gly Gly
1               5                   10                  15

Ser Leu Arg Leu Ser Cys Glu Ala Ser Gly Leu Pro Phe Ser Ile Ile
            20                  25                  30

Ala Met Ser Trp Val Arg Gln Ala Pro Gly Lys Gly Leu Glu Trp Val
        35                  40                  45

Ser Thr Ile Asn Ser Asp Gly Gly Thr Thr His Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Ser Glu Asp Thr Ala Met Tyr Tyr Cys
                85                  90                  95

Arg Arg Cys Thr Asp Ile Tyr Cys Ser Gly Ser Gly Gly Ser Thr Lys
                100                 105                 110

Gly Gln Gly Thr Gln Val Thr Val Ser Ser
            115                 120
```

<210> SEQ ID NO 108
<211> LENGTH: 127
<212> TYPE: PRT
<213> ORGANISM: Camelus bactrianus

<400> SEQUENCE: 108

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80
```

```
Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Thr Ala
            100                 105                 110

Asn Tyr Asp Tyr Trp Gly Pro Gly Thr Gln Val Thr Val Ser Ser
        115                 120                 125

<210> SEQ ID NO 109
<211> LENGTH: 127
<212> TYPE: PRT
<213> ORGANISM: Camelus bactrianus

<400> SEQUENCE: 109

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Arg Ser Ser Tyr
            20                  25                  30

Cys Met Gly Trp Phe Arg Gln Ala Pro Gly Lys Glu Arg Glu Arg Val
            35                  40                  45

Ala His Ile Tyr Thr Gly Ser Gly Thr Thr His Tyr Ala Asp Ser Met
        50                  55                  60

Lys Gly Arg Phe Thr Ile Ser Gln Asp Asn Gly Lys Asn Thr Leu Tyr
65                  70                  75                  80

Leu Gln Met Asn Asn Leu Lys Pro Glu Asp Thr Ala Met Tyr Tyr Cys
                85                  90                  95

Ala Ala Gly Thr Ser Gly Thr Ser Cys Ala Thr Gly Pro Phe Val Tyr
            100                 105                 110

Gly Tyr Trp Tyr Trp Gly Gln Gly Thr Gln Val Thr Val Ser Ser
        115                 120                 125

<210> SEQ ID NO 110
<211> LENGTH: 129
<212> TYPE: PRT
<213> ORGANISM: Camelus bactrianus

<400> SEQUENCE: 110

Gln Val Gln Leu Gln Glu Ser Gly Gly Gly Ser Val Gln Ala Gly Gly
1               5                   10                  15

Ser Leu Arg Leu Ser Cys Ala Tyr Thr Pro Arg Arg Leu Cys Met Gly
            20                  25                  30

Met Gly Trp Phe Arg Gln Gly Leu Gly Lys Glu Arg Glu Gly Val Ala
            35                  40                  45

Thr Ile Asp Asp Ala Gly Ser Thr Thr Tyr Ala Asp Ser Val Lys Ala
        50                  55                  60

Arg Phe Thr Ile Ser Gln Asp Asn Ala Lys Asn Thr Leu Tyr Leu Gln
65                  70                  75                  80

Met Asp Ser Leu Lys Pro Glu Asp Ser Ala Met Tyr Tyr Cys Ala Ala
                85                  90                  95

Arg Ala Gly Val Gly Trp Tyr Gln Val Ser Cys Pro Glu Glu Ser Arg
            100                 105                 110

Thr Ser Ala Phe Val Tyr Trp Gly Gln Gly Thr Gln Val Thr Val Ser
        115                 120                 125

Ser

<210> SEQ ID NO 111
<211> LENGTH: 127
<212> TYPE: PRT
```

```
<213> ORGANISM: Camelus bactrianus

<400> SEQUENCE: 111

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Asn Asn Asn
            20                  25                  30

Tyr Met Ala Trp Phe Ser Gln Ala Pro Gly Lys Gly Arg Glu Gly Val
        35                  40                  45

Ala Ala Val Tyr Ile Glu Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 112
<211> LENGTH: 121
<212> TYPE: PRT
<213> ORGANISM: Camelus bactrianus

<400> SEQUENCE: 112

Gln Val Gln Leu Gln Glu Ser Gly Gly Gly Leu Val Gln Pro Gly Gly
1               5                   10                  15

Ser Leu Arg Leu Ser Cys Ala Ala Ser Gly Leu Thr Phe Ser Ile Val
            20                  25                  30

Ala Met Ser Trp Val Arg Gln Ala Pro Gly Lys Gly Leu Glu Trp Val
        35                  40                  45

Ser Thr Ile Asn Ser Asp Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                85                  90                  95

Arg Arg Cys Thr Asp Ile Tyr Cys Ser Gly Ser Gly Trp Thr Gly
            100                 105                 110

Gln Gly Thr Gln Val Thr Val Ser Ser
        115                 120

<210> SEQ ID NO 113
<211> LENGTH: 127
<212> TYPE: PRT
<213> ORGANISM: Camelus bactrianus

<400> SEQUENCE: 113

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Ile Ser Phe Asn
            20                  25                  30

Tyr Met Ala Trp Phe Arg Arg Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60
```

Lys Gly Arg Phe Thr Ile Ser Leu Asp Ser Ala Lys Asn Thr Val Tyr
65                  70                  75                  80

Leu Gln Met Gly Ser Leu Arg Pro Glu Asp Thr Ala Met Tyr Tyr Cys
            85                  90                  95

Ala Ala Ala Pro Gly Pro Leu Ser Arg Asn Tyr Trp His Thr Pro Ala
            100                 105                 110

Asn Tyr Asp Tyr Trp Gly Gln Gly Thr Gln Val Thr Val Ser Ser
        115                 120                 125

<210> SEQ ID NO 114
<211> LENGTH: 124
<212> TYPE: PRT
<213> ORGANISM: Camelus bactrianus

<400> SEQUENCE: 114

Gln Val Gln Leu Gln Glu Ser Gly Gly Gly Ser Val Gln Thr Gly Gly
1               5                   10                  15

Ser Leu Arg Leu Ser Cys Ala Ala Ser Gly Tyr Ala Gly Arg Leu Tyr
            20                  25                  30

Ser Met Gly Trp Phe Arg Gln Val Ala Gly Lys Glu Arg Glu Gly Val
            35                  40                  45

Ser Ser Ile Glu Ser Asp Gly Ser Thr Phe Tyr Thr Asp Ser Val Lys
        50                  55                  60

Gly Arg Phe Thr Thr Thr Arg Asp Ser Ala Lys Asn Thr Leu Tyr Leu
65                  70                  75                  80

Gln Met Asn Asn Leu Lys Pro Glu Asp Thr Ala Met Tyr Tyr Cys Ala
            85                  90                  95

Ala Phe Cys Leu Arg Val Gly His Gly Gly Arg Cys Thr Glu Tyr Lys
            100                 105                 110

Tyr Trp Gly Arg Gly Thr Gln Val Thr Val Ser Ser
        115                 120

<210> SEQ ID NO 115
<211> LENGTH: 127
<212> TYPE: PRT
<213> ORGANISM: Camelus bactrianus

<400> SEQUENCE: 115

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Arg Ser Ser Tyr
            20                  25                  30

Cys Met Gly Trp Phe Arg Gln Ala Pro Gly Lys Glu Arg Glu Arg Val
            35                  40                  45

Ala His Ile Tyr Thr Gly Ser Gly Ser Thr His Tyr Ala Asp Ser Val
            50                  55                  60

Lys Gly Arg Phe Thr Ile Ser Gln Asp Asn Gly Lys Asn Thr Leu Tyr
65                  70                  75                  80

Leu Gln Met Asn Asn Leu Lys Pro Glu Asp Thr Ala Met Tyr Tyr Cys
            85                  90                  95

Ala Ala Gly Thr Ser Gly Thr Ser Cys Ala Thr Gly Pro Phe Val Tyr
            100                 105                 110

Lys Tyr Trp Tyr Trp Gly Gln Gly Thr Gln Val Thr Val Ser Ser
        115                 120                 125

<210> SEQ ID NO 116

```
<211> LENGTH: 121
<212> TYPE: PRT
<213> ORGANISM: Camelus bactrianus

<400> SEQUENCE: 116

Gln Leu Gln Glu Ser Gly Gly Gly Leu Val Gln Pro Gly Gly Ser Leu
1               5                   10                  15

Arg Leu Ser Cys Ala Ala Ser Gly Phe Ala Phe Ser Thr Tyr Ala Met
            20                  25                  30

Ser Trp Val Arg Gln Ala Pro Gly Lys Gly Leu Glu Trp Val Ser Gly
        35                  40                  45

Ile Asn Gly Gly Gly Asn Thr Tyr Tyr Ala Asp Ser Val Lys Gly
    50                  55                  60

Arg Phe Thr Ile Ser Arg Asp Asn Ala Lys Asn Thr Leu Tyr Leu Gln
65                  70                  75                  80

Leu Asn Ser Leu Lys Thr Glu Asp Thr Ala Met Tyr Tyr Cys Gly Gln
                85                  90                  95

Gly Ala Tyr Trp Ala Tyr Cys Asn Gly Tyr Cys Asn Pro Pro Gly
            100                 105                 110

Gln Gly Thr Gln Val Thr Val Ser Ser
        115                 120

<210> SEQ ID NO 117
<211> LENGTH: 127
<212> TYPE: PRT
<213> ORGANISM: Camelus bactrianus

<400> SEQUENCE: 117

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Gly Asp Gly Arg Pro Tyr Tyr Ala Asp Ser Val
        50                  55                  60

Lys Gly Arg Phe Thr Ile Ser Leu Asp Ser Ala Lys Asp Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 118
<211> LENGTH: 127
<212> TYPE: PRT
<213> ORGANISM: Camelus bactrianus

<400> SEQUENCE: 118

Gln Val Gln Leu Gln Glu Ser Gly Gly Gly Ser Val Gln Thr Gly Gly
1               5                   10                  15

Ser Leu Arg Leu Ser Cys Ala Ala Ser Ala Ser Ile Tyr Ser Asn Asn
            20                  25                  30

Tyr Met Ala Trp Phe Ser Gln Ala Pro Gly Lys Gly Arg Glu Gly Val
            35                  40                  45
```

-continued

Ala Ala Val Tyr Ile Gly Asp Gly Arg Pro Tyr Tyr Asp Ser Val
        50                  55                  60

Lys Gly Leu Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ile Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 119
<211> LENGTH: 127
<212> TYPE: PRT
<213> ORGANISM: Camelus bactrianus

<400> SEQUENCE: 119

Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Leu Tyr Ser Tyr Asn
            20                  25                  30

Tyr Met Ala Trp Phe Ser Gln Ala Pro Gly Lys Gly Arg Glu Gly Val
        35                  40                  45

Ala Ala Val Tyr Val Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 120
<211> LENGTH: 125
<212> TYPE: PRT
<213> ORGANISM: Camelus bactrianus

<400> SEQUENCE: 120

Gln Val Gln Leu Gln Glu Ser Gly Gly Gly Ser Val Gln Ala Gly Gly
 1               5                  10                  15

Ser Leu Arg Leu Ser Cys Thr Ala Pro Gly Phe Thr Ser Asn Thr Cys
            20                  25                  30

Ala Met Ala Trp Phe Arg Gln Ala Pro Gly Lys Glu Arg Glu Phe Val
        35                  40                  45

Ser Ser Met Ser Thr Val Gly Ser Thr Arg Phe Ala Asp Ser Val Lys
    50                  55                  60

Gly Arg Phe Thr Ile Ser Lys Asp Glu Val Lys Asp Thr Val Tyr Leu
 65                  70                  75                  80

Gln Met Asn Ser Leu Lys Pro Glu Asp Thr Ala Met Tyr Phe Cys Lys
                 85                  90                  95

Thr Tyr Ala Cys Arg Glu Cys Thr Gly Arg Tyr Cys Arg Thr Ala Pro
            100                 105                 110

Asp Ala Trp Gly Gln Gly Thr Gln Val Thr Val Ser Ser
            115                 120                 125

<210> SEQ ID NO 121
<211> LENGTH: 125
<212> TYPE: PRT
<213> ORGANISM: Camelus bactrianus

<400> SEQUENCE: 121

Gln Val Gln Leu Gln Glu Ser Gly Gly Gly Ser Ala Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Tyr Arg Gln Ala Pro Gly Lys Glu Arg Glu Phe Val
        35                  40                  45

Ser Ser Arg Ser Thr Val Gly Thr Thr Gly Tyr Ala Asp Ser Val Lys
    50                  55                  60

Gly Arg Phe Thr Ile Ser Lys Asp Glu Ala Lys Asp Thr Val Tyr Leu
65                  70                  75                  80

Gln Met Asn Ser Leu Lys Pro Glu Asp Thr Ala Met Tyr Phe Cys Lys
                85                  90                  95

Thr Tyr Ala Cys Arg Asn Cys Ile Gly Arg His Cys Arg Thr Ala Pro
            100                 105                 110

Asp Ala Trp Gly Gln Gly Thr Gln Val Thr Val Ser Ser
        115                 120                 125

<210> SEQ ID NO 122
<211> LENGTH: 125
<212> TYPE: PRT
<213> ORGANISM: Camelus bactrianus

<400> SEQUENCE: 122

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Phe Arg Gln Ala Pro Gly Lys Glu Arg Glu Phe Val
        35                  40                  45

Ser Ser Leu Ser Thr Val Gly Thr Thr Gly Tyr Ala Asp Ser Val Lys
    50                  55                  60

Gly Arg Phe Thr Ile Ser Lys Asp Glu Ala Lys Asp Thr Val Tyr Leu
65                  70                  75                  80

Leu Met Asn Ser Leu Lys Pro Glu Asp Thr Ala Met Tyr Phe Cys Lys
                85                  90                  95

Thr Phe Ala Cys Arg Asp Cys Ser Gly Arg Tyr Cys Arg Thr Ala Pro
            100                 105                 110

Asp Ala Trp Gly Gln Gly Thr Gln Val Thr Val Ser Ser
        115                 120                 125

<210> SEQ ID NO 123
<211> LENGTH: 125
<212> TYPE: PRT
<213> ORGANISM: Camelus bactrianus

<400> SEQUENCE: 123

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Tyr Arg Gln Ala Pro Gly Lys Glu Arg Glu Phe Val

```
            35                  40                  45
Ser Ser Arg Ser Thr Val Gly Thr Thr Gly Tyr Ala Asp Ser Val Lys
    50                  55                  60
Gly Arg Phe Thr Ile Ser Lys Asp Glu Ala Lys Asp Thr Val Tyr Leu
65                  70                  75                  80
Gln Met Asn Ser Leu Lys Pro Glu Asp Thr Ala Met Tyr Phe Cys Lys
                85                  90                  95
Thr Tyr Ala Cys Arg Asn Cys Ile Gly Arg His Cys Arg Thr Ala Pro
            100                 105                 110
Asp Ala Trp Gly Gln Gly Thr Gln Val Thr Val Ser Ser
        115                 120                 125

<210> SEQ ID NO 124
<211> LENGTH: 129
<212> TYPE: PRT
<213> ORGANISM: Camelus bactrianus

<400> SEQUENCE: 124

Gln Val Gln Leu Gln Glu Ser Gly Gly Gly Ser Val Gln Ala Gly Arg
1               5                   10                  15
Ser Leu Arg Leu Ser Cys Ala Val Ser Arg Tyr Ser Ala Ser Asn Asn
            20                  25                  30
Val Ile Lys Trp Met Gly Trp Phe Arg Gln Ala Pro Gly Lys Glu Arg
        35                  40                  45
Glu Gly Val Ala Ala Leu Tyr Thr Ser Gly Gly Asn Thr Tyr Tyr Ala
    50                  55                  60
Asp Ser Val Lys Gly Arg Phe Thr Ile Ser Arg Asp Tyr Ser Glu Asn
65                  70                  75                  80
Thr Val Ser Leu Gln Met Asn Asn Leu Lys Pro Glu Asp Thr Gly Met
                85                  90                  95
Tyr Tyr Cys Ala Ala Thr Val Gly Thr Val Leu Ala Gly Pro Leu Ser
            100                 105                 110
Ala Arg Lys Tyr Asn Tyr Trp Gly Gln Gly Thr Gln Val Thr Val Ser
        115                 120                 125
Ser

<210> SEQ ID NO 125
<211> LENGTH: 122
<212> TYPE: PRT
<213> ORGANISM: Camelus bactrianus

<400> SEQUENCE: 125

Gln Val Gln Leu Gln Glu Ser Gly Gly Gly Leu Val Gln Pro Gly Gly
1               5                   10                  15
Ser Leu Arg Leu Ser Cys Ala Ala Ser Gly Phe Thr Phe Ser Asn Ser
            20                  25                  30
Asp Met Ala Trp Phe Arg Gln Ala Pro Gly Lys Gly Leu Glu Trp Val
        35                  40                  45
Ser Val Ile Asp Ser Gly Gly Tyr Thr Tyr Tyr Ala Asp Ser Val
    50                  55                  60
Lys Gly Arg Phe Thr Ile Ser Arg Asp Asn Ala Glu Asn Thr Leu Tyr
65                  70                  75                  80
Leu Gln Leu Asn Ser Leu Lys Thr Glu Asp Thr Ala Met Tyr Tyr Cys
                85                  90                  95
Ala Lys Thr Asp Leu Arg Tyr Ser Arg Ile Tyr Pro Tyr Gly Lys Trp
            100                 105                 110
```

-continued

```
Gly Gln Gly Thr Gln Val Thr Val Ser Ser
        115                 120

<210> SEQ ID NO 126
<211> LENGTH: 129
<212> TYPE: PRT
<213> ORGANISM: Camelus bactrianus

<400> SEQUENCE: 126

Gln Val Gln Leu Gln Glu Ser Gly Gly Gly Ser Val Gln Ala Gly Arg
1               5                   10                  15

Ser Leu Arg Leu Pro Cys Ala Val Ser Arg Tyr Ser Ala Ser Asn Asn
            20                  25                  30

Val Ile Lys Trp Met Gly Trp Phe Arg Gln Ala Pro Gly Lys Glu Arg
        35                  40                  45

Glu Gly Val Ala Ala Leu Tyr Thr Ser Gly Gly Asn Thr Tyr Tyr Ala
    50                  55                  60

Asp Ser Val Lys Gly Arg Phe Thr Ile Ser Arg Asp Tyr Ser Glu Asn
65                  70                  75                  80

Thr Val Ser Leu Gln Met Asn Asn Leu Lys Pro Glu Asp Thr Gly Met
                85                  90                  95

Tyr Tyr Cys Ala Ala Thr Val Gly Thr Val Leu Ala Gly Pro Leu Ser
            100                 105                 110

Ala Arg Lys Tyr Asn Tyr Trp Gly Gln Gly Thr Gln Val Thr Val Ser
        115                 120                 125

Ser

<210> SEQ ID NO 127
<211> LENGTH: 125
<212> TYPE: PRT
<213> ORGANISM: Camelus bactrianus

<400> SEQUENCE: 127

Gln Val Gln Leu Gln Glu Ser Gly Gly Gly Leu Val Gln Ala Gly Gly
1               5                   10                  15

Ser Leu Thr Leu Ser Cys Arg Gly Ser Gly Phe Thr Asn Thr Cys
            20                  25                  30

Ala Met Ala Trp Phe Arg Gln Ala Pro Gly Lys Glu Arg Glu Phe Val
        35                  40                  45

Ser Ser Met Ser Thr Val Gly Ser Thr Arg Phe Ala Asp Ser Val Lys
    50                  55                  60

Gly Arg Phe Thr Ile Ser Lys Asp Glu Ala Lys Asp Thr Val Tyr Leu
65                  70                  75                  80

Gln Met Asn Ser Leu Lys Pro Glu Asp Thr Ala Met Tyr Phe Cys Lys
                85                  90                  95

Thr Tyr Ala Cys Arg Glu Cys Thr Gly Arg Tyr Cys Arg Thr Ala Pro
            100                 105                 110

Asp Ala Trp Gly Gln Gly Thr Gln Val Thr Val Ser Ser
        115                 120                 125

<210> SEQ ID NO 128
<211> LENGTH: 125
<212> TYPE: PRT
<213> ORGANISM: Camelus bactrianus

<400> SEQUENCE: 128

Gln Val Gln Leu Gln Glu Ser Gly Gly Gly Ser Val Gln Ala Gly Gly
```

-continued

```
                1               5                   10                  15
Ser Leu Arg Leu Ser Cys Thr Ala Pro Gly Phe Thr Ser Asn Thr Cys
                20                  25                  30
Ala Met Ala Trp Phe Arg Gln Ala Pro Gly Lys Glu Arg Glu Phe Val
                35                  40                  45
Ser Ser Met Ser Thr Gly Gly Thr Thr Gly Tyr Gly Asp Ser Val Lys
                50                  55                  60
Gly Arg Phe Thr Ser Ser Lys Asp Ala Ala Lys Asp Thr Val Tyr Leu
65                              70                  75                  80
Gln Met Asn Ser Leu Lys Pro Glu Asp Thr Ala Ile Tyr Phe Cys Lys
                85                  90                  95
Thr Tyr Ala Cys Arg Asp Cys Ile Gly Arg Tyr Cys Arg Thr Ala Pro
                100                 105                 110
Asp Ala Trp Gly Gln Gly Thr Gln Val Thr Val Ser Ser
                115                 120                 125
```

<210> SEQ ID NO 129
<211> LENGTH: 125
<212> TYPE: PRT
<213> ORGANISM: Camelus bactrianus

<400> SEQUENCE: 129

```
Gln Val Gln Leu Gln Glu Ser Gly Gly Gly Ser Val Gln Ala Gly Gly
1               5                   10                  15
Ser Leu Arg Leu Ser Cys Thr Ala Pro Gly Phe Thr Ser Asn Thr Cys
                20                  25                  30
Ala Met Ala Trp Tyr Arg Gln Ala Pro Gly Lys Glu Arg Glu Phe Val
                35                  40                  45
Ser Ser Arg Ser Thr Val Gly Thr Thr Gly Tyr Ala Asp Ser Val Lys
                50                  55                  60
Gly Arg Phe Thr Leu Ser Lys Asp Glu Ala Lys Asp Thr Val Tyr Leu
65                              70                  75                  80
Gln Met Asn Ser Leu Lys Pro Glu Asp Thr Ala Met Tyr Phe Cys Lys
                85                  90                  95
Thr Tyr Ala Cys Arg Asn Cys Ile Gly Arg His Cys Arg Thr Ala Pro
                100                 105                 110
Asp Ala Trp Gly Gln Gly Thr Gln Val Thr Val Ser Ser
                115                 120                 125
```

<210> SEQ ID NO 130
<211> LENGTH: 126
<212> TYPE: PRT
<213> ORGANISM: Camelus bactrianus

<400> SEQUENCE: 130

```
Gln Val Gln Leu Gln Glu Ser Gly Gly Gly Ser Val Gln Ala Gly Glu
1               5                   10                  15
Thr Leu Arg Leu Ser Cys Thr Val Ser Gly Asp Thr Phe Glu Ala Ser
                20                  25                  30
Gly Val Gly Trp Phe Arg Gln Val Ser Gly Asn Glu Cys Asp Leu Val
                35                  40                  45
Ser Ser Ile Asn Arg Asp Gly Thr Thr Tyr Tyr Thr Pro Ser Val Ala
                50                  55                  60
Gly Arg Phe Thr Met Ser Gln Asn Asn Ala Lys Asn Thr Val Tyr Leu
65                              70                  75                  80
Gln Met Asn Ser Leu Lys Pro Asp Asp Thr Ala Val Tyr Tyr Cys Ala
```

-continued

```
                85                  90                  95
Thr Asp Pro Ala Val Gly Ile Val Val Arg Ser Thr Cys Arg Gly Pro
            100                 105                 110
Phe Gly Tyr Trp Gly Gln Gly Thr Gln Val Thr Val Ser Ser
            115                 120                 125

<210> SEQ ID NO 131
<211> LENGTH: 126
<212> TYPE: PRT
<213> ORGANISM: Camelus bactrianus

<400> SEQUENCE: 131

Gln Val Gln Leu Gln Glu Ser Gly Gly Gly Ser Val Gln Ala Gly Gly
1               5                   10                  15
Ser Leu Arg Leu Ser Cys Thr Val Ser Gly Asn Thr Asp Ser Met Asn
            20                  25                  30
Leu Met Gly Trp Phe Arg Gln Ala Pro Gly Lys Glu Arg Glu Gly Val
            35                  40                  45
Ala Ser Ile Tyr Thr Gly Ser Arg Thr Ile Thr Tyr Pro Asp Ser Val
    50                  55                  60
Lys Gly Arg Phe Thr Ile Ser Gln Asp Asn Ala Lys Asn Thr Val Tyr
65                  70                  75                  80
Leu Gln Met Asn Ser Leu Lys Pro Glu Asp Thr Ala Met Tyr Tyr Cys
                85                  90                  95
Ala Ala Asp Tyr Arg Ala Arg Tyr Gly Ala Ser Leu Arg Thr Ser Ala
            100                 105                 110
Tyr Thr Tyr Trp Gly Gln Gly Thr Gln Val Thr Val Ser Ser
            115                 120                 125

<210> SEQ ID NO 132
<211> LENGTH: 125
<212> TYPE: PRT
<213> ORGANISM: Camelus bactrianus

<400> SEQUENCE: 132

Gln Val Gln Leu Gln Glu Ser Gly Gly Gly Ser Val Gln Ala Gly Gly
1               5                   10                  15
Ser Leu Arg Leu Ser Cys Thr Ala Pro Gly Phe Thr Ser Asn Thr Cys
            20                  25                  30
Ala Met Ala Trp Tyr Arg Gln Ala Pro Gly Lys Glu Arg Glu Phe Val
            35                  40                  45
Ser Ser Arg Ser Thr Val Gly Thr Thr Gly Tyr Ala Asp Ser Val Lys
    50                  55                  60
Gly Arg Phe Thr Ile Ser Lys Asp Glu Ala Lys Asp Thr Val Tyr Leu
65                  70                  75                  80
Gln Met Asn Ser Leu Lys Pro Glu Asp Thr Ala Lys Tyr Phe Cys Lys
                85                  90                  95
Thr Tyr Ala Cys Arg Asp Cys Ile Gly Arg Tyr Cys Arg Thr Ala Pro
            100                 105                 110
Asp Ala Trp Gly Gln Gly Thr Gln Val Thr Val Ser Ser
            115                 120                 125

<210> SEQ ID NO 133
<211> LENGTH: 124
<212> TYPE: PRT
<213> ORGANISM: Camelus bactrianus

<400> SEQUENCE: 133
```

Gln Val Gln Leu Gln Glu Ser Gly Gly Gly Ser Val Gln Ala Gly Gly
1               5                   10                  15

Ser Leu Lys Leu Ser Cys Val Val Ser Gly Tyr Thr Trp Cys Arg Tyr
            20                  25                  30

Asp Met Ser Trp Tyr Arg Gln Ala Pro Gly Lys Glu Arg Glu Phe Val
        35                  40                  45

Ser Val Ile Asp Asp Asn Gly Ser Thr Asn Tyr Ala Asp Ser Val Lys
    50                  55                  60

Gly Arg Phe Thr Ile Ser Lys Asp Asn Gly Asn Thr Val Thr Leu Gln
65                  70                  75                  80

Met Thr Ser Leu Lys Pro Ala Asp Thr Ala Met Tyr Tyr Cys Gln Thr
                85                  90                  95

Gly Arg Tyr Arg Ser Arg Leu Gly Tyr Gly Arg Cys Pro Ser Gly Asp
            100                 105                 110

Tyr Trp Gly Leu Gly Thr Gln Val Thr Val Ser Ser
        115                 120

<210> SEQ ID NO 134
<211> LENGTH: 124
<212> TYPE: PRT
<213> ORGANISM: Camelus bactrianus

<400> SEQUENCE: 134

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Ser Ile Ser Asn Tyr
            20                  25                  30

Cys Met Gly Trp Phe Arg Gln Pro Pro Gly Lys Glu Arg Glu Gly Val
        35                  40                  45

Ala Asn Ile Asp Thr Trp Gly Val Thr Ser Tyr Thr Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Leu Tyr Tyr Cys Ala
                85                  90                  95

Arg Arg Gln Phe Val Asn Cys Gly Thr Leu Ala Pro Val Asn Tyr Val
            100                 105                 110

Asn Trp Gly Gln Gly Thr Gln Val Thr Val Ser Ser
        115                 120

<210> SEQ ID NO 135
<211> LENGTH: 121
<212> TYPE: PRT
<213> ORGANISM: Camelus bactrianus

<400> SEQUENCE: 135

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Ser Thr Leu
            20                  25                  30

Ala Met Ser Trp Val Arg Gln Ala Pro Gly Lys Gly Leu Glu Trp Val
        35                  40                  45

Ser Thr Ile Ser Ser Thr Gly Gly Ala Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

-continued

Leu Gln Leu Asn Ser Leu Lys Pro Glu Asp Thr Ala Met Tyr Tyr Cys
                85                  90                  95

Arg Arg Cys Thr Asp Ile Tyr Cys Ser Asn Ser Ala Arg Trp Thr Gly
            100                 105                 110

Gln Gly Thr Gln Val Thr Val Ser Ser
        115                 120

<210> SEQ ID NO 136
<211> LENGTH: 121
<212> TYPE: PRT
<213> ORGANISM: Camelus bactrianus

<400> SEQUENCE: 136

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Thr Phe Ser Thr Leu
            20                  25                  30

Ala Met Ser Trp Val Arg Gln Ala Pro Gly Lys Gly Leu Glu Trp Val
        35                  40                  45

Ser Thr Ile Ser Ser Thr Gly Gly Ala Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Lys Pro Glu Asp Thr Ala Met Tyr Tyr Cys
                85                  90                  95

Arg Arg Cys Thr Asp Ile Tyr Cys Ser Asn Ser Ala Arg Trp Thr Gly
            100                 105                 110

Gln Gly Thr Gln Val Thr Val Ser Ser
        115                 120

<210> SEQ ID NO 137
<211> LENGTH: 120
<212> TYPE: PRT
<213> ORGANISM: Camelus bactrianus

<400> SEQUENCE: 137

Gln Val Gln Leu Gln Glu Ser Gly Gly Gly Leu Val Gln Pro Gly Gly
1               5                   10                  15

Ser Leu Arg Leu Ser Cys Val Ala Ser Gly Phe Ser Phe Ser Ser Ser
            20                  25                  30

Gly Met Ser Trp Val Arg Gln Ala Pro Gly Lys Gly Leu Glu Trp Val
        35                  40                  45

Ser Thr Ile Ser Tyr Asn Gly Gly Ser Thr Phe Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Lys Thr Glu Asp Thr Ala Met Tyr Tyr Cys
                85                  90                  95

Ala Lys Ser Gly Thr Pro Val Leu Ala Pro Asn Ser Val Arg Gly Gln
            100                 105                 110

Gly Thr Gln Val Thr Val Ser Ser
        115                 120

<210> SEQ ID NO 138
<211> LENGTH: 127
<212> TYPE: PRT
<213> ORGANISM: Camelus bactrianus

<400> SEQUENCE: 138

```
Gln Val Gln Leu Gln Glu Ser Gly Gly Gly Ser Val Gln Ala Gly Gly
1               5                   10                  15

Ser Leu Arg Leu Ser Cys Val Ser Ser Gly Tyr Ala Tyr Asn Arg Tyr
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125
```

<210> SEQ ID NO 139
<211> LENGTH: 122
<212> TYPE: PRT
<213> ORGANISM: Camelus bactrianus

<400> SEQUENCE: 139

```
Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asn Cys Arg Tyr
            20                  25                  30

Asp Met Ser Trp Tyr Arg Gln Ala Pro Gly Lys Glu Arg Glu Phe Val
        35                  40                  45

Ser Ser Ile Asp Ser Glu Gly Val Ala Arg His Ala Asp Ser Val Lys
    50                  55                  60

Gly Arg Phe Gly Ile Ser Gln Asp Asn Ala Lys Ser Thr Leu Tyr Leu
65                  70                  75                  80

Gln Met Asn Ser Leu Lys Pro Glu Asp Thr Ala Val Tyr Tyr Cys Lys
                85                  90                  95

Thr Asp Tyr Ile Thr Cys Arg Phe Gly Ser Trp Ser Asp Ser Thr Trp
            100                 105                 110

Gly Gln Gly Thr Gln Val Thr Val Ser Ser
        115                 120
```

<210> SEQ ID NO 140
<211> LENGTH: 122
<212> TYPE: PRT
<213> ORGANISM: Camelus bactrianus

<400> SEQUENCE: 140

```
Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asn Cys Arg Tyr
            20                  25                  30

Asp Met Ser Trp Tyr Arg Gln Ala Pro Gly Lys Glu Arg Glu Phe Val
        35                  40                  45

Ser Ser Ile Asp Ser Glu Gly Val Ala Arg His Ala Asp Ser Val Lys
    50                  55                  60
```

```
Gly Arg Phe Gly Ile Ser Gln Asp Asn Ala Lys Ser Thr Leu Tyr Leu
 65                  70                  75                  80

Gln Met Asn Ser Leu Lys Pro Glu Asp Thr Ala Met Tyr Tyr Cys Lys
                 85                  90                  95

Met Asp Tyr Ile Arg Cys Arg Phe Gly Ser Trp Ser Glu Ser Thr Trp
                100                 105                 110

Gly Gln Gly Thr Gln Val Thr Val Ser Ser
            115                 120
```

<210> SEQ ID NO 141
<211> LENGTH: 125
<212> TYPE: PRT
<213> ORGANISM: Camelus bactrianus

<400> SEQUENCE: 141

```
Gln Val Gln Leu Gln Glu Ser Gly Gly Gly Ser Val Gln Ala Gly Gly
  1               5                  10                  15

Ser Leu Arg Leu Ser Cys Thr Ala Pro Gly Phe Thr Ser Asn Thr Cys
                 20                  25                  30

Ala Met Ala Trp Phe Arg Gln Ala Pro Gly Lys Glu Arg Glu Phe Val
                 35                  40                  45

Ser Ser Met Ser Thr Val Gly Ser Thr Arg Phe Ala Asp Ser Val Lys
 50                  55                  60

Gly Arg Phe Thr Ile Ser Lys Asp Glu Ala Lys Asp Thr Val Tyr Leu
 65                  70                  75                  80

Gln Met Asn Ser Leu Lys Pro Glu Asp Thr Ala Met Tyr Phe Cys Lys
                 85                  90                  95

Thr Tyr Ala Cys Arg Glu Cys Thr Gly Arg Tyr Cys Arg Thr Ala Pro
                100                 105                 110

Asp Ala Trp Gly Gln Gly Thr Gln Val Thr Val Ser Ser
                115                 120                 125
```

<210> SEQ ID NO 142
<211> LENGTH: 129
<212> TYPE: PRT
<213> ORGANISM: Camelus bactrianus

<400> SEQUENCE: 142

```
Gln Val Gln Leu Gln Glu Ser Gly Gly Gly Ser Val Gln Thr Gly Gly
  1               5                  10                  15

Ser Leu Arg Leu Ser Cys Ala Val Ser Arg Tyr Ser Ala Ser Asn Asn
                 20                  25                  30

Val Ile Lys Trp Met Gly Trp Phe Arg Gln Ala Pro Gly Lys Glu Arg
                 35                  40                  45

Glu Gly Val Ala Ala Leu Tyr Thr Ser Gly Gly Asn Thr Tyr Tyr Ala
 50                  55                  60

Asp Ser Val Lys Gly Arg Phe Thr Ile Ser Arg Asp Tyr Ser Glu Asn
 65                  70                  75                  80

Thr Val Ser Leu Gln Met Asn Asn Leu Lys Pro Glu Asp Thr Gly Met
                 85                  90                  95

Tyr Tyr Cys Ala Ala Thr Val Gly Thr Val Leu Ala Gly Pro Leu Ser
                100                 105                 110

Ala Arg Lys Tyr Asn Tyr Trp Gly Gln Gly Thr Gln Val Thr Val Ser
                115                 120                 125

Ser
```

-continued

<210> SEQ ID NO 143
<211> LENGTH: 125
<212> TYPE: PRT
<213> ORGANISM: Camelus bactrianus

<400> SEQUENCE: 143

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Tyr Arg Gln Ala Pro Gly Lys Glu Arg Glu Phe Val
        35                  40                  45

Ser Ser Ile Ser Thr Val Arg Thr Thr Ala Tyr Ala Asp Ser Val Lys
    50                  55                  60

Gly Arg Phe Thr Ile Ser Lys Asp Glu Ala Lys Ala Thr Val Tyr Leu
65                  70                  75                  80

Gln Met Asn Ser Leu Lys Pro Glu Asp Thr Ala Met Tyr Phe Cys Lys
                85                  90                  95

Ser Tyr Ala Cys Arg Asp Cys Ile Gly Arg Tyr Cys Arg Thr Ala Pro
            100                 105                 110

Asp Ala Trp Gly Gln Gly Thr Gln Val Thr Val Ser Ser
        115                 120                 125

<210> SEQ ID NO 144
<211> LENGTH: 129
<212> TYPE: PRT
<213> ORGANISM: Camelus bactrianus

<400> SEQUENCE: 144

Gln Val Gln Leu Gln Glu Ser Gly Gly Gly Ser Val Gln Ala Gly Gln
1               5                   10                  15

Ser Leu Arg Leu Ser Cys Thr Ala Ser Gly Tyr Thr Asp Ser Arg Tyr
            20                  25                  30

Cys Met Gly Trp Phe Arg Gln Ala Pro Gly Lys Glu Arg Glu Arg Val
        35                  40                  45

Thr Thr Ile His Thr Gly Thr Gly Ile Thr Tyr Ala Asp Ser Val
    50                  55                  60

Lys Gly Arg Phe Ser Ile Ser Gln Asp Asn Ala Gln Asn Thr Met Tyr
65                  70                  75                  80

Leu Gln Met Asn Ser Leu Glu Pro Glu Asp Thr Ala Met Tyr Tyr Cys
                85                  90                  95

Ala Thr Thr Asp Tyr Val Tyr Ser Ala Ser Ala Ser Trp Cys Asn Gly
            100                 105                 110

Tyr Gly Val Phe Asn Asn Trp Gly Gln Gly Thr Gln Val Thr Val Ser
        115                 120                 125

Ser

<210> SEQ ID NO 145
<211> LENGTH: 125
<212> TYPE: PRT
<213> ORGANISM: Camelus bactrianus

<400> SEQUENCE: 145

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

```
Ala Met Ala Trp Tyr Arg Gln Ala Pro Gly Lys Glu Arg Glu Phe Val
            35                  40                  45

Ser Ser Arg Ser Thr Val Gly Thr Thr Gly Tyr Ala Asp Ser Val Lys
 50                      55                  60

Gly Arg Phe Thr Ile Ser Lys Asp Glu Ala Lys Asp Thr Val Tyr Leu
 65                  70                  75                  80

Gln Met Asn Ser Leu Lys Pro Glu Asp Thr Ala Lys Tyr Phe Cys Lys
                 85                  90                  95

Thr Tyr Ala Cys Arg Asp Cys Ile Gly Arg Tyr Cys Arg Thr Ala Pro
            100                 105                 110

Asp Ala Trp Gly Gln Gly Thr Gln Val Thr Val Ser Ser
            115                 120                 125
```

<210> SEQ ID NO 146
<211> LENGTH: 129
<212> TYPE: PRT
<213> ORGANISM: Camelus bactrianus

<400> SEQUENCE: 146

```
Gln Val Gln Leu Gln Glu Ser Gly Gly Gly Ser Val Gln Ala Gly Gly
 1               5                  10                  15

Ser Leu Arg Leu Ser Cys Ala Val Ser Arg Tyr Ser Ala Ser Asn Asn
            20                  25                  30

Val Ile Lys Trp Met Gly Trp Phe Arg Gln Ala Pro Gly Lys Glu Arg
            35                  40                  45

Glu Gly Val Ala Ala Leu Tyr Thr Ser Gly Gly Asn Thr Tyr Tyr Ala
 50                      55                  60

Asp Ser Val Lys Gly Arg Phe Thr Ile Ser Arg Asp Tyr Ser Glu Asn
 65                  70                  75                  80

Thr Val Ser Leu Gln Met Asn Asn Leu Lys Pro Glu Asp Thr Gly Met
                 85                  90                  95

Tyr Tyr Cys Ala Thr Thr Val Gly Thr Val Leu Ala Gly Pro Leu Ser
            100                 105                 110

Ala Arg Lys Tyr Asn Tyr Trp Gly Gln Gly Thr Gln Val Thr Val Ser
            115                 120                 125

Ser
```

<210> SEQ ID NO 147
<211> LENGTH: 124
<212> TYPE: PRT
<213> ORGANISM: Camelus bactrianus

<400> SEQUENCE: 147

```
Gln Val Gln Leu Gln Glu Ser Gly Gly Gly Ser Val Gln Ala Gly Gly
 1               5                  10                  15

Ser Leu Arg Leu Ser Cys Ala Ala Ser Gly Tyr Thr Ser Arg Pro Asn
            20                  25                  30

Phe Met Val Trp Phe Arg Gln Ala Pro Gly Lys Glu Arg Glu Ala Val
            35                  40                  45

Ala Gly Ile Tyr Thr Val Thr Gly Gly Thr Leu Tyr Ser Asp Pro Val
 50                      55                  60

Lys Gly Arg Phe Thr Ile Ser Gln Asp Lys Ala Lys Asn Thr Val Tyr
 65                  70                  75                  80

Leu Gln Met Asn Ser Leu Asn Pro Glu Asp Thr Ala Met Tyr Tyr Cys
                 85                  90                  95

Ala Val Lys Trp Tyr Gly Gly Ser Trp Ser Asp Ala Ala Thr Phe Arg
```

```
                    100                 105                 110
Thr Trp Gly Arg Gly Thr Gln Val Thr Val Ser Ser
        115                 120

<210> SEQ ID NO 148
<211> LENGTH: 125
<212> TYPE: PRT
<213> ORGANISM: Camelus bactrianus

<400> SEQUENCE: 148

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ser Tyr Asn Ile Asp
            20                  25                  30

Tyr Met Ala Trp Phe Arg Gln Ala Pro Gly Lys Glu Arg Glu Gly Val
        35                  40                  45

Ala Ala Ile Tyr Thr Gly Ser Arg Arg Thr Tyr Tyr Ser Asp Ser Val
    50                  55                  60

Lys Gly Arg Phe Ala Ile Ser Gln Asp Asn Ala Asp Asn Thr Val Tyr
65                  70                  75                  80

Leu Gln Met Asn Ala Leu Lys Pro Glu Asp Thr Ala Met Tyr Phe Cys
                85                  90                  95

Ala Ala Leu Val Ser Arg Pro Gly Arg Ser Trp Asp Lys Asn Glu Tyr
            100                 105                 110

Arg Tyr Trp Gly Gln Gly Thr Gln Val Thr Val Ser Ser
        115                 120                 125

<210> SEQ ID NO 149
<211> LENGTH: 125
<212> TYPE: PRT
<213> ORGANISM: Camelus bactrianus

<400> SEQUENCE: 149

Gln Val Gln Leu Gln Glu Ser Gly Gly Gly Leu Val Gln Ala Gly Gly
1               5                   10                  15

Ser Leu Arg Leu Ser Cys Thr Ala Ser Gly Phe Thr Phe Asp Asp Tyr
            20                  25                  30

Ser Met Gly Trp Phe Arg Gln Ala Pro Gly Lys Glu Arg Glu Gly Ile
        35                  40                  45

Ser Cys Ile Asp Trp Ser Gly Arg Thr Asn Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asn Ser Ala Tyr Ser Ser Cys Ser Leu Ser Thr Thr His Tyr
            100                 105                 110

Lys Tyr Trp Gly Gln Gly Thr Gln Val Thr Val Ser Ser
        115                 120                 125

<210> SEQ ID NO 150
<211> LENGTH: 121
<212> TYPE: PRT
<213> ORGANISM: Camelus bactrianus

<400> SEQUENCE: 150

Gln Val Gln Leu Gln Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ala Tyr
         20                  25                  30

Gly Met Ser Trp Val Arg Gln Ala Pro Gly Lys Gly Phe Glu Trp Val
         35                  40                  45

Ser Thr Ile Asn Ser Gly Gly Thr Thr Phe Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Leu Asn Ser Leu Arg Thr Glu Asp Thr Ala Met Tyr Tyr Cys
                 85                  90                  95

Arg Arg Cys Ala Asp Ile Tyr Cys Ser Leu Ser Gly Gly Trp Thr Gly
                100                 105                 110

Gln Gly Thr Gln Val Thr Val Ser Ser
        115                 120
```

<210> SEQ ID NO 151
<211> LENGTH: 381
<212> TYPE: DNA
<213> ORGANISM: Camelus bactrianus

<400> SEQUENCE: 151

```
caggtgcagc tgcaggagtc tggaggaggc tcggtgcaga ccggagggtc tctgagactc      60
tcctgtacag cctctacatc aatatacagt aacaactaca tggcctggtt cagccagtct     120
ccaggaaagg ggcgcgaggg ggtcgcagct gtttatatgg atgatggtcg cccatactat     180
gccgattccg tgaagggccg attcaccatc tccctagaca cgccaagaa cacgatgtat      240 ttgcaaatga acagcctgaa acctgaggac actgccatgt actactgtgc ggcagctcca     300
ggccccttaa gtcgtaacta ctggtacacg tccgccaact atgactactg gggccagggg     360
acccaggtca ccgtctcctc a                                                381
```

<210> SEQ ID NO 152
<211> LENGTH: 378
<212> TYPE: DNA
<213> ORGANISM: Camelus bactrianus

<400> SEQUENCE: 152

```
caggtgcagc tgcaggagtc tggaggaggg tcggtgcagg ctggagagac tctgagactc      60
tcctgtacag cctctggaga cttttgat gactctggcg tgggctggtt ccgccaggtt      120
tcagggaatg agtgcgactt ggtctcaagt attaatcgtg atggtaacac atactataca     180
ccctccgtgg cgggccgatt taccatctcc caaaacaacg ccaagaacac ggtatatctg     240
caaatgaaca gcctgaaacc tgacgacaca gccgtgtatt actgtgcgac agacccccgcc     300 gtggggattg tagtgaggac tacctgtaga ggcccctttg gttactgggg ccaggggacc     360
caggtcaccg tctcctca                                                   378
```

<210> SEQ ID NO 153
<211> LENGTH: 381
<212> TYPE: DNA
<213> ORGANISM: Camelus bactrianus

<400> SEQUENCE: 153

```
caggtgcagc tgcaggagtc tgggggaggc tcggtgcaga ccggagggtc tctgagactc      60
tcctgtgcag cctctacatc actatacagt acaactaca tggcctggtt cagccaggct      120
ccaggaaagg ggcgcgaggg ggtcgcagct gtttatgttg gtgatggtcg cccatactat     180
```

```
gccgactccg tgaagggccg attcaccatc tccctagaca gcgccaagaa cgcggtgtat    240
ctgcaaatga acagcctgaa acctgaggac actgccatgt actactgtgc ggcagctcca    300
ggccccttaa gtcataatta ctggtacacg tccgccaact atgactactg gggccagggg    360
acccaggtca ccgtctcctc a                                              381

<210> SEQ ID NO 154
<211> LENGTH: 381
<212> TYPE: DNA
<213> ORGANISM: Camelus bactrianus

<400> SEQUENCE: 154
caggtgcagc tgcaggagtc tggaggaggc tcggtgcaga ccggagggtc tctgagactc     60
tcctgtgcag cctctccatc aatatacagt gccaactaca tggcctggtt cagccaggct    120
ccaggaaagg ggcgcgaggg ggtcgcagct gtttatattg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttag gtcataatta ctggtacacg tccgccaact atgactactg gggccagggg    360
acccaggtca ccgtctcctc a                                              381

<210> SEQ ID NO 155
<211> LENGTH: 381
<212> TYPE: DNA
<213> ORGANISM: Camelus bactrianus

<400> SEQUENCE: 155
caggtgcagc tgcaggagtc tgggggaggc tcggtgcaga ccggagggtc tctgagactc     60
tcctgtgcag cctctacatc aatatacagt aacaactaca tggcctggtt cagccaggct    120
ccaggaaagg ggcgcgaggg ggtcgcagct gtttacattg atgatggtcg cccatactat    180
gccgactccg tgaagggccg attcaccatc tccctagaca gcgccaagaa cacggtgtat    240
ctgcaaatga acggcctgaa acctgaggac actgccatgt actactgtgc ggcagctcca    300
ggccccttaa gtcgtaatta ctggtacacg tccgccaact atgactactg gggccagggg    360
acccaggtca ccgtctcctc a                                              381

<210> SEQ ID NO 156
<211> LENGTH: 378
<212> TYPE: DNA
<213> ORGANISM: Camelus bactrianus

<400> SEQUENCE: 156
caggtgcagc tgcaggagtc tgggggaggg tcggtgcagg ctggagagac tctgagactc     60
tcctgtacag cctctggaga cacttttgat gcctctggcg tgggctggtt ccgccaggtt    120
tcagggaatg aatgcgactt ggtctcaagt attaatcgtg atggtaccac atactatgca    180
ccctccgtgg cgggccgatt tacgatgtcc caaaacaacg caagaacac ggtatatctg    240 caaatgaaca gcctgaaacc tgacgacaca gccgtgtatt actgtgcgac agaccccgcc    300
gtggggattg tagtgaggag cacctgtaga ggccccttttg gttactgggg caggggacc    360 caggtcaccg tctcctca                                                  378

<210> SEQ ID NO 157
<211> LENGTH: 381
<212> TYPE: DNA
```

<213> ORGANISM: Camelus bactrianus

<400> SEQUENCE: 157

| caggtgcagc | tgcaggagtc | tgggggaggc | tcggtgcaga | ccggagggtc | tctgagactc | 60 |
| tcctgtgcat | gctctacatc | aatatacagt | accaactaca | tggcctggtt | cagccaggct | 120 |
| ccaggaaagg | ggcgcgaggg | ggtcgcagct | gtttatattg | gtgatggtcg | cccatactat | 180 |
| gccgactccg | tgaagggccg | attcaccatc | tccctagaca | cgccaagaa | cacggtgtat | 240 |
| ctgcaaatga | acagcctgaa | acctgaggac | actgccatgt | actactgtgc | ggcagctcca | 300 |
| ggccccttaa | gtcgtaatta | ctggtacacg | tccgccaact | atgactactg | gggccagggg | 360 |
| acccaggtca | ccgtctcctc | a | | | | 381 |

<210> SEQ ID NO 158
<211> LENGTH: 375
<212> TYPE: DNA
<213> ORGANISM: Camelus bactrianus

<400> SEQUENCE: 158

| caggtgcagc | tgcaggagtc | tgggggagac | tcagtgcagg | ctgggggtc | tctgagactc | 60 |
| gcctgcaaag | tccctggatt | cacctccaac | acctgcgcca | tggcgtggtt | ccgccaggct | 120 |
| ccagggaaag | agcgcgagtt | cgtctcatct | atcagcactg | gcggtaccac | ggggtatgca | 180 |
| gaatccgcga | agggccgatt | caccctctcc | aaagacgaag | ccaaggacac | ggtctatctg | 240 |
| caaatgaaca | gcctgaaacc | ggaggacacg | gccatgtatt | tttgtaagag | ctatgcgtgt | 300 |
| agaacttgta | ttggtcggta | ttgtcgtaca | gctccggatg | catggggcca | ggggacacag | 360 |
| gtcaccgtct | cctca | | | | | 375 |

<210> SEQ ID NO 159
<211> LENGTH: 372
<212> TYPE: DNA
<213> ORGANISM: Camelus bactrianus

<400> SEQUENCE: 159

| caggtgcagc | tgcaggagtc | tggaggaggc | tcggtgcagg | ctggagggtc | tctgagactc | 60 |
| tcctgtgcag | cctctggata | tacttacagt | aacgacggta | tgggctggtt | ccgccagatt | 120 |
| ccagggaagg | agcgcgaggg | ggtcgcagct | attagtccta | ctggtaggcg | cacagagtat | 180 |
| gccgactccg | tgcagggccg | attcaccatc | tcccgcgaca | acgccaagaa | catgttatct | 240 |
| ctgcaaatga | acagcctgaa | acctgaggac | actgggatgt | actactgtgc | acgcgagggg | 300 |
| tcggggtcct | tttccctgca | aaatagcgcg | gtgagatcgt | ggggccaggg | gacccaggtc | 360 |
| accgtctcct | ca | | | | | 372 |

<210> SEQ ID NO 160
<211> LENGTH: 375
<212> TYPE: DNA
<213> ORGANISM: Camelus bactrianus

<400> SEQUENCE: 160

| caggtgcagc | tgcaggagtc | tgggggaggc | tcagtgcagg | ctgggggtc | tctgagactc | 60 |
| tcctgcacag | cccctggatt | cacctccaag | acctgcgcca | tgcgctggta | ccgccaggct | 120 |
| ccagggaaag | agcgcgagtt | cgtctcagca | atcagcactg | tcggtaccac | aacgtatgca | 180 |
| gactccgtga | agggccgatt | cattatctcc | aaagacgaag | ccaaggacac | ggtctatctg | 240 |
| caaataaaca | gcctgaaacc | tgaggacact | gccatgtatt | cttgtaagac | ctttgcgtgt | 300 |

```
agacattgta ttggtcaatc ttgtcgtaca gaaccggatt attggggcca ggggacacag    360
gtcaccgtct cctca                                                     375
```

<210> SEQ ID NO 161
<211> LENGTH: 378
<212> TYPE: DNA
<213> ORGANISM: Camelus bactrianus

<400> SEQUENCE: 161

```
caggtgcagc tgcaggagtc tgggggaggg tcggtgcagg ctggagagac tctgagactc     60
tcctgtacag cctctggaga cacttttgat gactctggcg tgggctggtt ccgccaggtt    120
tcagggaatg aatgcgactt ggtctcaagt attaatcgtg atggtaccac atactatgca    180
ccctccgtgg cgggccgatt taccatctcc aaaacaacg ccaagaacac ggtatatctg     240
caaatgaaca gcctgaaacc tgacgacaca gccgtgtatt actgtgcgac agtccccgcc    300
gtggggattg tagtgaggat tacctgtaga ggcccctttg gttactgggg caggggacc     360 caggtcaccg tctcctca                                                  378
```

<210> SEQ ID NO 162
<211> LENGTH: 381
<212> TYPE: DNA
<213> ORGANISM: Camelus bactrianus

<400> SEQUENCE: 162

```
caggtgcagc tgcaggagtc tgggggaggc tcggtgcagg ctggagggtc cctgagactc     60
tcctgtgcag cctctggata cacccgcagt agtcactgca tggtctggtt ccgtcaggct    120
ccagggaagg agcgcgaggg ggtcgctctt atttatactg gtagtggttc aacatactat    180
gccgactccg tgaagggccg attcaccatc tcccaagaca cgccaagaa gacgctgtat     240 ctgcaaatga acagcctgaa acctgaggac actgccatgt attactgtgc ggcaggaacg    300
agttcatcat cctgccccgg cctcttgggc cctccgaggt attacaactg gggccagggg    360
acccaggtca ccgtctcctc a                                              381
```

<210> SEQ ID NO 163
<211> LENGTH: 381
<212> TYPE: DNA
<213> ORGANISM: Camelus bactrianus

<400> SEQUENCE: 163

```
caggtgcagc tgcaggagtc tgggggaggc tcggtgcaga ccggagggtc tctgagactc     60
tcctgtgcag cctctacatc aatatacagt aacaactaca tggcctggtt cagccagaat    120
ccaggaaagg ggcgcgaggg ggtcgcagct gtttatattg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
gggcccttaa gtcgaaatta ctggtacacg tccgccaact atgactactg gggccagggg    360
acccaggtca ccgtctcctc a                                              381
```

<210> SEQ ID NO 164
<211> LENGTH: 381
<212> TYPE: DNA
<213> ORGANISM: Camelus bactrianus

<400> SEQUENCE: 164

```
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttatattg atgatggtcg cccatactat     180
gccgactccg tgaagggccg attcaccatc tccctagaca cgccaagaa cacggtgtat      240 ctgcaagtga acagcctgaa acctgaggac actgccatgt actactgtgc ggcagctcca     300
ggccccttaa gtcgtaatta ctggtacacg tccgccaact atgactactg gggccagggg    360
acccaggtca ccgtctcctc a                                               381
```

<210> SEQ ID NO 165
<211> LENGTH: 381
<212> TYPE: DNA
<213> ORGANISM: Camelus bactrianus

<400> SEQUENCE: 165

```
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttatattg atgatggtcg cacatactat     180
gccgactccg tgaagggccg attcaccatc tccctagaca cgccaagaa cacggtgtat      240 ctgcaaatga acagcctgaa acctgaggac actgccatgt actactgtgc ggcagctcca     300
ggccccttaa gttataatta ctggtacacg tccgccaact atgactactg gggccagggg    360
acccaggtca ccgtctcctc a                                               381
```

<210> SEQ ID NO 166
<211> LENGTH: 381
<212> TYPE: DNA
<213> ORGANISM: Camelus bactrianus

<400> SEQUENCE: 166

```
caggtgcagc tgcaggagtc tgggggaggc tcggtgcaga ccggagggtc tctgagactc      60
tcctgtgcag cctcgccatc aatatacagt aacaactaca tggcctggtt cagccaggct     120
ccaggaaagg ggcgcgaggg ggtcgcagct gtttatattg gtgatggtcg cccatactat     180
gccgactccg tgaagggccg attcaccatc tccctagaca cgccaagaa cacggtgtat      240 ctgcaaatga acagcctgaa acctgaggac actgccatgt actactgtgc ggcagctcca     300
ggccccttaa gtcgtaatta ctggtacacg tccgccaact atgactactg gggccagggg    360
acccaggtca ccgtctcctc a                                               381
```

<210> SEQ ID NO 167
<211> LENGTH: 381
<212> TYPE: DNA
<213> ORGANISM: Camelus bactrianus

<400> SEQUENCE: 167

```
caggtgcagc tgcaggagtc tgaggaggc tcggtgcaga ccggagggtc tctgagactc       60
tcctgtgcag cctctacatc aatatacagt ctcaactaca tggcctggtt cagccaggct     120
ccaggaaagg ggcgcgaggg ggtcgcagct gtttatattg atgatggtcg cccatactat     180
gccgatcacg tgaagggccg attcaccatc tccctagaca ccgccaagaa cacggtgtat     240
ttgcaaatga acagcctgaa acctgaggac actgccatgt actactgtgc ggcagctcca     300
ggccccttaa gtcgtaacta ctggtacacg tccgccaact atgactactg gggccagggg    360
acccaggtca ccgtctcctc a                                               381
```

```
<210> SEQ ID NO 168
<211> LENGTH: 372
<212> TYPE: DNA
<213> ORGANISM: Camelus bactrianus

<400> SEQUENCE: 168
caggtgcagc tgcaggagtc tgggggaggc tcggtgcagg ctggagggtc tctgagactc      60
tcctgtgcag cctctggata tacttacagt agcgacggta tgggctggtt ccgccagact     120
ccagggaagg agcgcgaggg ggtcgcagct attagtccta ccggtaggcg cacagagtat     180
gccgactccg tgaagggccg attcaccatc tcccgcgaca caacaagaa catgttatct      240 ctgcaaatga acagcctgaa acctgaggac actgggatgt actactgtgc acgcgagggg    300
tcgtggtcct tttccctggc aaatagcgcg gtgagatcgt ggggccaggg gacccaggtc    360
accgtctcct ca                                                         372

<210> SEQ ID NO 169
<211> LENGTH: 381
<212> TYPE: DNA
<213> ORGANISM: Camelus bactrianus

<400> SEQUENCE: 169
caggtgcagc tgcaggagtc tggaggaggc tcggtgcaga ccggagggtc tctgagactc      60
tcctgtgcag cctctacatc aatatacagt aacaactaca tggcctggtt cagccaggct    120
ccaggaaagg ggcgcgaggg ggtcgcagct gtttatattg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtaatta ctggtacacg tccgccaact atgactactg gggccagggg    360
acccaggtca ccgtctcctc a                                               381

<210> SEQ ID NO 170
<211> LENGTH: 363
<212> TYPE: DNA
<213> ORGANISM: Camelus bactrianus

<400> SEQUENCE: 170
caggtgcagc tgcaggagtc tgggggaggc ttggtgcagc ctgggggtc tctgagactc      60 tcctgtgcag cctctggatt caccggcagt atttatgcca tgagctgggt ccgccaggct    120
ccagggaagg gactcgagtg gtctcaact attagtagta gtggtggtag gcgattctat    180
gcagactccg tgaagggccg attcaccatc tccagagaca cgccaagaa cacgctgtat     240 ctgcaattga acagccttaa aactgaggac acggccatgt attactgtgc aagatgtagt    300
gatatttact gcgacaacgg agcgtcgtat aggggccagg ggacccaggt caccgtctcc    360
tca                                                                   363

<210> SEQ ID NO 171
<211> LENGTH: 381
<212> TYPE: DNA
<213> ORGANISM: Camelus bactrianus

<400> SEQUENCE: 171
caggtgcagc tgcaggagtc tggaggaggc tcggtgcaga ccggagggtc tctgagactc      60
tcctgtgcag cctctacatc aatatacagt ctcaactaca tggcctggtt cagccaggct    120
```

```
ccaggaaagg ggcgcgaggg ggtcgctgct gtttatattg gtgatggtcg cccatactat    180
gccgactccg tgaagggccg attcaccatc tccctagaca gcgccaagaa cacggtgtat    240
ctgcaaatga acagcctgaa atctgaggac actgccatgt actactgtgc ggcagctcca    300
ggccccttaa gtcgtcatta ctggtacacg tccgccaact atgactactg gggccagggg    360
acccaggtca ccgtctcctc a                                              381

<210> SEQ ID NO 172
<211> LENGTH: 381
<212> TYPE: DNA
<213> ORGANISM: Camelus bactrianus

<400> SEQUENCE: 172
caggtgcagc tgcaggagtc tgggggaggc tcggtgcaga ccggagggtc tctgagactc     60
tcctgtgcag cctctacatc aatctacagt aacaactaca tggcctggtt cagccaggct    120
ccaagaaagg ggcgcgaggg ggtcgcagct gtttatattg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcataatta ctggtacacg tccgccaact atgactactg gggccagggg    360
acccaggtca ccgtctcctc a                                              381

<210> SEQ ID NO 173
<211> LENGTH: 381
<212> TYPE: DNA
<213> ORGANISM: Camelus bactrianus

<400> SEQUENCE: 173
caggtgcagc tgcaggagtc tgggggaggc tcggtgcaga ccggagggtc tctgagactc     60
tcctgtgcag cctctacatc actatacagt tacaactaca tggcctggtt cagccaggct    120
ccaggaaagg ggcgcgaggg ggtcgcagct gtttatgttg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcataatta ctggtacacg tccgccaact atgactactg gggccagggg    360
acccaggtca ccgtctcctc a                                              381

<210> SEQ ID NO 174
<211> LENGTH: 381
<212> TYPE: DNA
<213> ORGANISM: Camelus bactrianus

<400> SEQUENCE: 174
caggtgcagc tgcaggagtc tgggggaggc tcggtgcaga ccggagggtc tctgagactc     60
tcctgtacag cctctacatc aatatacagt aacaactaca tggcctggtt cagccagtct    120
ccaggaaagg ggcgcgaggg ggtcgcagct gtttatatgg atgatggtcg cccatactat    180
gccgattccg tgaagggccg attcaccatc tccctagaca gcgccaagaa cacgatgtat    240
ctgcaaatga acagcctgaa acctgaggac actgccatgt actactgtgc ggcagctcca    300
ggccccttaa gtcgtaacta ctggtacacg tccgccaact atgactactg gggccagggg    360
acccaggtca ccgtctcctc a                                              381

<210> SEQ ID NO 175
<211> LENGTH: 381
```

```
<212> TYPE: DNA
<213> ORGANISM: Camelus bactrianus

<400> SEQUENCE: 175
caggtgcagc tgcaggagtc tggaggaggc tcggtgcaga ccggagggtc tctgagactc      60
tcctgtacag cctctacatc aatatacagt aacaactaca tggcctggtt cagccaggct     120
ccaggaaagg ggcgcgaggg ggtcgcagct gtttatattg gtgatggtcg accatactat     180
gccgactccg tgaagggccg attcaccatc tccctagaca gcgccaagaa cacggtgtat     240
ctgcaaatga acagcctgaa acctgaggac actgccatgt actactgtgc ggcagctcca     300
ggccccttaa gtcataatta ctggtacacg tctgccaact atgactactg gggccagggg     360
acccaggtca ccgtctcctc a                                                381

<210> SEQ ID NO 176
<211> LENGTH: 381
<212> TYPE: DNA
<213> ORGANISM: Camelus bactrianus

<400> SEQUENCE: 176
caggtgcagc tgcaggagtc tgggggaggc tcggtgcaga ccggagggtc tctgagactc      60
tcctgtgcag cctctacatc aatatacaat aacaactaca tggcctggtt cagccaggct     120
ccaggaaagg agcgcgaggg ggtcgcagct gtttatattg gtgatggtcg cccatactat     180
gccgactccg tgaagggccg attcaccatc tccctagaca gcgccaagaa cacggtgtat     240
ctgcaaatga acagcctgaa acctgaggac actgccatgt actactgtgc ggcagctcca     300
ggccccttaa gtcgtaatta ctggtacacg tccgccaact atgactactg gggccagggg     360
acccaggtca ccgtctcctc a                                                381

<210> SEQ ID NO 177
<211> LENGTH: 381
<212> TYPE: DNA
<213> ORGANISM: Camelus bactrianus

<400> SEQUENCE: 177
caggtgcagc tgcaggagtc tgggggaggc tcggtgcaga ccggagggtc tctgagactc      60
tcctgtacag cctctacatc aatatacagt aacaactaca tggcctggtt cagccagtct     120
ccaggaaagg ggcgcgaggg ggtcgcagct gtttatattg gatgatggtcg cccatactat    180 gccgattccg tgaagggccg attcaccatc tccctagaca gcgccaagaa cacgatgtat     240
ttgcaaatga acagcctgaa acctgaggac actgccatgt actactgtgc ggcagctcca     300
ggccccttaa gtcgtaacta ctggtacacg tccgccaact atgactactg gggccagggg     360
acccaggtca ccgtctcctc a                                                381

<210> SEQ ID NO 178
<211> LENGTH: 381
<212> TYPE: DNA
<213> ORGANISM: Camelus bactrianus

<400> SEQUENCE: 178
caggtgcagc tgcaggagtc tgggggaggc tcggtgcaga ccggagggtc tctgagactc      60
tcctgtgcag cctctacatc aatatacagt aacaactaca tggcctggtt ccgccaggct     120
ccaggaaagg ggcgcgaggg ggtcgcagct gtttatattg atgatggtcg cccatactat     180
gccgactccg tgaagggccg attcaccatc tccctagaca gcgccaagaa cacggtgtat     240
```

```
ctgcaaatga acagcctgaa acctgaggac actgccatgt actactgtgc ggcagctcca    300 ggcccttaa gtcgtcatta ctggtacacg tccgccaact atgactactg gggcccgggg    360
acccaggtca ccgtctcctc a                                              381
```

<210> SEQ ID NO 179
<211> LENGTH: 381
<212> TYPE: DNA
<213> ORGANISM: Camelus bactrianus

<400> SEQUENCE: 179

```
caggtgcagc tgcaggagtc tggaggaggc tcggtgcgga ccggagggtc tctgagactc     60
tcctgtgcag cctcgccatc aatatacagt aacaactaca tggcctggtt cagccaggct    120
ccaggaaagg ggcgcgaggg ggtcgcagct gtttatattg atgatggtcg cccatactat    180
gccgactccg tgaagggccg gttcaccatc tccctagaca gcgccaagaa cacggtgtat    240
ctgcaaatga acagcctgaa accggaggac actgccatgt actactgtgc ggcagctcca    300 ggcccttaa gtcgtaacta ctggtacacg tccgccaact atgactactg gggccagggg    360
acccaggtca ccgtctcctc a                                              381
```

<210> SEQ ID NO 180
<211> LENGTH: 381
<212> TYPE: DNA
<213> ORGANISM: Camelus bactrianus

<400> SEQUENCE: 180

```
caggtgcagc tgcaggagtc tggggggaggc tcggtgcaga ccggagggtc tctgagactc    60
tcctgtacag cctctacatc aatatacagt aacaactaca tggcctggtt cagccaggct    120
ccaggaaagg ggcgcgaggg ggtcgcagct gtttatattg acgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300 ggcccttaa gtcgtaatta ctggtacacg tccgccaact atgactactg gggccagggg    360
acccaggtca ccgtctcctc a                                              381
```

<210> SEQ ID NO 181
<211> LENGTH: 381
<212> TYPE: DNA
<213> ORGANISM: Camelus bactrianus

<400> SEQUENCE: 181

```
caggtgcagc tgcaggagtc tggaggaggc tcggtgcaga ccggagggtc tctgagactc     60
tcctgtgcag cctctacatc aatatacagt aacaactaca tggcctggtt ccgccaggct    120
ccaggaaagg ggcgcgaggg ggtcgccggt gtttatattg gtgatggtcg cccatactat    180
gccgactccg tgaagggccg attcaccatc tccctagaca gcgccaagaa cacggtgtat    240
ctgcaaatga acagcctgaa gcctgaggac actgccatgt actactgtgc ggcagctcca    300 ggcccttaa gtcatcatta ctggtacacg tccgccaact atgactactg gggcccgggg    360
acccaggtca ccgtctcctc a                                              381
```

<210> SEQ ID NO 182
<211> LENGTH: 381
<212> TYPE: DNA
<213> ORGANISM: Camelus bactrianus

<400> SEQUENCE: 182

| | |
|---|---|
| caggtgcagc tgcaggagtc tgggggaggc tcggtgcaga ccggagggtc tctgagactc | 60 |
| tcctgtgcag cctctacatc aatatacagt atcaactaca tggcctggtt cagccaggct | 120 |
| ccaggaaagg ggcgcgaggg ggtcgcagct gtttatattg gtgatggtcg cccatactat | 180 |
| gccgactccg tgaagggccg attcaccatc tccctagaca gcgccaagaa cacggtgtat | 240 |
| ctgcaaatga acagcctgaa acctgaggac actgccatgt actactgtgc ggcagcacca | 300 |
| ggccccttaa gtcagcatta ctggtacacg tccgccaact atgactactg gggccagggg | 360 |
| acccaggtca ccgtctcctc a | 381 |

<210> SEQ ID NO 183
<211> LENGTH: 381
<212> TYPE: DNA
<213> ORGANISM: Camelus bactrianus

<400> SEQUENCE: 183

| | |
|---|---|
| caggtgcagc tgcaggagtc tgggggaggc tcggtgcaga ccggagggtc tctgagactc | 60 |
| tcctgtgcat gctctacatc aatatacagt aacaactaca tggcctggtt cagccaggct | 120 |
| ccaggaaagg ggcgcgaggg ggtcgcagct gtttatattg gtgatggtcg cccatactat | 180 |
| gccgactccg tgaagggccg attcaccatc tccctagaca gcgccaagaa cacgatgtat | 240 |
| ctgcaaatga acagcctgaa acctgaggac actgccatgt actactgtgc ggcagcacca | 300 |
| ggccccttaa gtcagcatta ctggtacacg tccgccaact atgactactg gggccagggg | 360 |
| acccaggtca ccgtctcctc a | 381 |

<210> SEQ ID NO 184
<211> LENGTH: 381
<212> TYPE: DNA
<213> ORGANISM: Camelus bactrianus

<400> SEQUENCE: 184

| | |
|---|---|
| caggtgcagc tgcaggagtc tgggggaggc tcggtgcagg ctggagggtc tctgagactc | 60 |
| tcctgtgcag cctctggata cacccgcagt ctgtactgca tgggctggtt ccgccaggct | 120 |
| ccagggaggg agcgcgaggg ggtcgcacat gtttatactg gtgatggaag cccatactat | 180 |
| gccgactccg tgaagggccg attcaccatc tcccaagaca acggcgagag cacgctgtat | 240 |
| ctgcaaatga acaatctgaa acctgaggac actgccatgt actactgtgc ggcaggtaca | 300 |
| agtgccttat ctcgccccta cggtcccatc tcgtatggct actggtactg gggccagggg | 360 |
| acccaggtca ccgtctcctc a | 381 |

<210> SEQ ID NO 185
<211> LENGTH: 381
<212> TYPE: DNA
<213> ORGANISM: Camelus bactrianus

<400> SEQUENCE: 185

| | |
|---|---|
| caggtgcagc tgcaggagtc tgggggaggc tcggtgcaga ccggagggtc tctgagactc | 60 |
| tcctgtacag cctctacatc aatatacagt aacaactaca tggcctggtt cagccaggct | 120 |
| ccaggaaagg ggcgcgaggg ggtcgcagct gtttatattg acgatggtcg cccatactat | 180 |
| gccgactccg tgaagggccg attcaccatc tccctagaca gcgccaagaa cacggtgtat | 240 |
| ctgcaaatga acagcctgaa acctgaggac actgccatgt actactgtgc ggcagctcca | 300 |
| ggccccttaa gtcgtaatta ctggtacacg tccgccaact atgactactg gggccagggg | 360 |

```
                                    -continued
acccaggtca ccgtctcctc a                                              381

<210> SEQ ID NO 186
<211> LENGTH: 381
<212> TYPE: DNA
<213> ORGANISM: Camelus bactrianus

<400> SEQUENCE: 186
caggtgcagc tgcaggagtc tgggggaggc tcggtgcaga ccggagggtc tctgagactc    60
tcctgtgcag cctctacatc actatacagt tacaactaca tggcctggtt cagccaggct   120
ccaggaaagg ggcgcgaggg ggtcgcagct gtttatgttg gtgatggtcg cccatactat   180
gccgcctccg tgaagggccg attcaccatc tccctagaca gcgccaagaa cacggtgtat   240
ctgcaaatga acagcctgaa acctgaggac actgccatgt actactgtgc ggcagctcca   300
ggccccttaa gtcataatta ctggtacacg tccgccaact atgactactg gggccagggg   360
acccaggtca ccgtctcctc a                                              381

<210> SEQ ID NO 187
<211> LENGTH: 387
<212> TYPE: DNA
<213> ORGANISM: Camelus bactrianus

<400> SEQUENCE: 187
atggcccagg tgcagctgca ggagtctggg ggaggctcgg tgcagaccgg agggtctctg    60
agactctcct gtgcagcctc tacatcaata tacagtatca actacatggc ctggttcagg   120
caggctccag gaaaggggcg cgaggggtc gcagctgttt atattgatga tggtcgccca   180
tactatgccg actccgtgaa gggccgattc accatctccc tagacagcgc caagaacacg   240
gtgtatctgc aaatgaccag cctgaaatct gaggacactg ccatgtacta ctgtgcggca   300
gctccaggcc ccttaagtcg tagttactgg tacacgtccg ccaactatga ctactggggc   360
caggggaccc aggtcaccgt ctcctca                                        387

<210> SEQ ID NO 188
<211> LENGTH: 381
<212> TYPE: DNA
<213> ORGANISM: Camelus bactrianus

<400> SEQUENCE: 188
caggtgcagc tgcaggagtc tgggggaggc tcggtgcaga ccggagggtc tctgagactc    60
tcctgtgcag cctctacatc aatatacagt aacaactaca tggcctggtt cagccaggct   120
ccaggaaagg ggcgcgaggg ggtcgcagct gtttatattg gtgatggtcg cccatactat   180
gccgactccg cgaagggccg attcaccatc tccctagaca gcgccaagaa cacggtgtat   240
ctgcaaatga acagcctgaa acctgaggac actgccatgt actactgtgc ggcagctcca   300
ggccccttaa gtcgtaatta ctggtacacg tccgccaact atgactactg gggccagggg   360
acccaggtca ccgtctcctc a                                              381

<210> SEQ ID NO 189
<211> LENGTH: 381
<212> TYPE: DNA
<213> ORGANISM: Camelus bactrianus

<400> SEQUENCE: 189
caggtgcagc tgcaggagtc tgggggaggc tcggtgcaga ccggagggtc tctgagactc    60
tcctgtgcag cctctacatc aatatacagt aacaactaca tggcctggtt cagccaggct   120
```

```
ccaggaaagg ggcgcgaggg ggtcgcagcg ctttatattg gtgatggtcg cccatactat    180
gccgactccg tgaagggccg attcaccatc gccctagaca gcgccaagaa cacggtgtat    240
ctgcaaatga acggcctgaa acctgaggac actgccatgt actactgtgc ggcagctcca    300
ggccccttaa aacataatta ctggtacacg tccgccaact atgactactg gggccagggg    360
acccaggtca ccgtctcctc a                                              381

<210> SEQ ID NO 190
<211> LENGTH: 381
<212> TYPE: DNA
<213> ORGANISM: Camelus bactrianus

<400> SEQUENCE: 190
caggtgcagc tgcaggagtc tgggggaggc tcggtgcaga ccggagggtc tctgagactc     60
tcctgtgcag cctctacatc aatatacagt aacaactaca tggcctggtt cagccaggct    120
ccaggaaagg ggcgcgaggg ggtcgcgcgc ctttatattg gtgatggtcg cccatactat    180
gccgactccg tgaagggccg attcaccatc gccctagaca gcgccaagaa cacggtgtat    240
ctgcaaatga acggcctgaa acctgaggac actgccatgt actactgtgc ggcagctcca    300
ggccccttaa aacataatta ctggtacacg tccgccaact atgactactg gggccagggg    360
acccaggtca ccgtctcctc a                                              381

<210> SEQ ID NO 191
<211> LENGTH: 381
<212> TYPE: DNA
<213> ORGANISM: Camelus bactrianus

<400> SEQUENCE: 191
caggtgcagc tgcaggagtc tgggggaggc tcggtgcaga ccggagggtc tctgagactc     60
tcctgtgcag cctctacatc aatatacagt aacaactaca tggcctggtt ccgccaggct    120
ccaggaaagg ggcgcgaggg ggtcgcagct gtttatattg gtgatggtcg cccgtactat    180
gccgactccg cgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtcatta ctggtacacg tccgccaact atgattactg gggcccgggg    360
acccaggtca ccgtctcctc a                                              381

<210> SEQ ID NO 192
<211> LENGTH: 391
<212> TYPE: DNA
<213> ORGANISM: Camelus bactrianus

<400> SEQUENCE: 192
ggccatggcc caggtgcagc tgcaggagtc tggaggaggc tcggtgcaga ccggagggtc     60
tctgacgctc tcctgtgcag cctctacatc aatatacagt acaactaca tggcctggtt    120 ccgccaggct ccaggaaagg ggcgcgaggg ggtcgcagct gtttatattg gtgacggtcg    180
cccatactat gccgactccg tgaagggccg attcaccatc tccccggaca gcgccaagaa    240
cacggtgtat ctgcaaatga acagcctgaa acctgaggac actgccatgt actactgtgc    300
ggcagctcca ggccccttaa gtcgtcatta ctggtacacg tccgccaact atgactactg    360
gggcccgggg acccaggtca ccgtctcctc a                                   391

<210> SEQ ID NO 193
```

```
<211> LENGTH: 381
<212> TYPE: DNA
<213> ORGANISM: Camelus bactrianus

<400> SEQUENCE: 193
caggtgcagc tgcaggagtc tgggggaggc tcggtgcaga ccggagggtc tctgagactc        60
tcctgtgcag cctcttcatc aatagccagt aacaactaca tggcctggtt cagccaggct       120
ccaggaaagg ggcgcgaggg ggtcgcagct gtttatattg gtgatggtcg cccatactat       180
gccgactccg tgaagggccg attcaccatc tccctagaca gcgccaagaa cacggtgtat       240
ctgcaaatga acagcctgaa acctgaggac actgccatgt actactgtgc ggcagctcca       300
ggccccttaa gtcgtaatta ctggtacacg tccgccaact atgactactg gggccagggg       360
acccaggtca ccgtctcctc a                                                 381

<210> SEQ ID NO 194
<211> LENGTH: 381
<212> TYPE: DNA
<213> ORGANISM: Camelus bactrianus

<400> SEQUENCE: 194
caggtgcagc tgcaggagtc tgggggaggc tcggtgcgga ccggagggtc tctgagactc        60
tcctgtgcag cctctacatc aatatacagt ctcaactaca tggcctggtt cagccaggct       120
ccaggaaagg ggcgcgaggg ggtcgcagct gtttatattg atgatggtcg cccatactat       180
gccgatcacg tgaagggccg attcaccatc tccctagaca ccgccaagaa cacggtgtat       240
ttgcaaatga acagcctgaa acctgaggac actgccatgt actactgtgc ggcagctcca       300
ggccccttaa gtcgtaacta ctggtacacg tccgccaact atgactactg gggccagggg       360
acccaggtca ccgtctcctc a                                                 381

<210> SEQ ID NO 195
<211> LENGTH: 363
<212> TYPE: DNA
<213> ORGANISM: Camelus bactrianus

<400> SEQUENCE: 195
caggtgcagc tgcaggagtc tgggggaggc ttggtgcagc ctgggggtc tctgagactc         60 tcctgtgcag cctctggatt caccttcagt attaaagcca tgagctgggt ccgccaggct       120
ccagggaagg gactcgagtg ggtctcaact attgatagtg gtggtgggcg ccgatactat       180
gcagactccg tgaagggccg attcaccatc tccagagaca cgccaagaa cacgctgtat       240 ctgcaattga gcagcctgaa aactgaggac acggccatgt atttttgtgc aagatgtagt      300
gatatttact gctacaacgg agcgtcgtat aggggccagg gacccaggt caccgtctcc       360 tca                                                                     363

<210> SEQ ID NO 196
<211> LENGTH: 381
<212> TYPE: DNA
<213> ORGANISM: Camelus bactrianus

<400> SEQUENCE: 196
caggtgcagc tgcaggagtc tgggggaggc tcggtgcaga ccggagggtc tctgagactc        60
tcctgtgcag cctctacatc aatcgacagt aacaactaca tggcctggtt ccgccaggct       120
ccaggaaagg ggcgcgaggg ggtcgcagct gtttatattg atgatggtcg cccatactat       180
gccgactccg tgaagggccg attcaccatc tccctagaca gcgccaagaa cacggtgtat       240
```
ctgcaaatga acagcctgaa acctgaggac actgccatgt actactgtgc ggcagctcca    300 ggcccctta a gtcgtcatta ctggtacacg tccgccaact atgactactg gggcccgggg    360
acccaggtca ccgtctcctc a    381

<210> SEQ ID NO 197
<211> LENGTH: 381
<212> TYPE: DNA
<213> ORGANISM: Camelus bactrianus

<400> SEQUENCE: 197
caggtgcagc tgcaggagtc tggaggaggc tcggtgcaga ccggagggtc tctgagactc    60
tcctgtacag cctctacatc aatatacaat aacaactaca tggcctggtt cagccagtct    120
ccaggaaagg ggcgcgaggg ggtcgcagct gtttatatgg atgatggtcg cccatactat    180
gccgattccg tgaagggccg attcaccatc tccctagaca cgccaagaa cacgatgtat    240 ttgcaaatga acagcctgaa acctgaggac actgccatgt actactgtgc ggcagctcca    300 ggcccctta a gtcgtaacta ctggtacacg tccgccaact atgactactg gggccagggg    360
acccaggtca ccgtctcctc a    381

<210> SEQ ID NO 198
<211> LENGTH: 381
<212> TYPE: DNA
<213> ORGANISM: Camelus bactrianus

<400> SEQUENCE: 198
caggtgcagc tgcaggagtc tgggggaggc tcggtgcaga ccggagggtc tctgagactc    60
tcctgtgcag cctctacatc aatatacagt aacaactaca tggcctggtt cagccaggct    120
ccaggaaagg ggcgcgaagg ggtcgcagct gtttatattg atgatggtcg cacatactat    180
gccgactccg tgaagggccg attcaccatc tccctagaca cgccaagaa cacggtgtat    240 ctacaaatga acagcctgaa acctgaggac actgccatgt actactgtgc ggcagctcca    300 ggcccctta a gtcataatta ctggtacgcg tccgccaact atgactactg gggccagggg    360
acccaggtca ccgtctcctc a    381

<210> SEQ ID NO 199
<211> LENGTH: 381
<212> TYPE: DNA
<213> ORGANISM: Camelus bactrianus

<400> SEQUENCE: 199
caggtgcagc tgcaggagtc tgggggaggc tcggtgcaga ccggagggtc tctgagactc    60
tcctgtgcag cctctacatc aatatacagt atcaactaca tggcctggtt cagccaggct    120
ccaggaaagg ggcgcgaggg ggtcgcagct gtttatattg atgatggtcg cccatactat    180
gccgactccg tgaagggccg attcaccatc tccctagaca cgccaagaa cacggtgtat    240 ctgcaaatga acagcctgaa acctgaggac actgccatgt actactgtgc ggcagctcca    300 ggcccctta a gtcgtaatta ctggtacacg tccgccaact atgactactg gggccagggg    360
acccaggtca ccgtctcctc a    381

<210> SEQ ID NO 200
<211> LENGTH: 363
<212> TYPE: DNA
<213> ORGANISM: Camelus bactrianus

<400> SEQUENCE: 200

```
caggtgcagc tgcaggagtc tgggggaggc ttggtgcagc ctgggggtc tctgagactc      60
tcctgtatag cctctggatt caccttcagt atcatggcca tgagctgggt ccgccaggct    120
ccagggaagg gactcgagtg gtctcaact attaatagtg atggtggcaa aacatactat    180
gcagactccg tgaagggccg cttcaccatc tccagagaca acgccaagaa cacgctgtat    240
ctgcaattga atagcctgag aactgaggat atggccatgt attactgccg acggtgcgcg    300
gatatttact gttcaggttc cggcggatgg acgggccagg gacccaggt caccgtctcc    360
tca                                                                  363
```

<210> SEQ ID NO 201
<211> LENGTH: 381
<212> TYPE: DNA
<213> ORGANISM: Camelus bactrianus

<400> SEQUENCE: 201

```
caggtgcagc tgcaggagtc tgggggaggc tcggtgcaga ccggagggtc tctgagactc      60
tcctgtacag cctctacatc aatatacagt aacagctaca tggcctggtt cagccaggct    120
ccaggaaagg ggcgcgaggg ggtcgcagct gtttatattg atgatggtcg cccatactat    180
gccgactccg tgaagggccg tttcaccatc tccctagaca cgccaagaa cacggtgtat    240
ctgcaaatga acagcctgaa acctgaggac actgccatgt actactgtgc ggcagctcca    300
ggccccttaa gtcgtcatta ctggtacacg tccgccaact atgactactg gggccagggg    360
acccaggtca ccgtctcctc a                                              381
```

<210> SEQ ID NO 202
<211> LENGTH: 381
<212> TYPE: DNA
<213> ORGANISM: Camelus bactrianus

<400> SEQUENCE: 202

```
caggtgcagc tgcaggagtc tggaggaggc tcggtgcaga ctggagggtc tctgagactc      60
tcctgtgcag cctctacatc aatatacagt aacaactaca tggcctggtt ccgccaggct    120
ccaggaaagg ggcgcgaggg ggtcgcagct gtttatgttg atgatggtcg cccatactat    180
gccgactccg tgaagggccg attcaccatc tcccgcgaca cgccaagaa cacggtgtat    240
ctgcaaatga acagcctgaa acctgaggac actgccatgt actactgtgc ggcagctcca    300
ggccccttaa gtcgtcatta ctggtacacg tccgccaact atgactactg gggcccgggg    360
acccaggtca ccgtctcctc a                                              381
```

<210> SEQ ID NO 203
<211> LENGTH: 381
<212> TYPE: DNA
<213> ORGANISM: Camelus bactrianus

<400> SEQUENCE: 203

```
caggtgcagc tgcaggagtc tgggggaggc tcggtgcaga ccggagggtc tctgagactc      60
tcctgtgcag cctctacatc aatatacagt aacaactaca tggcctggtt cagccaggct    120
ccaggaaagg ggcgcgaggg ggtcgcagct gtttatattg atgatggtcg cccatactat    180
gccgactccg tgaagggccg attcaccatc tccctagaca cgccaagaa cacggtgtat    240
ctgcaaatga acagcctgaa acctgaggac actgccatgt actactgtgc ggcagctcca    300
ggccccttaa gtcgtaatta ctggtacacg tccgccaact atgactactg gggccagggg    360
```

```
acccaggtca ccgtctcctc a                                            381

<210> SEQ ID NO 204
<211> LENGTH: 381
<212> TYPE: DNA
<213> ORGANISM: Camelus bactrianus

<400> SEQUENCE: 204
caggtgcagc tgcaggagtc tgggggaggc tcggtgcaga ccggagggtc tctgagactc    60
tcctgtgcac cctctacatc aatatacgat aacaactaca tggcctggtt cagccaggct   120
ccaggaaagg ggcgcgaggg ggtcgcagcg atttatattg atgatggtcg cccatactat   180
gccgactccg tgaagggccg attcaccatc tccctagaca cgccaagaa cacggtgtat    240 ctgcaaatga acagcctgaa acctgaggac actgccatgt actactgtgc ggcagctcca   300
ggccccttaa gtcataatta ctggtacacg tccgccaact atgactactg gggccagggg   360
acccaggtca ccgtctcctc a                                            381

<210> SEQ ID NO 205
<211> LENGTH: 381
<212> TYPE: DNA
<213> ORGANISM: Camelus bactrianus

<400> SEQUENCE: 205
caggtgcagc tgcaggagtc tgaggaggc tcggtgcaga ccggagggtc tctgagactc     60
tcctgtgtag cctctacatc gatattcagt aacaactaca tggcctggtt cagccaggct   120
ccaggaaagg ggcgcgaggg ggtcgcagct gtttatattg gtgatggtcg cccatactat   180
gccgactccg tgaagggccg attcaccatc tccctagaca cgccaagaa cacggtgtat    240 ctgcaaatga acagcctgaa acctgaggac actgccatgt actactgtgc ggcagctcca   300
ggccccttaa gtcacaatta ttggtacacg tccgccaact atgactactg gggccagggg   360
acccaggtca ccgtctcctc a                                            381

<210> SEQ ID NO 206
<211> LENGTH: 381
<212> TYPE: DNA
<213> ORGANISM: Camelus bactrianus

<400> SEQUENCE: 206
caggtgcagc tgcaggagtc tgggggaggc tcggtgcaga ccggagggtc tctgagactc    60
tcctgtgcag cctctccatc aatatacagt gccaactaca tggcctggtt cagccaggct   120
ccaggaaagg ggcgcgaggg ggtcgcagct gtttatattg gtgatggtcg cccatactat   180
gccgactccg tgaagggccg attcaccatc tccctagaca cgccaagag cacggtgtat    240 ctgcaaatga acagcctgaa acctgaggac actgccatgt actactgtgc ggcagctcca   300
ggccccttaa gtcataatta ctggtacacg tccgccaact atgactactg gggccagggg   360
acccaggtca ccgtctcctc a                                            381

<210> SEQ ID NO 207
<211> LENGTH: 381
<212> TYPE: DNA
<213> ORGANISM: Camelus bactrianus

<400> SEQUENCE: 207
caggtgcagc tgcaggagtc tgaggaggc tcggtgcaga ccggagggtc tctgagactc     60
```

```
tcctgtgcag cctctacatc aatatacagt atcaactaca tggcctggtt cagccaggct    120
ccaggaaagg ggcgcgaggg ggtcgcagct gtttatattg atgatggtcg cccatactat    180
gccgactccg tgaagggccg attcaccatc tccctagaca gcgccaagaa cacggtgtat    240
ctgcaaatga acagcctgaa atctgaggac actgccatgt actactgtgc ggcagctcca    300 ggcccccttaa gtcgtaatta ctggtacacg tccgccaact atgactactg gggccagggg    360
acccaggtca ccgtctcctc a                                              381
```

<210> SEQ ID NO 208
<211> LENGTH: 363
<212> TYPE: DNA
<213> ORGANISM: Camelus bactrianus

<400> SEQUENCE: 208

```
caggtgcagc tgcaggagtc tggaggaggc ttggtgcagc ctggggggtc tctgagactc     60
tcctgtgcac tatctggatt caccctctact atatatgcca tgagctgggt ccgccaggct   120
ccagggaagg gactcgagtg ggtctcaact attaatagtg atggtggcta ccgatactat    180
gcagactccg tgaagggccg attcaccatc tccagagaca tgccaagaa cacgctgtat     240 ctgcaattga acagcccgaa aactgaggac acggccatgt attactgtgc aagatgtagt    300
gatatttact gttacaacgg accgtcgtat aggggccagg ggacccaggt caccgtctcc    360
tca                                                                  363
```

<210> SEQ ID NO 209
<211> LENGTH: 381
<212> TYPE: DNA
<213> ORGANISM: Camelus bactrianus

<400> SEQUENCE: 209

```
caggtgcagc tgcaggagtc tgggggaggc tcggtgcaga ccggagggtc tctgagactc     60
tcctgtgcat gctctacatc aatatacagt aacaactaca tggcctggtt cagccaggct   120
ccaggaaagg ggcgcgaggg ggtcgcagct gtttatattg gtgatggtcg cccttactat    180
accgactccg tgaagggccg attcaccatc tccctagaca gcgccaagaa cacactgtat    240
ctgcaaatga acagcctgaa acctgaggac actgccatgt actactgtgc ggcagctcca    300 ggcccccttaa gtcataatta ctggtacacg tccgccaact atgactactg gggccagggg    360
acccaggtca ccgtctcctc a                                              381
```

<210> SEQ ID NO 210
<211> LENGTH: 381
<212> TYPE: DNA
<213> ORGANISM: Camelus bactrianus

<400> SEQUENCE: 210

```
caggtgcagc tgcaggagtc tgggggaggc tcggtgcaga ccggagggtc tctgagactc     60
tcctgtgcag cctctacatc aatatacagt atgaactaca tggcctggtt cagccaggct   120
ccaggaaagg ggcgcgaggg ggtcgcagct gtttatattg aagatggtcg cccatactat    180
gccgactccg tgaagggccg attcaccatc tccccagaca gggccaagaa cacggtgtat    240
ctgcaaatga acagcctgaa acctgaggac actgccatgt actactgtgc ggcagctcca    300 ggcccccttaa gtcgtaatta ctggtacacg tccgccaact atgactactg gggccagggg    360
acccaggtca ccgtctcctc a                                              381
```

<210> SEQ ID NO 211
<211> LENGTH: 363
<212> TYPE: DNA
<213> ORGANISM: Camelus bactrianus

<400> SEQUENCE: 211

```
caggtgcagc tgcaggagtc tgaggaggc ttggtgcagc ctgggggtc tctgagactc      60 tcctgtgcag cctctggatt cgacttcagt agcagagcca tgagctgggt ccgccaggct    120
ccagggaagg gactcgagtg gtctcaact attaatagtg gtggtggtag ccgatactat     180
gcagactccg tgaagggccg attcaccacc tccagagaca cgccaagaa cacgctggct     240 ctgcaattga acagcctgaa aactgaggac acggccatgt attactgtgc aagatgtagt    300
gatatttact gcgacaacgg agcgtggtat aggggccagg ggacccaggt caccgtctcc    360
tca                                                                  363
```

<210> SEQ ID NO 212
<211> LENGTH: 381
<212> TYPE: DNA
<213> ORGANISM: Camelus bactrianus

<400> SEQUENCE: 212

```
caggtgcagc tgcaggagtc tgaggaggc tcggtgcagg ctgggggtc tctgagactc      60 tcctgtgcag cctctacatc aatatacagt aacaactaca tggcctggtt ccgccagact    120
ccaggaaagg ggcgcgaggg ggtcgcagct gtttatattg atgatgggcg accatactat    180
gccgactccg tgaagggccg attcaccatc tccctagaca cgccaagaa cacggtgtat     240 ttgcaaatga acagcctgaa acctgaggac actgccatgt actactgtgc ggcagctcca   300
ggccccttaa gtcatgatta ctggtacacg tccgccaact atgactactg ggcccgggg    360 acccaggtca ccgtctcctc a                                              381
```

<210> SEQ ID NO 213
<211> LENGTH: 381
<212> TYPE: DNA
<213> ORGANISM: Camelus bactrianus

<400> SEQUENCE: 213

```
caggtgcagc tgcaggagtc tgggggaggc tcggtgcaga ccggagggtc tctgagactc    60
tcctgtgcag cctctacatc aatatacagt aacaactaca tggcctggtt cagccaggct   120
ccaggaaagg ggcgcgaggg ggtcgcagct gtttatattg atgatggtcg cccatactat    180
gccgactccg tgaagggccg attcaccatc tccctagaca cgccaagaa cacggtgtat    240 ctgcaaatga accgcctgaa acctgaggac actgccatgt actactgtgc ggcagctcca   300
ggccccttaa gtcataatta ctggtacacg tccgccaact atgactactg ggccagggg    360 acccaggtca ccgtctcctc a                                              381
```

<210> SEQ ID NO 214
<211> LENGTH: 381
<212> TYPE: DNA
<213> ORGANISM: Camelus bactrianus

<400> SEQUENCE: 214

```
caggtgcagc tgcaggagtc tgggggaggc tcggtgcaga ccggagggtc tctgagactc    60
tcctgtgcag cctctacatc aatatacagt aacaactaca tggcctggtt cagccaggct   120
ccaggaaagg ggcgcgaggg ggtcgcagct gtttatattg atgatggtcg cccatactat   180
```

```
gccgactccg tgaagggccg attcaccatc tccctagaca gcgccaagaa cacggtgtat    240
ctgcaaatga acagcctgaa acctgaggac actgccatgt actactgtgc ggcaacacca    300
ggccccttaa gtcagcatta ctggtacacg tccgccaact atgactactg gggccagggg    360
acccaggtca ccgtctcctc a                                              381

<210> SEQ ID NO 215
<211> LENGTH: 363
<212> TYPE: DNA
<213> ORGANISM: Camelus bactrianus

<400> SEQUENCE: 215
caggtgcagc tgcaggagtc tgggggaggc ttggtgcagc tggggggtc tctgagactc     60 tcctgtgcag cctctggatt caccttcagt atccttgcca tgagctgggt ccgccaggct    120
ccagggaagg gactcgaatg gatctcaact attaataata gtggtggcac acattctat    180 gctgactccg tgaagggccg cttcaccatc tccagagaca cgccaagaa cacgctgtat    240 ctgcaattga atagcctgag aactgaggac acggccatgt attactgccg acggtgcacg    300
gatatttact gttcactttc cggcggatgg acgggccagg gacccaggt caccgtctcc    360 tca                                                                  363

<210> SEQ ID NO 216
<211> LENGTH: 381
<212> TYPE: DNA
<213> ORGANISM: Camelus bactrianus

<400> SEQUENCE: 216
caggtgcagc tgcaggagtc tggaggaggc tcggtgcaga ccggagggtc tctgagactc     60
tcctgtgcag cctctacatc aatatacaat aacaactaca tggcctggtt cagccaggct    120
ccaggaaagg ggcgcgaggg ggtcgcggct gtttatgttg gtgatggtcg cacatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcataatta ctggtacacg tccgccaact atgactactg gggccagggg    360
acccaggtca ccgtctcctc a                                              381

<210> SEQ ID NO 217
<211> LENGTH: 381
<212> TYPE: DNA
<213> ORGANISM: Camelus bactrianus

<400> SEQUENCE: 217
caggtgcagc tgcaggagtc tgggggaggc tcggtgcaga ccggagggtc tctgagactc     60
tcctgtacag cctctacatc aatatacagt aacaactaca tggcctggtt cagccaggct    120
ccaggaaagg ggcgcgaggg ggtcgcagct gtttatattg acgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtaatta ctggtacacg tccgccaact atgactactg gggccagggg    360
acccaggtca ccgtctcctc a                                              381

<210> SEQ ID NO 218
<211> LENGTH: 381
<212> TYPE: DNA
<213> ORGANISM: Camelus bactrianus
```

<400> SEQUENCE: 218

```
caggtgcagc tgcaggagtc tggaggaggc tcggtgcaga ccggagggtc tctgagactc    60
tcctgtacat gctctacatc aatatacagt aacaactaca tggcctggtt cagccaggct   120
ccaggaaagg ggcgcgaggg ggtcgcagct gtttatattg gtgatggtcg cccatactat   180
gccgactccg tgaagggccg attcaccatc tccctagaca gcgccaagaa cacggtgtat   240
ctgcaaatga acagcctgaa acctgaggac actgccatgt actactgtgc ggcagctcca   300
ggccccttaa gtcataatta ctggtacacg tccgccaact atgactactg gggccagggg   360
acccaggtca ccgtctcctc a                                             381
```

<210> SEQ ID NO 219
<211> LENGTH: 381
<212> TYPE: DNA
<213> ORGANISM: Camelus bactrianus

<400> SEQUENCE: 219

```
caggtgcagc tgcaggagtc tggaggaggc tcggtgcaga ccggagggtc tctgagactc    60
tcctgtgcag cctctacatc aatatacagt aacaactaca tggcctggtt cagccaggct   120
ccaggaaagg ggcgcgaggg ggtcgcagct gtttatattg gtgatggtcg cccatactat   180
gccgactccg tgaagggccg attcaccatc tccctagaca gcgccaagaa cacggtgtat   240
ctgcaaatga acagcctgaa acctgaggac actgccatgt actactgtgc ggcagctcca   300
ggccccttaa gtcataatta ctggtacacg tccgccaact atgactactg gggccagggg   360
acccaggtca ccgtctcctc a                                             381
```

<210> SEQ ID NO 220
<211> LENGTH: 363
<212> TYPE: DNA
<213> ORGANISM: Camelus bactrianus

<400> SEQUENCE: 220

```
caggtgcagc tgcaggagtc tggaggaggc ttggtgcagc ctgggggtc tctgagactc     60
tcctgtgcag cctctggatt caccttcagt attcgtgcca tgagctgggt ccgccaggct   120
ccagggaagg gactcgagtg ggtctcaact attaatagtg gtggtgatag ccgatactat   180
gcagactccg tgaagggccg attcaccatc tccagagaca cgccaagaa cacaatgtat   240
ctgcaattga acagcctgaa aactgaggac acggccatgt attactgtgt aagatgtagt   300
gatatttact gctacaacgg agcgtcgtat aggggccagg ggacccaggt caccgtctcc   360
tca                                                                 363
```

<210> SEQ ID NO 221
<211> LENGTH: 366
<212> TYPE: DNA
<213> ORGANISM: Camelus bactrianus

<400> SEQUENCE: 221

```
caggtgcagc tgcaggagtc tggaggaggc ttggtgcagc ctgggggtc tctgagactc     60
tcctgtgcag cctctggatt cacattcagt agctacgaca tgagctgggt ccgccaggct   120
ccagggaagg ggatcgagtg ggtctcagtt attaatagtg gtggtagtaa cacagactat   180
gcagactccg tgaagggccg attcaccatc tccagagaca cgccaagaa cacgctgtat   240
ctgcaaatga acagcctgaa aactgaggac actgccgtgt attactgcgc cacagcctgg   300
```

```
atgggctata gcgactatct cgatggaatc gcccggggcc aggggaccca ggtcaccgtc    360
tcctca                                                               366

<210> SEQ ID NO 222
<211> LENGTH: 363
<212> TYPE: DNA
<213> ORGANISM: Camelus bactrianus

<400> SEQUENCE: 222
caggtgcagc tgcaggagtc tgggggaggc ttggtgcagc ctggggggtc tctgagactc    60
tcctgtgaag cctctggact ccccttcagc atcattgcca tgagctgggt ccgccaggct   120
ccagggaagg gactcgagtg gtctcaact  attaatagtg atggtggcac cacacactat   180
gcagactccg tgaagggccg cttcaccatc tccagagaca cgccaagaa  cacgctgtat   240 ctgcaattga atagcctgag gactgaggac acggccatgt attactgccg acggtgcacg   300
gatatttact gttcaggttc cggcggatgg acgggccagg ggacccaggt caccgtctcc   360
tca                                                                  363

<210> SEQ ID NO 223
<211> LENGTH: 363
<212> TYPE: DNA
<213> ORGANISM: Camelus bactrianus

<400> SEQUENCE: 223
caggtgcagc tgcaggagtc tggaggaggc ttggtgcagc ctggggggtc tctgagactc    60
tcctgtgaag cctctggact ccccttcagc atcattgcca tgagctgggt ccgccaggct   120
ccagggaagg gactcgagtg gtctcaact  attaatagtg atggtggcac cacacactat   180
gcagactccg tgaagggccg cttcaccatc tccagagaca cgccaagaa  cacgctgtat   240 ctgcaattga atagcctgag gactgaggac acggccatgt attactgccg acggtgcacg   300
gatatttact gttcaggttt cggcggatgg acgggccagg ggacccaggt caccgtctcc   360
tca                                                                  363

<210> SEQ ID NO 224
<211> LENGTH: 363
<212> TYPE: DNA
<213> ORGANISM: Camelus bactrianus

<400> SEQUENCE: 224
caggtgcagc tgcaggagtc tgggggaggc tcggtgcagg ctggagggtc tctgagactc    60
tcctgtgcag cctctggatt caccggcagt atttatgcca tgagctgggt ccgccaggct   120
ccagggaagg gactcgagtg gtctcaact  attagtagta gtggtggtag gcgattctat   180
gcagactccg tgaagggccg attcaccatc tccagagaca cgccaagaa  cacgctgtat   240 ctgcaattga acagccttaa aactgaggac acggccatgt attactgtgc aagatgtagt   300
gatatttact gcgacaacgg agcgtcgtat aggggccagg ggacccaggt caccgtctcc   360
tca                                                                  363

<210> SEQ ID NO 225
<211> LENGTH: 381
<212> TYPE: DNA
<213> ORGANISM: Camelus bactrianus

<400> SEQUENCE: 225
caggtgcagc tgcaggagtc tgggggaggc tcggtgcaga ccggagggtc tctgagactc    60
```

```
tcctgtgcag cctctacatc aatatacagt aacaactaca tggcctggtt ccgccaggct    120
ccaggaaagg ggcgcgaggg ggtcgcagct gtttatattg gtgatggtcg cccatactat    180
gccgactccg cgaagggccg attcaccatc tccctagaca gcgccaagaa cacggtgtat    240
ctgcacatga acagcctgaa acctgaggac actgccatgt actactgtgc ggcagctcca    300
ggccccttaa gtcgtcatta ctggtacacg tccgccaact atgactactg ggggcccgggg    360 acccaggtca ccgtctcctc a                                              381

<210> SEQ ID NO 226
<211> LENGTH: 381
<212> TYPE: DNA
<213> ORGANISM: Camelus bactrianus

<400> SEQUENCE: 226
caggtgcagc tgcaggagtc tgggggaggc tcggtgcaga ccggagggtc tctgagactc     60
tcctgtgcag cctctacatc aatatacagt aacaactaca tggcctggtt ccgccaggtt    120
ccaggaaagg ggcgcgaggg ggtcgcagct gtttatattg atgatggtcg cacatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtcatta ctggtacacg tccgccaact atgactactg gggcccgggg    360
acccaggtca ccgtctcctc a                                              381

<210> SEQ ID NO 227
<211> LENGTH: 381
<212> TYPE: DNA
<213> ORGANISM: Camelus bactrianus

<400> SEQUENCE: 227
caggtgcagc tgcaggagtc tgggggaggc tcggtgcaga ccggagggtc tctgagactc     60
tcctgtacag cctctacatc aatatacagt aacaactaca tggcctggtt cagccaggct    120
ccaggaaagg ggcgcgaggg ggtcgcagct gtttatattg atgatggtcg ccctactat    180 gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtaatta ctggtacacg tccgccaact atgactactg gggccagggg    360
acccaggtca ccgtctcctc a                                              381

<210> SEQ ID NO 228
<211> LENGTH: 381
<212> TYPE: DNA
<213> ORGANISM: Camelus bactrianus

<400> SEQUENCE: 228
caggtgcagc tgcaggagtc tgggggaggc tcggtgcaga ccggagggtc tctgagactc     60
tcctgtgcag cctctacatc actatacagt tacaactaca tggcctggtt cagccaggct    120
ccaggaaagg ggcgcgaggg ggtcgcagct gtttatgttg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcataatta ctggtacacg tccgccaact atgactactg gggccagggg    360
acccaggtca ccgtctcctc a                                              381
```

<210> SEQ ID NO 229
<211> LENGTH: 363
<212> TYPE: DNA
<213> ORGANISM: Camelus bactrianus

<400> SEQUENCE: 229

```
caggtgcagc tgcaggagtc tgggggaggc ttggtgcagc ctggggggtc tctgagactc      60
tcctgtgcag cctctggatt gcccttcagt atcattgcca tgagctgggt ccgccaggct     120
ccagggaagg gaatcgagtg ggtctcaact attaatagtg gtggtggcac cacacactat     180
gcagactccg tgaagggccg cttcaccatc tccagagaca acgccaagaa cacgctgtat     240
ctgcaattga atagcctgag aactgaggac acggccgtgt attactgccg acggtgcgcg     300
gatatttact gttcaggttc cggcggatgg acgggcctgg gacccaggt caccgtctcc     360
tca                                                                   363
```

<210> SEQ ID NO 230
<211> LENGTH: 381
<212> TYPE: DNA
<213> ORGANISM: Camelus bactrianus

<400> SEQUENCE: 230

```
caggtgcagc tgcaggagtc tggaggaggc tcggtgcaga ccggagggtc tctgagactc      60
tcctgtgtag cctctacatc aatatacagt aacaactaca tggcctggtt cagccaggct     120
ccaggaaagg ggcgcgaggg ggtcgcagct gtttatattg atgatggtcg cccatactat     180
gccgactccg tgaagggccg attcaccatc tccctagaca cgccaagaa cacggtgtat     240
ctgcaaatga acagcctgaa acctgaggac actgccatgt actactgtgc ggcagctcca     300
ggccccttaa gtcgtagtta ctggtacacg tccgccaact atgactactg gggccagggg     360
acccaggtca ccgtctcctc a                                               381
```

<210> SEQ ID NO 231
<211> LENGTH: 381
<212> TYPE: DNA
<213> ORGANISM: Camelus bactrianus

<400> SEQUENCE: 231

```
caggtgcagc tgcaggagtc tggaggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttatattg atgatggtcg cacatactat     180
gccgactccg tgaagggccg attcaccatc tccctagaca cgccaagaa cacggtgtat     240
ctgcaaatga acagcctgaa acctgaggac actgccatgt actactgtgc ggcagctcca     300
ggccccttaa gtcgtaatta ctggtacacg tccgccaact atgactactg gggccagggg     360
acccaggtca ccgtctcctc a                                               381
```

<210> SEQ ID NO 232
<211> LENGTH: 381
<212> TYPE: DNA
<213> ORGANISM: Camelus bactrianus

<400> SEQUENCE: 232

```
caggtgcagc tgcaggagtc tgggggaggc tcggtgcaga ccggagggtc tctgagactc      60
tcctgtacag cctctacatc aatatacagt aacaactaca tggcctggtt cagccaggct     120
ccaggaaagg ggcgcgaggg ggtcgcagct gtttatattg acgatggtcg cccatactat     180
```

-continued

```
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtaatta ctggtacacg tccgccaact atgactactg gggccagggg    360
acccaggtca ccgtctcctc a                                              381
```

<210> SEQ ID NO 233
<211> LENGTH: 381
<212> TYPE: DNA
<213> ORGANISM: Camelus bactrianus

<400> SEQUENCE: 233

```
caggtgcagc tgcaggagtc tgggggaggc ttggtgcaga ccggagggtc tctgagactc     60
tcctgtgcag cctctacatc aatatacagt aacaactacc tggcctggtt cagccaggct    120
ccaggaaagg ggcgcgaggg ggtcgcagct gtttatattg gtgatggtcg cccatactat    180
gccgactccg tgaagggccg attccccatc tccctaaaca gcgccagaa caaggtgtat     240 ctgcaaatga acagcctgaa acctgaggac actgccatgt actactgtgc ggcagctcca    300
ggccccttaa gtcgtaatta ctggtacacg tccgccaact atgactactg gggccagggg    360
acccaggtca ccgtctcctc a                                              381
```

<210> SEQ ID NO 234
<211> LENGTH: 381
<212> TYPE: DNA
<213> ORGANISM: Camelus bactrianus

<400> SEQUENCE: 234

```
caggtgcagc tgcaggagtc tggaggaggc tcggtgcaga ccggagggtc tctgagactc     60
tcctgtgcag cctctacatc aatcgacagt aacaactaca tggcctggtt ccgccaggct    120
ccaggaaagg ggcgcgaggg ggtcgcagct gtttatattg atgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtcatta ctggtacacg tccgccaact atgactactg gggcccgggg    360
acccaggtca ccgtctcctc a                                              381
```

<210> SEQ ID NO 235
<211> LENGTH: 381
<212> TYPE: DNA
<213> ORGANISM: Camelus bactrianus

<400> SEQUENCE: 235

```
caggtgcagc tgcaggagtc tggaggaggc tcggtgcaga ccggagggtc tctgagactc     60
tcctgtgcag cctctacatc aatatacagt aacaactaca tggcctggtt cagccaggct    120
ccaggaaagg ggcgcgaggg ggtcgcagct gtttatattg ctgatgaccg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtaatta ctggtacacg tccgccaact atgactactg gggccagggg    360
acccaggtca ccgtctcctc a                                              381
```

<210> SEQ ID NO 236
<211> LENGTH: 381
<212> TYPE: DNA

<213> ORGANISM: Camelus bactrianus

<400> SEQUENCE: 236

| caggtgcagc tgcaggattc tggggaggc tcggtgcaga ccggagggtc tctgcgactc | 60 |
| tcctgtgcag cctctacatc aatatacagt atcaactaca tggcctggtt cagccaggct | 120 |
| ccaggaaagg ggcgcgaggg ggtcgcagct gtttatactg gtgatggtcg cccatactat | 180 |
| gccgactccg tgaagggccg attcaccatc tccctagaca cgccaagaa cacggtgtat | 240 |
| ctgcaaatga acagcctgaa acctgaggac actgccatgt actactgtgc ggcagctcca | 300 |
| ggccccttaa gtcgtaatta ctggtacacg tccgccaact atgactactg gggccagggg | 360 |
| acccaggtca ccgtctcctc a | 381 |

<210> SEQ ID NO 237
<211> LENGTH: 381
<212> TYPE: DNA
<213> ORGANISM: Camelus bactrianus

<400> SEQUENCE: 237

| caggtgcagc tgcaggagtc tggaggaggc tcggtgcagg ctggagggtc tctgagactc | 60 |
| tcctgtgcag cctctggata cacccgcagt agctactgca tgggctggtt ccgccaggct | 120 |
| ccagggaagg agcgcgagag ggtcgcatat atttattctg gtagtggaag cacacactat | 180 |
| gccgactccg tgaagggccg attcaccatc tcccaagaca cggcaagaa cacgctatat | 240 |
| ctgcaaatga acaatctgaa acctgaggac actgccatgt actactgtgc ggcagggaca | 300 |
| agtggtactt cgtgccccac cggtgcgttc atgtatgagt actggtactg gggccagggg | 360 |
| acccaggtca ccgtctcctc a | 381 |

<210> SEQ ID NO 238
<211> LENGTH: 381
<212> TYPE: DNA
<213> ORGANISM: Camelus bactrianus

<400> SEQUENCE: 238

| caggtgcagc tgcaggagtc tggggaggc tcggtgcagg ctggagggtc tctgagactc | 60 |
| tcctgtgcag cctctacatc aatatacagt aacaactaca tggcctggtt ccgccaggct | 120 |
| ccaggaaagg ggcgcgaggg ggtcgcagct gtttatgttg gtgatggtcg cccatactat | 180 |
| gccgactccg tgaagggccg attcaccatc tccctagaca cgccaagaa cacggtgtat | 240 |
| ctgcaaatga acagcctgaa acctgaggac actgccatgt actactgtgc ggcagctcca | 300 |
| ggccccttaa gtcataatta ctggtacacg tccgccaact atgactactg gggccagggg | 360 |
| acccaggtca ccgtctcctc a | 381 |

<210> SEQ ID NO 239
<211> LENGTH: 381
<212> TYPE: DNA
<213> ORGANISM: Camelus bactrianus

<400> SEQUENCE: 239

| caggtgcagc tgcaggagtc tggggaggc tcggtgcaga ccggagggtc tctgagactc | 60 |
| tcctgtgcag cctctacatc aatatacagt aacaactaca tggcctggtt cagccaggct | 120 |
| ccaggaaagg ggcgcgaggg ggtcgcagct gtttatattg gtgatggtcg cccatactat | 180 |
| gccgactccg tgaagggccg attcaccatc tccctagaca cgccaggaa cacggtgtat | 240 |
| ctgcaaatga acagcctgaa acctgaggac actgccatgt actactgtgc ggcagctcca | 300 |

-continued

```
gggcccttaa gtcgtcatta ctggtacacg tccgccaact atgactactg gggccagggg      360
acccaggtca ccgtctcctc a                                                381
```

<210> SEQ ID NO 240
<211> LENGTH: 381
<212> TYPE: DNA
<213> ORGANISM: Camelus bactrianus

<400> SEQUENCE: 240

```
caggtgcagc tgcaggagtc tggaggaggc tcggtgcagg ccggagggtc tctgagactc      60
tcctgtgcag cctctacatc aatatacagt aacaactaca tggcctggtt cagccaggct     120
ccaggaaagg ggcgcgaggg ggtcgcagct gtttatattg atgatggtcg cccctactat     180
gccgactccg tgaagggccg attcaccatc tccctagaca cgccaagaa cacggtgtat      240 ctgcaaatga acagcctgaa acctgaggac actgccatgt actactgtgc ggcagctcca     300
ggccccttaa gtcgtaatta ctggtacacg tccgccaact atgactactg gggccagggg    360
acccaggtca ccgtctcctc a                                                381
```

<210> SEQ ID NO 241
<211> LENGTH: 363
<212> TYPE: DNA
<213> ORGANISM: Camelus bactrianus

<400> SEQUENCE: 241

```
caggtgcagc tgcaggagtc tggaggagac ttggtgcagc ctgggggtc tctgagactc       60 tcctgtgcag cctctgggct cccttcagt atcattgcca tgagctgggt ccgccaggct     120
ccagggaagg gactcgagtg ggtctcaact attaataacg atggtggcac cacacactat    180
gcagactccg tgaagggccg cttcaccatc tccagagaca cgccaagaa cacgctatat     240 ctgcaattga atagcctgag aactgaggac acggccatgt attactgccg acggtgcacg    300
gatatttact gttcaggttc cggcggatgg acgggccagg gacccaggt caccgtctcc     360 tca                                                                    363
```

<210> SEQ ID NO 242
<211> LENGTH: 381
<212> TYPE: DNA
<213> ORGANISM: Camelus bactrianus

<400> SEQUENCE: 242

```
caggtgcagc tgcaggagtc tggaggaggc tcggtgcaga ccggagggtc tctgagactc      60
tcctgtgcag cctctacatc aatatacaat aacaactaca tggcctggtt ccgccaggct    120
ccaggaaagg ggcgcgaggg cgtcgcagct gtttatattg atgatggtcg cccatactat    180
gccgactccg tgaagggccg attcaccatc tccctagaca cgccaagaa cacggtgtat     240 ctgcaaatga acagcctgaa acctgaggac actgccatgt actactgtgc ggcagctcca    300
ggccccttaa gtcgtcatta ctggtacacg tccgccaact atgactactg gggcccgggg    360
acccaggtca ccgtctcctc a                                                381
```

<210> SEQ ID NO 243
<211> LENGTH: 381
<212> TYPE: DNA
<213> ORGANISM: Camelus bactrianus

<400> SEQUENCE: 243

```
caggtgcagc tgcaggagtc tggggggaggc tcggtgcaga ccggagggtc tctgagactc    60
tcctgtgcag cctctacatc aatatacagt aacaactaca tggcctggtt ccgccaggct   120
ccaggaaagg ggcgcgaggg ggtcgcagct gtttatattg gtgatggtcg cacatactat   180
gccgactccg cgaagggccg attcaccatc tccctagaca cgccaagaa cacggtgtat    240 ctgcatatga acagcctgaa acctgacgac actgccatgt actactgtgc ggcagctcca   300
ggccccttaa ctcgtcattt ctggtacacg tccgccaact atgactactg gggcccgggg   360
acccaggtca ccgtctcctc a                                             381
```

<210> SEQ ID NO 244
<211> LENGTH: 381
<212> TYPE: DNA
<213> ORGANISM: Camelus bactrianus

<400> SEQUENCE: 244

```
caggtgcagc tgcaggagtc tggggggaggc tcggtgcaga ccggagggtc tctgagactc    60
tcctgtgcag cctctacatc actatacagt tacaactaca tggcctggtt cagccaggct   120
ccaggaaagg ggcgcggggg ggtcgcagct gtttatgttg gtgatggtcg cccatactat   180
gccgactccg tgaagggccg attcaccatc tccctagaca cgccaagaa cacggtgtat    240 ctgcaaatga acagcctgaa acctgaggac actgccatgt actactgtgc ggcagctcca   300
ggccccttaa gtcataatta ctggtacacg tccgccaact atgactactg gggccagggg   360
acccaggtca ccgtctcctc a                                             381
```

<210> SEQ ID NO 245
<211> LENGTH: 381
<212> TYPE: DNA
<213> ORGANISM: Camelus bactrianus

<400> SEQUENCE: 245

```
caggtgcagc tgcaggagtc tggaggaggc tcggtgcagg ctggagggtc tctgagactc    60
tcctgtgcag cctctggata caccgtcagt aacaactaca tgggctggtt ccgccaggct   120
ccagggaagg ggcgcgaggg ggtcgcagct gtttatattg gtgatggtcg cccatactat   180
gccgactccg tgaagggccg attcaccatc tccctagaca cgccaagaa cacggtgtat    240 ctgcaaatga acagcctgaa acctgaggac actgccatgt actactgtgc ggcagctcca   300
ggccccttaa gtcagcatta ctggtacacg tccgccaact atgactactg gggccagggg   360
acccaggtca ccgtctcctc a                                             381
```

<210> SEQ ID NO 246
<211> LENGTH: 339
<212> TYPE: DNA
<213> ORGANISM: Camelus bactrianus

<400> SEQUENCE: 246

```
caggtgcagc tgcaggagtc tggggggaggc ttggtgcagc ctggggggtc tctgagactc    60
tcctgtgcag cctttggatt caccttcggt agctattgga tgaagtgggt ccgccaggct   120
ccagggaagg atctcgagtg ggtcccaatt attgataatg gtgggtcgtag cacatggtat   180 gcagactccg tgaagggccg attcaccatt tccagagaca atgccaagaa ctcgctgtat    240
ctgcaattga acagcctgaa aattgaggac acggccatgt attactgtgc ggaccggaac   300
gggaacaggg gccaggggac ccaggtcacc gtctcctca                            339
```

```
<210> SEQ ID NO 247
<211> LENGTH: 381
<212> TYPE: DNA
<213> ORGANISM: Camelus bactrianus

<400> SEQUENCE: 247
caggtgcagc tgcaggagtc tgggggaggc tcggtgcaga ccggagggtc tctgagacac      60
tcctgtgcag cctctacatc aatatacagt aacaactaca tggcctggtt cagccaggct     120
ccaggaaagg ggcgcgaggg ggtcgcagct gtttatattg acgatggtcg accatactat     180
gccgactccg tgaagggccg attcaccatc tccctagaca gcgccaagaa cacggtgtat     240
ctgcaaatga acagcctgaa acctgaggac actgccatgt actactgtgc ggcagctcca     300
ggccccttaa gtcataatta ctggtacacg tctgccaact atgactactg gggccagggg     360
acccaggtca ccgtctcctc a                                               381

<210> SEQ ID NO 248
<211> LENGTH: 381
<212> TYPE: DNA
<213> ORGANISM: Camelus bactrianus

<400> SEQUENCE: 248
caggtgcagc tgcaggagtc tgggggaggc tcggtgcaga ccggagggtc tctgagactc      60
tcctgtgcag cctctacatc aatatacagt aacaactaca tggcctggtt ccgccaggct     120
ccaggaaagg ggcgcgaggg ggtcgcagct gtttatattg gtgatggtcg cccatactat     180
gccgactccg tgaagggccg attcaccatc tccctagaca gcgccaagaa cacggtgtat     240
ctgcacatga acagcctgaa acctgaggac actgccatgt actactgtgc ggcagctcca     300
ggccccttaa gtcgtcatta ctggtacacg tccgccaact atgactactg gggcccgggg     360
acccaggtca ccgtctcctc a                                               381

<210> SEQ ID NO 249
<211> LENGTH: 381
<212> TYPE: DNA
<213> ORGANISM: Camelus bactrianus

<400> SEQUENCE: 249
caggtgcagc tgcaggagtc tgggggaggc tcggtaacga ccggagggtc tctgagactc      60
tcctgtgcag cctctacatc aatatacagt aacaactaca tggcctggtt ccgccaggct     120
ccaggaaagg ggcgcgaggg ggtcgcagct gtttatattg gtgatggtcg cccatactat     180
gccgactccg tgaagggccg attcaccatc tccctagaca gcgccaagaa cacggtgtat     240
ctgcaaatga acagcctgaa acctgaggac actgccatgt actactgtgc ggcagctcca     300
ggccccttaa gtcgtcatta ctggtacacg tccgccaact atgactactg gggcccgggg     360
acccaggtca ccgtctcctc a                                               381

<210> SEQ ID NO 250
<211> LENGTH: 363
<212> TYPE: DNA
<213> ORGANISM: Camelus bactrianus

<400> SEQUENCE: 250
caggtgcagc tgcaggagtc tgggggaggc ttggtgcagc ctgggggtc tctgagactc       60 tcctgtgcag cctctggatt caccttcagt atcatggcca tgagctgggt ccgccaggct     120
ccagggaggg gactcgagtg ggtctcaact attaatagtg atggtggcaa gacatactat     180
```

```
gcagactccg tgaagggccg cttcaccgcc tccagagaca acgccaagaa cacgctgtat    240
ctgcaattga atagcctgag aactgaggac acggccatgt attactgccg acggtgcgcg    300
gatatttact gttcaggttc cggcggatgg acgggccagg ggacccaggt caccgtctcc    360
tca                                                                  363
```

<210> SEQ ID NO 251
<211> LENGTH: 378
<212> TYPE: DNA
<213> ORGANISM: Camelus bactrianus

<400> SEQUENCE: 251

```
caggtgcagc tgcaggagtc tgggggaggc tcggtgcaga ctggagggtc tctgagactc     60
tcctgtgcag tctctggatt caccgacacc tacttcgcct tggctggtt ccgccaggct    120 ccagggaagg agcgcgaggg ggtcgcagct attgatagtg atggtagcac aagctacgca    180
gactccgtga agggccgatt caccatctcc aaagacaacg ccaagaacac ggtgtatctg    240
caaatgaaca gcctgaaacc tgaggacact gccatgtact actgtgcggc agctccaggc    300
cccttaagtc gtaactactg gtacacgtcc gccaactatg actactgggg ccaggggacc    360
caggtcaccg tctcctca                                                  378
```

<210> SEQ ID NO 252
<211> LENGTH: 381
<212> TYPE: DNA
<213> ORGANISM: Camelus bactrianus

<400> SEQUENCE: 252

```
caggtgcagc tgcaggagtc tgggggaggc tcggtgcaga ccggagggtc tctgagactc     60
tcctgtgcag cctctacatc aatatacagt aacaactaca tggcctggtt ccgccaggct    120
ccagcaaagg gacgcgaggg ggtcgcagct gtttatattg gtgatggtcg cccatactat    180
gccgactccg tgaagggccg attcaccatc tccctagaca cgccaagaa cacggtgtat    240 ctgcaaatga acagcctgaa acctgaggac actgccatat actactgtgc ggcagctcca    300
ggccccttaa gtcgtcatta ctggtacacg tccgccaact atgactactg ggggcccgggg    360 acccaggtca ccgtctcctc a                                              381
```

<210> SEQ ID NO 253
<211> LENGTH: 381
<212> TYPE: DNA
<213> ORGANISM: Camelus bactrianus

<400> SEQUENCE: 253

```
caggtgcagc tgcaggagtc tgggggaggc tcggtgcaga ccggagggtc tctgagactc     60
tcctgtgcag cctctacatc aatatacaat aacaactaca tggcctggtt cagccaggct    120
ccaggaaagg ggcgcgaggg ggtcgcagct gtttatattg aagatggtcg cccatactat    180
gccgactccg tgaagggccg attcaccatc tccctagaca cgccaagaa cacggtgtat    240 ctgcaaatga acagcctgaa acctgaggac actgccatgt actactgtgc ggcagctcca    300
ggccccttaa gtcgtaacta ctggtacacg tccgccaact atgactactg gggccagggg    360
acccaggtca ccgtctcctc a                                              381
```

<210> SEQ ID NO 254
<211> LENGTH: 381
<212> TYPE: DNA
<213> ORGANISM: Camelus bactrianus

<400> SEQUENCE: 254

```
caggtgcagc tgcaggagtc tgggggaggc tcggtgcaga ccggagggtc tctgagactc      60
tcctgtgcag cctctacatc aatatacagt aacaactaca tggcctggtt ccgccaggct     120
ccaggaaagg ggcgcgaggg ggtcgcagct gtttatattg atgacggtcg cacatactat     180
gccgactccg tgaagggccg attcgccatc tccctagaca cgccaagaa cacggtgtat      240
ctgcaaatga acagcctgaa acctgaggac actgccatgt actactgtgc ggcagctcca     300
ggccccttaa gtcgtcatta ctggtacacg tccgccaact atgactactg ggcccgggg      360
acccaggtca ccgtctcctc a                                               381
```

<210> SEQ ID NO 255
<211> LENGTH: 363
<212> TYPE: DNA
<213> ORGANISM: Camelus bactrianus

<400> SEQUENCE: 255

```
caggtgcagc tgcaggagtc tgggggaggc ttggtgcagc ctggggggtc tctgagactc     60
tcctgtgcag cctctggatt caccttcagt agcttggcca tgagctgggt ccgccaggct    120
ccagggaagg gactcgagtg ggtctcaact attaatagtg ggggtgtcta cacatactat    180
gcagactccg tgaagggccg cttcaccatc tccagagaca cgccaagaa cacgctgtat     240
ctgcaattga ataacctgag aactgaggac acggccatgt attactgccg acggtgcacg    300
gatatttact gttcaggttc cggcggatgg acgggccagg ggacccaggt caccgtctcc    360
tca                                                                  363
```

<210> SEQ ID NO 256
<211> LENGTH: 363
<212> TYPE: DNA
<213> ORGANISM: Camelus bactrianus

<400> SEQUENCE: 256

```
caggtgcagc tgcaggagtc tgggggaggc ttggtgcagc ctggggggtc tctgagactc     60
tcctgtgcag tctctggatt caccttcagt atcattgcca tgagctgggt ccgccaggct    120
ccagggaagg gactcgagtg ggtctcaact attaatagtg atggtggcac cacatactat    180
gcagactccg tgaagggccg cttcaccatc tccagagaca cgccaagaa cacgctgtat     240
ctgcaattga atagcctgag aactgaggac acggccatgt attactgccg acggtgcgcg    300
gatatttact gttcaggttc cggcggatgg acgggccagg ggacccaggt caccgtctcc    360
tca                                                                  363
```

<210> SEQ ID NO 257
<211> LENGTH: 366
<212> TYPE: DNA
<213> ORGANISM: Camelus bactrianus

<400> SEQUENCE: 257

```
caggtgcagc tgcaggagtc tgggggaggc ttggtgcagc ctggggggtc tctgagactc     60
tcctgtgaag cctctggact cccttcagt atcattgcca tgagctgggt ccgccaggct    120
ccagggaagg gactcgagtg ggtctcaact attaatagtg atggtggcac cacacactat    180
gcagactccg tgaagggccg cttcaccatc tccagagaca cgccaagaa cacgctgtat     240
ctgcaattga atagcctgag atctgaggac acggccatgt attactgccg acggtgcacg    300
```

-continued

```
gatatttact gttcaggttc cggcggatcg actaagggcc aggggaccca ggtcaccgtc    360
tcctca                                                               366

<210> SEQ ID NO 258
<211> LENGTH: 381
<212> TYPE: DNA
<213> ORGANISM: Camelus bactrianus

<400> SEQUENCE: 258
caggtgcagc tgcaggagtc tggaggaggc tcggtgcaga ccggagggtc gctgagactc     60
tcctgtgcag cctctacatc aatatacagt aacaactaca tggcctggtt ccgccaggct    120
ccaggaaagg ggcgcgaggg ggtcgcagct gtttatattg gtgatggtcg cccatactat    180
gccgactccg tgaagggccg attcaccatc tccctagaca cgccaagaaa cacggtgtat    240
ctgcaaatga acagcctgaa acctgaggac actgccatgt actactgtgc ggcagctcca    300 ggcccccttaa gtcgtcatta ctggtacaca accgccaact atgactactg gggcccgggg    360
acccaggtca ccgtctcctc a                                              381

<210> SEQ ID NO 259
<211> LENGTH: 381
<212> TYPE: DNA
<213> ORGANISM: Camelus bactrianus

<400> SEQUENCE: 259
caggtgcagc tgcaggagtc tggaggaggc tcggtgcagg ctggagggtc tctgagactc     60
tcctgtgcag cctctggata cacccgcagt agctactgca tgggctggtt ccgccaggct    120
ccagggaagg agcgcgagag ggtcgcacac atttatactg gtagtggaac gacacactat    180
gccgactcca tgaagggccg attcaccatc tcccaagaca cggcaagaa cacgctgtat    240 ctgcaaatga acaatctgaa acctgaggac actgccatgt actactgtgc ggcagggaca    300
agtggtactt cgtgcgccac cggtccgttc gtgtatgggt actggtactg gggccagggg    360
acccaggtca ccgtctcctc a                                              381

<210> SEQ ID NO 260
<211> LENGTH: 387
<212> TYPE: DNA
<213> ORGANISM: Camelus bactrianus

<400> SEQUENCE: 260
caggtgcagc tgcaggagtc tggaggaggc tcggtgcagg ctggagggtc tctgagactc     60
tcctgtgcat acacgcccag gcgcttatgc atgggcatgg gctggttccg ccagggtcta    120
gggaaggagc gcgagggggt cgcaacgatt gatgatgccg aagcacaac ctacgctgac    180 tccgtgaagg cccgattcac catctcccaa gacaacgcca agaacactct gtatctgcaa    240
atggacagcc tgaaacccga agacagcgcc atgtattact cgcggcccg ggctggtgtc    300 ggttggtatc aggtttcatg cccggaggag agtaggactt ctgcctttgt gtactggggc    360
cagggaaccc aggtcaccgt ctcctca                                        387

<210> SEQ ID NO 261
<211> LENGTH: 381
<212> TYPE: DNA
<213> ORGANISM: Camelus bactrianus

<400> SEQUENCE: 261
caggtgcagc tgcaggagtc tggggggaggc tcggtgcaga ccggagggtc tctgagactc     60
```

```
tcctgtgcag cctctacatc aatatacaat aacaactaca tggcctggtt cagccaggct    120
ccaggaaagg ggcgcgaggg ggtcgcagct gtttatattg aagatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtaacta ctggtacacg tccgccaact atgactactg gggccagggg    360
acccaggtca ccgtctcctc a                                              381

<210> SEQ ID NO 262
<211> LENGTH: 363
<212> TYPE: DNA
<213> ORGANISM: Camelus bactrianus

<400> SEQUENCE: 262
caggtgcagc tgcaggagtc tgggggaggc ttggtgcagc ctggggggtc tctgagactc     60
tcctgtgcag cctctggatt gaccttcagt atcgttgcca tgagctgggt ccgccaggct    120
ccaggaaagg gactcgagtg ggtctcaact attaatagtg atggtggcag cacatactat    180
gcagactccg tgaagggccg cttcaccatc tccagagaca cgccaagaa cacgctgtat     240 ctgcaattga atagcctgag aactgaggac acggccatgt attactgccg acggtgcacg    300
gatatttact gttcaggttc cggcggatgg acgggccagg ggacccaggt caccgtctcc    360
tca                                                                  363

<210> SEQ ID NO 263
<211> LENGTH: 381
<212> TYPE: DNA
<213> ORGANISM: Camelus bactrianus

<400> SEQUENCE: 263
caggtgcagc tgcaggagtc tggaggaggc tcggtgcaga ccggagggtc tctgagactc     60
tcctgtgcag cctctacatc aataatcagt ttcaactaca tggcctggtt ccgccgggct    120
ccaggaaagg ggcgcgaggg ggtcgcggct gtttatattg atgatggtcg cccatactat    180
gccgactccg tgaagggccg attcaccatc tccctagact ccgccaagaa cacggtgtat    240
ctgcaaatgg gcagcctgag acctgaggac actgccatgt actactgtgc ggcagctcca    300
ggccccttaa gtcgtaatta ctggcacacg cccgccaact atgactactg gggccagggg    360
acccaggtca ccgtctcctc a                                              381

<210> SEQ ID NO 264
<211> LENGTH: 372
<212> TYPE: DNA
<213> ORGANISM: Camelus bactrianus

<400> SEQUENCE: 264
caggtgcagc tgcaggagtc tggaggaggc tcggtgcaga ccggagggtc tctgagactc     60
tcctgtgcag cctctggata cgccggcagg ctctactcta tgggctggtt ccgccaggtt    120
gcagggaagg agcgcgaggg ggtctcgagt attgaaagtg atggcagtac gttctataca    180
gactccgtga agggccgatt caccacaacc cgagacagcg ccaagaacac tctatatctc    240
caaatgaaca acctgaaacc tgaggacact gccatgtact actgcgcggc attttgcctg    300
cgagtaggac atggtggtcg ctgcacagag tataaatact ggggccgggg gacccaggtc    360
accgtctcct ca                                                        372
```

<210> SEQ ID NO 265
<211> LENGTH: 381
<212> TYPE: DNA
<213> ORGANISM: Camelus bactrianus

<400> SEQUENCE: 265

```
caggtgcagc tgcaggagtc tgggggaggc tcggtgcagg ctggagggtc tctgagactc      60
tcctgtgcag cctctggata cacccgcagt agttactgca tgggctggtt ccgccaggct     120
ccagggaagg agcgcgagag ggtcgcacac atttatactg gtagtggaag cacacactat     180
gccgactccg tgaagggccg attcaccatc tcccaagaca acggcaagaa cacgctgtat     240
ctgcaaatga acaatctgaa acctgaggac actgccatgt actactgtgc ggcagggaca     300
agtggtactt cgtgcgccac cggtccgttc gtgtataaat actggtactg gggccagggg     360
acccaggtca ccgtctcctc a                                                381
```

<210> SEQ ID NO 266
<211> LENGTH: 369
<212> TYPE: DNA
<213> ORGANISM: Camelus bactrianus

<400> SEQUENCE: 266

```
ctggtgcagc tgcaggagtc tgggggaggc ttggtgcagc ctgggggtc tctgagactc       60
tcctgtgcag cctctggatt cgccttcagt acctatgcca tgagctgggt ccgccaggct     120
ccagggaagg gactcgagtg ggtctcaggt attaatggtg gtggtggtaa cacatactat     180
gcagactccg tgaagggccg attcaccatc tccagagaca acgccaagaa cacgctgtat     240
ctgcaattga acagcctgaa aactgaggac acggccatgt attactgtgg acaaggggca     300
tattgggcat attgtaacgg tggttactgc aatcctccgg gccaggggac ccaggtcacc     360
gtctcctca                                                              369
```

<210> SEQ ID NO 267
<211> LENGTH: 381
<212> TYPE: DNA
<213> ORGANISM: Camelus bactrianus

<400> SEQUENCE: 267

```
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttatattg gtgatggtcg cccatactat     180
gccgactccg tgaagggccg attcaccatc tccctagaca gcgccaagga cacggtgtat     240
ctgcaaatga acagcctgaa acctgaggac actgccatgt actactgtgc ggcagctcca     300
ggccccttaa gtcgtaatta ctggtacacg tccgccaact atgactactg gggccagggg     360
acccaggtca ccgtctcctc a                                                381
```

<210> SEQ ID NO 268
<211> LENGTH: 381
<212> TYPE: DNA
<213> ORGANISM: Camelus bactrianus

<400> SEQUENCE: 268

```
caggtgcagc tgcaggagtc tgggggaggc tcggtgcaga ccggagggtc tctgagactc      60
tcctgtgcag cctctgcatc aatatacagt aacaactaca tggcctggtt cagccaggct     120
ccaggaaagg ggcgcgaggg ggtcgcagct gtttatattg gtgatggtcg cccatactat     180
```

```
gacgactccg tgaagggact attcaccatc tccctagaca gcgccaagaa cacggtgtat      240
ctgcaaatga acagcctgaa acctgaggac actgccatgt actactgtgc ggcagctcca      300
ggacccttaa ttcgtaatta ctggtacacg tccgccaact atgactactg gggccagggg      360
acccaggtca ccgtctcctc a                                                381

<210> SEQ ID NO 269
<211> LENGTH: 381
<212> TYPE: DNA
<213> ORGANISM: Camelus bactrianus

<400> SEQUENCE: 269
caggtgcagc tgcaggagtc tgggggaggc tcggtgcaga ccggagggtc tctgagactc      60
tcctgtgcag cctctacatc actatacagt tacaactaca tggcctggtt cagccaggct      120
ccaggaaagg ggcgcgaggg ggtcgcagct gtttatgttg gtgatggtcg cccatactat      180
gccgactccg tgaagggccg attcaccatc tccctagaca gcgccaagaa cacggtgtat      240
ctgcaaatga acagcctgaa acctgaggac actgccatgt actactgtgc ggcagctcca      300
ggccccttaa gtcgtaatta ctggtacacg tccgccaact atgactactg gggccagggg      360
acccaggtca ccgtctcctc a                                                381

<210> SEQ ID NO 270
<211> LENGTH: 375
<212> TYPE: DNA
<213> ORGANISM: Camelus bactrianus

<400> SEQUENCE: 270
caggtgcagc tgcaggagtc tgggggaggc tcagtgcagg ctgggggtc tctgagactc       60 tcctgcacag cccctggatt cacctccaac acctgcgcca tggcgtggtt ccgccaggct      120
ccagggaaag agcgcgagtt cgtctcatct atgagtactg tcggttccac gaggtttgca      180
gactccgtga agggccgatt caccatctcc aaagacgaag tcaaggacac ggtctatctg      240
caaatgaaca gcctgaaacc tgaggacacg gccatgtatt tttgtaagac ctatgcgtgt      300
agagaatgta ctggtcggta ttgtcgtaca gctccggatg catggggcca ggggacacag      360
gtcaccgtct cctca                                                       375

<210> SEQ ID NO 271
<211> LENGTH: 375
<212> TYPE: DNA
<213> ORGANISM: Camelus bactrianus

<400> SEQUENCE: 271
caggtgcagc tgcaggagtc tgggggaggc tcagcgcagg ctgggggtc tctgagactc       60 tcctgcacag cccctggatt cacctccaac acctgcgcca tggcgtggta ccgccaggct      120
ccagggaaag agcgcgagtt cgtctcatct cgcagcactg tcggtaccac ggggtatgca      180
gactccgtga agggccgatt caccatctcc aaagacgaag ccaaggacac ggtctatctg      240
caaatgaaca gcctgaaacc tgaggacacg gccatgtatt tttgtaagac ctatgcgtgt      300
agaaattgta ttggtcggca ttgtcgtaca gctccggatg catggggcca ggggacacag      360
gtcaccgtct cctca                                                       375

<210> SEQ ID NO 272
<211> LENGTH: 375
<212> TYPE: DNA
```

<213> ORGANISM: Camelus bactrianus

<400> SEQUENCE: 272

| caggtgcagc | tgcaggagtc | tgggggaggc | tcagtgcagg | ctgggggtc | tctgagactc | 60 |
| tcctgcacag | cccctggatt | cacctccaac | acctgcgcca | tggcgtggtt | ccgccaggct | 120 |
| ccagggaaag | agcgcgagtt | tgtctcatcg | ctcagcactg | tcggtaccac | ggggtatgca | 180 |
| gactccgtga | agggccgatt | caccatctcc | aaagacgagg | ccaaggacac | ggtctatctg | 240 |
| ctaatgaaca | gcctgaaacc | cgaggacacg | gccatgtatt | tttgtaagac | atttgcgtgt | 300 |
| agagattgtt | ctggtcggta | ttgtcgtaca | gctccggatg | catggggcca | ggggacacag | 360 |
| gtcaccgtct | cctca | | | | | 375 |

<210> SEQ ID NO 273
<211> LENGTH: 375
<212> TYPE: DNA
<213> ORGANISM: Camelus bactrianus

<400> SEQUENCE: 273

| caggtgcagc | tgcaggagtc | tgggggaggc | tcagtgcagg | ctgggggtc | tctgagactc | 60 |
| tcctgcacag | cccctggatt | cacctccaac | acctgcgcca | tggcgtggta | ccgccaggct | 120 |
| ccagggaaag | agcgcgagtt | cgtctcatct | cgcagcactg | tcggtaccac | ggggtatgca | 180 |
| gactccgtga | agggccgatt | caccatctcc | aaagacgagg | ccaaggacac | ggtctatctg | 240 |
| caaatgaaca | gcctgaaacc | tgaggacacg | gccatgtatt | tttgtaagac | ctatgcgtgt | 300 |
| agaaattgta | ttggtcggca | ttgtcgtaca | gctccggatg | catggggcca | ggggacacag | 360 |
| gtcaccgtct | cctca | | | | | 375 |

<210> SEQ ID NO 274
<211> LENGTH: 387
<212> TYPE: DNA
<213> ORGANISM: Camelus bactrianus

<400> SEQUENCE: 274

| caggtgcagc | tgcaggagtc | tggaggaggc | tcggtgcagg | ctggaaggtc | tctgagactc | 60 |
| tcttgtgcag | tctcgagata | cagcgccagt | aacaacgtca | tcaagtggat | gggctggttc | 120 |
| cgccaggctc | cagggaagga | gcgcgagggg | gtcgcggcac | tttatactag | tggtggtaac | 180 |
| acatactatg | ccgactccgt | gaagggccga | ttcaccatct | ccagagacta | ctccgagaac | 240 |
| acggtgtctc | tccaaatgaa | caacctgaaa | ccagaggaca | ctggcatgta | ctactgtgcg | 300 |
| gctactgttg | gacggtcct | agctggcccg | ttatctgcgc | gaaaatataa | ctactggggc | 360 |
| caggggaccc | aggtcaccgt | ctcctca | | | | 387 |

<210> SEQ ID NO 275
<211> LENGTH: 366
<212> TYPE: DNA
<213> ORGANISM: Camelus bactrianus

<400> SEQUENCE: 275

| caggtgcagc | tgcaggagtc | tgggggaggc | ttggtgcagc | ctgggggtc | tctgagactc | 60 |
| tcctgtgcag | cctctggatt | caccttcagt | aactctgaca | tggcctggtt | tcgccaggct | 120 |
| ccagggaagg | gactcgagtg | ggtctcagtt | attgatagtg | gtggtggtta | cacatactat | 180 |
| gcagactccg | tgaagggccg | attcaccatc | tccagagaca | acgccgagaa | cacgctgtat | 240 |
| ctgcaattga | acagcctgaa | aactgaggac | acggccatgt | attactgtgc | aaaaaccgat | 300 |

```
ctaaggtact ctaggattta tccgtacgga aagtggggcc aggggaccca ggtcaccgtc    360
tcctca                                                               366

<210> SEQ ID NO 276
<211> LENGTH: 387
<212> TYPE: DNA
<213> ORGANISM: Camelus bactrianus

<400> SEQUENCE: 276
caggtgcagc tgcaggagtc tgggggaggc tcggtgcagg ctggaaggtc tctgagactc     60
ccttgtgcag tctcgagata cagcgccagt aacaacgtca tcaagtggat gggctggttc    120
cgccaggctc cagggaagga gcgcgagggg gtcgcggcac tttatactag tggtggtaac    180
acatactatg ccgactccgt gaagggccga ttcaccatct ccagagacta ctccgagaac    240
acggtgtctc tccaaatgaa caacctgaaa ccagaggaca ctggcatgta ctactgtgcg    300
gctactgttg ggacggtcct agctggcccg ttatctgcgc gaaaatataa ctactggggc    360
caggggaccc aggtcaccgt ctcctca                                        387

<210> SEQ ID NO 277
<211> LENGTH: 375
<212> TYPE: DNA
<213> ORGANISM: Camelus bactrianus

<400> SEQUENCE: 277
caggtgcagc tgcaggagtc tgggggaggc ttggtgcagg caggggggtc tctgacactc     60
tcctgtagag gctctggatt cacctccaac acctgcgcca tggcgtggtt ccgccaggct    120
ccagggaaag agcgcgagtt cgtctcatct atgagtactg tcggttccac gaggtttgca    180
gactccgtga agggccgatt caccatctcc aaagacgaag ccaaggacac ggtctatctg    240
caaatgaaca gcctgaaacc tgaggacacg gccatgtatt tttgtaagac ctatgcgtgt    300
agagaatgta ctggtcggta ttgtcgtaca gctccggatg catggggcca gggacacag     360 gtcaccgtct cctca                                                     375

<210> SEQ ID NO 278
<211> LENGTH: 375
<212> TYPE: DNA
<213> ORGANISM: Camelus bactrianus

<400> SEQUENCE: 278
caggtgcagc tgcaggagtc tgggggaggc tcagtgcagg ctgggggtc tctgagactc      60 tcctgcacag cccctggatt cacctccaac acctgcgcca tggcgtggtt ccgccaggct    120
ccagggaaag agcgcgagtt cgtctcatct atgagcactg gcgtaccac gggatatgga    180 gactccgtga agggccgatt caccagctcc aaagacgcag ccaaggacac ggtctatctg    240
caaatgaaca gcctgaaacc tgaggacacg gccatatatt tttgtaagac ctatgcgtgt    300
agagattgta ttggtcggta ttgtcgtaca gctccggatg catggggcca gggacacag     360 gtcaccgtct cctca                                                     375

<210> SEQ ID NO 279
<211> LENGTH: 375
<212> TYPE: DNA
<213> ORGANISM: Camelus bactrianus

<400> SEQUENCE: 279
```

```
caggtgcagc tgcaggagtc tggggggaggc tcagtgcagg ctgggggtc tctgagactc      60 tcctgcacag ccctggatt cacctccaac acctgcgcca tggcgtggta ccgccaggct       120
ccagggaaag agcgcgagtt cgtctcatct cgcagcactg tcggtaccac ggggtatgca      180
gactccgtga agggccgatt caccctctcc aaggacgaag ccaaggacac ggtctatctg      240
caaatgaaca gcctgaaacc tgaggacacg gccatgtatt tttgtaagac ctatgcgtgt     300
agaaattgta ttggtcggca ttgtcgtaca gctccggatg catggggcca ggggacacag     360
gtcaccgtct cctca                                                      375
```

```
<210> SEQ ID NO 280
<211> LENGTH: 378
<212> TYPE: DNA
<213> ORGANISM: Camelus bactrianus

<400> SEQUENCE: 280
caggtgcagc tgcaggagtc tggaggaggg tcggtgcagg ctggagagac tctgagactc     60
tcctgtacag tctctggaga cacttttgaa gcctctggcg tgggctggtt ccgccaggtt    120
tcagggaatg aatgcgactt ggtctcaagt attaatcgtg atggtaccac atactataca    180
ccctccgtgg cgggccgatt tacgatgtcc caaaacaacg ccaagaacac ggtatatctg    240
caaatgaaca gcctgaaacc tgacgacaca gccgtgtatt actgtgcgac agaccccgcc    300
gtggggattg tagtgaggag cacttgtaga ggccccttg gttactgggg ccaggggacc    360
caggtcaccg tctcctca                                                    378
```

```
<210> SEQ ID NO 281
<211> LENGTH: 378
<212> TYPE: DNA
<213> ORGANISM: Camelus bactrianus

<400> SEQUENCE: 281
caggtgcagc tgcaggagtc tggaggaggt tcggtgcagg ctggagggtc tctgagactc     60
tcctgtacag tctctggaaa caccgacagt atgaatctca tgggctggtt ccgccaggct    120
ccagggaagg agcgcgaggg ggtcgcaagt atttatactg gaagtaggac cataacctac    180
cccgactccg tgaagggccg attcaccatc tcccaagaca cgccaagaa cacggtgtat    240 ctgcaaatga acagcctgaa acctgaggac actgccatgt actactgtgc ggcagattac   300
cgagctcgat acggtgcctc acttcggaca agtgcctata cctactgggg ccaggggacc   360
caggtcaccg tctcctca                                                    378
```

```
<210> SEQ ID NO 282
<211> LENGTH: 375
<212> TYPE: DNA
<213> ORGANISM: Camelus bactrianus

<400> SEQUENCE: 282
caggtgcagc tgcaggagtc tggggggaggc tcagtgcagg ctgggggtc tctgagactc     60 tcctgcacag ccctggatt cacctccaac acctgcgcca tggcgtggta tcgccaggct    120
ccagggaaag agcgcgagtt cgtctcatct cgcagcactg tcggtaccac ggggtatgca    180
gactccgtga agggccgatt caccatctcc aaagacgaag ccaaggacac ggtctatctg   240
caaatgaaca gcctgaaacc tgaggacacg gccaagtatt tttgtaagac ctatgcgtgt    300
agagattgta tcggtcggta ttgtcgtaca gctccggatg catggggcca ggggacacag   360
gtcaccgtct cctca                                                      375
```

<210> SEQ ID NO 283
<211> LENGTH: 372
<212> TYPE: DNA
<213> ORGANISM: Camelus bactrianus

<400> SEQUENCE: 283

```
caggtgcagc tgcaggagtc tgggggaggc tcggtgcagg ctggagggtc tctgaaactc      60
tcctgcgtag tctctggata cacctggtgt aggtacgaca tgagctggta ccgccaggct     120
ccagggaagg agcgcgagtt cgtctcagtt attgatgata atggtagtac gaactacgca     180
gactccgtga agggccgatt caccatttcc aaagacaacg caacacggt gactctgcaa      240
atgaccagcc tgaaacctgc ggacacggcc atgtattact gtcagacagg aagataccga     300
tcaaggctcg gttatggacg tgtcccagc ggtgactact ggggcctggg acccaggtc       360
accgtctcct ca                                                         372
```

<210> SEQ ID NO 284
<211> LENGTH: 372
<212> TYPE: DNA
<213> ORGANISM: Camelus bactrianus

<400> SEQUENCE: 284

```
caggtgcagc tgcaggagtc tgggggaggc tcggtgcagg ctggagggtc tctgagactc      60
tcctgtgcag tctctggata cagcatcagt aattactgca tggggtggtt ccgccagcct     120
ccagggaagg aacgcgaggg ggtcgcaaat attgatacgt ggggtgtgac aagctacaca     180
gactccgtga agggccgctt caccatctcc aaagacaacg ccaagaatac tctgtacctg     240
caaatgaaca gcctgaaacc tgaggacact gccctgtact actgcgcgcg cagacaattt     300
gtcaactgtg gcactctggc gccagtgaat tacgtgaact ggggccaggg gacccaggtc     360
accgtctcct ca                                                         372
```

<210> SEQ ID NO 285
<211> LENGTH: 363
<212> TYPE: DNA
<213> ORGANISM: Camelus bactrianus

<400> SEQUENCE: 285

```
caggtgcagc tgcaggagtc tgggggaggt tcggtgcagg ctgggggtc tctgagactc       60
tcctgtacag cctctggatt caccttcagt acgttagcca tgagctgggt ccgccaggct     120
ccaggaaagg gactcgagtg gtctcaact attagtagta ctggtggcgc cacatactat      180
gcagactccg tgaagggccg attcaccatc tccagagaca cgccaaaaa cacgctgtat      240
ctgcaattga acagcctgaa acctgaggac acggccatgt attactgtcg aaggtgcacg     300
gatatttact gttcaaattc cgcacgatgg acgggccagg gacccaggt caccgtctcc      360
tca                                                                   363
```

<210> SEQ ID NO 286
<211> LENGTH: 363
<212> TYPE: DNA
<213> ORGANISM: Camelus bactrianus

<400> SEQUENCE: 286

```
caggtgcagc tgcaggagtc tggaggaggc ttggtgcagc ctgggggtc tctgagactc       60
tcctgtacag cctctggatt caccttcagt acgttagcca tgagctgggt ccgccaggct     120
```

```
ccaggaaagg gactcgagtg ggtctcaact attagtagta ctggtggcgc cacatactat    180
gcagactccg tgaagggccg attcaccatc tccagagaca acgccaaaaa cacgctgtat    240
ctgcaattga acagcctgaa acctgaggac acggccatgt attactgtcg aaggtgcacg    300
gatatttact gttcaaattc cgcacgatgg acgggccagg ggacccaggt caccgtctcc    360
tca                                                                  363
```

```
<210> SEQ ID NO 287
<211> LENGTH: 360
<212> TYPE: DNA
<213> ORGANISM: Camelus bactrianus

<400> SEQUENCE: 287
caggtgcagc tgcaggagtc tggaggaggc ttggtgcagc ctgggggtc tctgagactc      60 tcctgtgtag cctctggatt cagcttcagt agctctggca tgagctgggt ccgccaggct    120
ccagggaagg gactcgagtg ggtgtcaact attagttata atggtggtag cacattctat    180
acagactccg tgaagggccg attcaccatc tccagagaca acgccaagaa cacgctgtat    240
ctgcaattga acagcctgaa aactgaggac acggccatgt attactgtgc aaaaagtggg    300
acaccagtgt tggcgcctaa ttcggtccgg ggccagggga cccaggtcac cgtctcctca    360
```

```
<210> SEQ ID NO 288
<211> LENGTH: 381
<212> TYPE: DNA
<213> ORGANISM: Camelus bactrianus

<400> SEQUENCE: 288
caggtgcagc tgcaggagtc tggaggaggc tcggtgcagg ctggagggtc tctgagactc      60
tcctgtgtgt cctctggata cgcctacaat aggtactaca tggcctggtt cagccaggct    120
ccaggaaagg ggcgcgaggg ggtcgcagct gtttatattg gtgatggtcg cccatactat    180
gccgactccg tgaagggccg attcaccatc tccctagaca cgccaagaa cacggtgtat     240 ctgcaaatga acagcctgaa acctgaggac actgccatgt actactgtgc ggcagctcca    300
ggccccttaa gtcgtaatta ctggtacacg tccgccaact atgactactg gggccagggg    360
acccaggtca ccgtctcctc a                                              381
```

```
<210> SEQ ID NO 289
<211> LENGTH: 366
<212> TYPE: DNA
<213> ORGANISM: Camelus bactrianus

<400> SEQUENCE: 289
caggtgcagc tgcaggagtc tggggaggc tcggtgcagg ctggagggtc tctgagactc       60
tcctgtgtag cctcaggata caccaactgt aggtacgaca tgagctggta ccgccaggct    120
ccagggaagg agcgcgagtt cgtctcatct atcgatagtg aaggtgtggc aaggcacgca    180
gactccgtga aggccgatt cggcatctcc aagacaacg ccaagagcac gctgtatctc      240
caaatgaaca gcctgaaacc tgaggacacg gccgtgtatt actgtaaaac ggattatata    300
acatgtagat tggtagctg gtccgattcg acctgggggcc agggaccca ggtcaccgtc     360 tcctca                                                                366
```

```
<210> SEQ ID NO 290
<211> LENGTH: 366
<212> TYPE: DNA
<213> ORGANISM: Camelus bactrianus
```

<400> SEQUENCE: 290

| | | | | |
|---|---|---|---|---|
| caggtgcagc | tgcaggagtc | tgggggaggc | tcggtgcagg | ctggagggtc | tctgagactc | 60 |
| tcctgtgtag | cctctggata | caccaactgt | aggtacgaca | tgagctggta | ccgccaggct | 120 |
| ccggggaagg | agcgcgagtt | cgtctcatct | atcgatagtg | aaggtgtggc | aaggcacgca | 180 |
| gactccgtga | aaggccgatt | cggcatctcc | aagacaacg | ccaagagcac | gctgtatctc | 240 |
| caaatgaaca | gcctgaaacc | tgaggacacg | gccatgtatt | actgtaaaat | ggattatata | 300 |
| agatgtagat | ttggtagctg | gtccgagtcg | acctggggcc | aggggaccca | ggtcaccgtc | 360 |
| tcctca | | | | | | 366 |

<210> SEQ ID NO 291
<211> LENGTH: 375
<212> TYPE: DNA
<213> ORGANISM: Camelus bactrianus

<400> SEQUENCE: 291

| | | | | | | |
|---|---|---|---|---|---|---|
| caggtgcagc | tgcaggagtc | tgggggaggc | tcagtgcagg | ctgggggtc | tctgagactc | 60 |
| tcctgcacag | cccctggatt | cacctccaac | acctgcgcca | tggcgtggtt | ccgccaggct | 120 |
| ccagggaaag | agcgcgagtt | cgtctcatct | atgagtactg | tcggttccac | gaggtttgca | 180 |
| gactccgtga | agggccgatt | caccatctcc | aaagacgaag | ccaaggacac | ggtctatctg | 240 |
| caaatgaaca | gcctgaaacc | tgaggacacg | gccatgtatt | tttgtaagac | ctatgcgtgt | 300 |
| agagaatgta | ctggtcggta | ttgtcgtaca | gctccggatg | catggggcca | ggggacacag | 360 |
| gtcaccgtct | cctca | | | | | 375 |

<210> SEQ ID NO 292
<211> LENGTH: 387
<212> TYPE: DNA
<213> ORGANISM: Camelus bactrianus

<400> SEQUENCE: 292

| | | | | | | |
|---|---|---|---|---|---|---|
| caggtgcagc | tgcaggagtc | tggaggaggc | tcggtgcaga | ctggagggtc | tctgagactc | 60 |
| tcttgtgcag | tctcgagata | cagcgccagt | aacaacgtca | tcaagtggat | gggctggttc | 120 |
| cgccaggctc | cagggaagga | gcgcgagggg | gtcgcggcac | tttatactag | tggtggtaac | 180 |
| acatactatg | ccgactccgt | gaagggccga | ttcaccatct | ccagagacta | ctccgagaac | 240 |
| acggtgtctc | tccaaatgaa | caacctgaaa | ccagaggaca | ctggcatgta | ctactgtgcg | 300 |
| gctactgttg | gacggtcct | agctggcccg | ttatctgcgc | gaaaatataa | ctactggggc | 360 |
| caggggaccc | aggtcaccgt | ctcctca | | | | 387 |

<210> SEQ ID NO 293
<211> LENGTH: 375
<212> TYPE: DNA
<213> ORGANISM: Camelus bactrianus

<400> SEQUENCE: 293

| | | | | | | |
|---|---|---|---|---|---|---|
| caggtgcagc | tgcaggagtc | tgggggaggc | tcagtgcagg | ctgggggtc | tctgagactc | 60 |
| tcctgcacag | cccctggatt | cacctccaac | acctgcgcca | tggcgtggta | ccgccaggct | 120 |
| ccagggaaag | agcgcgagtt | cgtctcatct | atcagcactg | tccgtaccac | ggcatatgca | 180 |
| gactccgtga | agggccgatt | caccatctcc | aaagacgaag | ccaaggccac | ggtctatctg | 240 |
| caaatgaaca | gcctgaaacc | tgaggacacg | gccatgtatt | tttgtaagag | ctatgcgtgt | 300 |

```
agagattgta ttggtcggta ttgtcgtaca gctccggatg catggggcca ggggacacag    360
gtcaccgtct cctca                                                     375
```

<210> SEQ ID NO 294
<211> LENGTH: 387
<212> TYPE: DNA
<213> ORGANISM: Camelus bactrianus

<400> SEQUENCE: 294

```
caggtgcagc tgcaggagtc tgggggaggc tcggtgcagg ctggacagtc tctgagactc     60
tcctgtacag cctctggata taccgacagt cgatactgca tgggctggtt ccgccaggct    120
ccagggaagg agcgcgaacg ggtcacaact atacatactg gtactggtat cacatactat    180
gccgactccg tgaagggccg attctccatc tcccaagaca cgcccagaa cacgatgtat     240 ctgcaaatga acagcctgga acctgaggac actgccatgt actactgtgc gacaaccgat    300
tatgtatatt cagcctcagc ctcttggtgt aatggctacg ggtgtttaa caactggggc     360 caggggaccc aggtcaccgt ctcctca                                        387
```

<210> SEQ ID NO 295
<211> LENGTH: 387
<212> TYPE: DNA
<213> ORGANISM: Camelus bactrianus

<400> SEQUENCE: 295

```
caggtgcagc tgcaggagtc tgggggagac tcggtgcagg ctggaaggtc tctgagactc     60
tcttgtgcag tctcgagata cagcgccagt aacaacgtca tcaagtggat gggctggttc    120
cgccaggctc agggaagga gcgcgagggg gtcgcggcac tttatactag tggtggtaac    180
acatactatg ccgactccgt gaagggccga ttcaccatct ccagagacta ctccgagaac    240
acggtgtctc tccaaatgaa caacctgaaa ccagaggaca ctggcatgta ctactgtgcg    300
gctactgttg ggacggtcct agctggcccg ttatctgcgc gaaaatataa ctactggggc    360
caggggaccc aggtcaccgt ctcctca                                        387
```

<210> SEQ ID NO 296
<211> LENGTH: 438
<212> TYPE: DNA
<213> ORGANISM: Camelus bactrianus

<400> SEQUENCE: 296

```
caggtgcagc tgcaggagtc tgggggaggc tcggtgcagg ctggagggtc tctgagactc     60
tcttgtgcag tctcgagata cagcgccagt aacaacgtca tcaagtggat gggctggttc    120
cgccaggctc agggaagga gcgcgagggg gtcgcggcac tttatactag tggtggtaac    180
acatactatg ccgactccgt gaagggccga ttcaccatct ccagagacta ctccgagaac    240
acggtgtctc tccaaatgaa caacctgaaa ccagaggaca ctggcatgta ctactgtgcg    300
actactgttg ggacggtcct agctggcccg ttatctgcgc gaaaatataa ctactggggc    360
caggggaccc aggtcaccgt ctcctcagag gagtctcagc ctcttaatac tttcatgttt    420
cagaataata ggttccga                                                  438
```

<210> SEQ ID NO 297
<211> LENGTH: 372
<212> TYPE: DNA
<213> ORGANISM: Camelus bactrianus

<400> SEQUENCE: 297

```
caggtgcagc tgcaggagtc tgggggaggc tcggtgcagg ctggagggtc tctgagactc      60
tcctgtgcag cctctggata cacctcgagg ccgaacttca tggtctggtt ccgccaggct     120
ccagggaagg agcgcgaggc ggtcgcaggt atttatactg ttactggtgg aacactctat     180
tccgaccccg tgaagggccg attcaccatc tcccaagaca aggccaagaa cacggtgtat     240
ctgcaaatga acagcctgaa tcctgaggac actgccatgt actactgtgc ggttaaatgg     300
tatggtggta gctggtcaga cgccgccact tttcgtacct ggggccgggg acccaggtc      360 accgtctcct ca                                                        372
```

<210> SEQ ID NO 298
<211> LENGTH: 375
<212> TYPE: DNA
<213> ORGANISM: Camelus bactrianus

<400> SEQUENCE: 298

```
caggtgcagc tgcaggagtc tgggggaggc tcggtgcagg ctggagggtc tctgagactc      60
tcctgtgcag cctctggata ctcctataac atcgattaca tggcctggtt ccgccaggct     120
ccagggaagg agcgcgaggg ggtcgcagct atttatactg gtagtagacg cacatactat     180
tccgactccg tgaagggccg attcgccatc tcccaagaca acgccgacaa cacggtgtat     240
ctgcaaatga acgccctgaa acctgaggac actgccatgt acttctgtgc ggcccttgtc     300
tcccgaccgg ggcgtagttg ggataaaaat gagtatcggt actggggcca ggggacccag     360
gtcaccgtct cctca                                                     375
```

<210> SEQ ID NO 299
<211> LENGTH: 375
<212> TYPE: DNA
<213> ORGANISM: Camelus bactrianus

<400> SEQUENCE: 299

```
caggtgcagc tgcaggagtc tgggggagga ttggtgcagg caggggggtc tctgagactc      60
tcctgtacag cctctggatt cactttgat gattattcca tgggctggtt ccgccaggct      120
ccggggaagg agcgcgaggg gatctcatgt attgattgga gtggtggtcg cacaaactat     180
ggggactccg tgaagggccg attcaccatc tccagagaca acgccaagaa cacgctgtat     240
ctgcaaatga acagcctgaa acctgaagac acggccatgt attactgtgc ggccaacagc     300
gcgtactcga gttgcagcct aagcacgact cattataagt actggggcca ggggacccag     360
gtcaccgtct cctca                                                     375
```

<210> SEQ ID NO 300
<211> LENGTH: 363
<212> TYPE: DNA
<213> ORGANISM: Camelus bactrianus

<400> SEQUENCE: 300

```
caggtgcagc tgcaggagtc tgggggaggc ttggtgcagc tgggggggtc tctgagactc      60
tcctgtgcag cctctggatt caccttcagt gcctatggca tgagctgggt ccgccaggct     120
ccagggaagg gattcgagtg gtctcaact attaatagtg gtggtggcac acatttat       180 gcagactccg tgaagggccg cttcaccatc tccagagaca acgccaagaa cacgctgtat     240
```

```
ctgcaattga atagcctgag aactgaggac acggccatgt attactgccg acggtgcgcg    300
gatatttact gttcactttc cggcggatgg acgggccagg ggacccaggt caccgtctcc    360
tca                                                                  363
```